US008790919B2

(12) United States Patent
Migawa et al.

(10) Patent No.: US 8,790,919 B2
(45) Date of Patent: Jul. 29, 2014

(54) COMPOSITIONS AND METHODS FOR OPTIMIZING CLEAVAGE OF RNA BY RNASE H

(75) Inventors: Michael T. Migawa, Carlsbad, CA (US); Walter F. Lima, San Diego, CA (US); Eric E. Swayze, Carlsbad, CA (US); Joshua Nichols, Carlsbad, CA (US); Hongjiang Wu, Carlsbad, CA (US); Thazha P. Prakash, Carlsbad, CA (US); Tadeusz Krzysztof Wyrzykiewicz, Wyoming, OH (US); Balkrishen Bhat, Carlsbad, CA (US); Stanley T. Crooke, Carlsbad, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 1851 days.

(21) Appl. No.: 10/592,919

(22) PCT Filed: Mar. 15, 2005

(86) PCT No.: PCT/US2005/008428
§ 371 (c)(1),
(2), (4) Date: Jul. 31, 2007

(87) PCT Pub. No.: WO2005/089268
PCT Pub. Date: Sep. 29, 2005

(65) Prior Publication Data
US 2008/0207541 A1 Aug. 28, 2008

Related U.S. Application Data

(60) Provisional application No. 60/553,646, filed on Mar. 15, 2004, provisional application No. 60/567,016, filed on Apr. 29, 2004, provisional application No. 60/609,516, filed on Sep. 13, 2004.

(51) Int. Cl.
*C12N 15/85* (2006.01)
*C07H 21/02* (2006.01)
*C07H 21/04* (2006.01)

(52) U.S. Cl.
USPC .... 435/325; 536/23.1; 536/24.31; 536/24.33; 536/24.3; 536/24.5

(58) Field of Classification Search
None
See application file for complete search history.

(56) References Cited

U.S. PATENT DOCUMENTS

| 5,013,830 | A | 5/1991 | Ohtsuka et al. |
| 5,149,797 | A | 9/1992 | Pederson et al. |
| 5,220,007 | A | 6/1993 | Pederson et al. |
| 5,256,775 | A | 10/1993 | Froehler |
| 5,366,878 | A | 11/1994 | Pederson et al. |
| 5,403,711 | A | 4/1995 | Walder et al. |
| 5,491,133 | A | 2/1996 | Walder et al. |
| 5,565,350 | A | 10/1996 | Kmiec |
| 5,623,065 | A | 4/1997 | Cook et al. |
| 5,652,355 | A | 7/1997 | Metelev et al. |
| 5,652,356 | A | 7/1997 | Agrawal |
| 5,700,922 | A | 12/1997 | Cook |
| 2002/0160379 | A1 | 10/2002 | Cook et al. |
| 2003/0096770 | A1* | 5/2003 | Krotz et al. ............... 514/44 |
| 2003/0171211 | A1 | 9/2003 | Holtcamp |

FOREIGN PATENT DOCUMENTS

| WO | WO 03/051308 | 6/2003 |
| WO | WO 03/106645 | 12/2003 |

OTHER PUBLICATIONS

Lai et al. (J. Am. Chem. Soc. vol. 126 No. 10 2004, published on-line Feb. 21, 2004).*
Cornell et al., "A Second Generation Force Field for the Simulation of Proteins, Nucleic Acids, and Organic Molecules" J. Am. Chem. Soc. (1995) 117:5179-5197.
Denissov et al., "Solution structure of an arabinonucleic acid (ANA)/RNA duplex in a chimeric hairpin: comparison with 2'-fluoro-ANA/RNA and DNA/RNA hybrids" Nucleic Acids Res. (2001) 29:4284-4293.
Detmer et al., "Substrates for Investigation of DNA Polymerase Function: Synthesis and Properties of 4'-C-Alkylated Oligonucleotides" Eur. J. Org. Chem. (2003) 10:1837-1846.
Fraser et al., "Synthesis and Conformational Properties of 2'-Deoxy-2'-methylthio-pyrimidine and -purine Nucleosides: Potential Antisense Applications" J. Heterocycl Chem. (1993) 30:1277-1287.
Freier et al., "The ups and downs of nucleic acid duplex stability: structure-stability studies on chemically-modified DNA:RNA duplexes" Nucleic Acids Research (1997) 25(22):4429-4443.
Gait et al., "Applications of Chemically Synthesized RNA" in RNA: Protein Interactions, Ed. Smith (1998) 1-36.
Gallo et al., "2'-C-Methyluridine phosphoramiditeL a new building block for the preparation of RNA analogues carrying the 2'-hydroxyl group" Tetrahedron (2001) 57:5707-5713.
Hall et al., "Properties of a U1/mRNA 5' splice site duplex containing pseudouridine as measured by thermodynamic and NMR methods Properties of a U1/mRNA 5' splice site duplex containing pseudouridine as measured by thermodynamic and NMR methods" Biochemistry (1991) 30:1795-1801.
Iwai et al., "Recognition of 2'-hydroxyl groups by *Escherichia coli* ribonuclease H1 " FEBS Letters (1995) 368:315-320.
Katayangi et al., "Crystal Structure of *Escherichia coli* RNase H1 in Complex with Mg at 2.8 A Resolution: Proof for a Single Mg2 Binding Site" Proteins: Struct. Funct. Genet. (1993) 17:337-346.

(Continued)

*Primary Examiner* — Amy Bowman
(74) *Attorney, Agent, or Firm* — Isis Pharmaceutical, Inc. Patent Dept.; Casimir Jones, S.C.

(57) ABSTRACT

The present invention provides compositions and methods for the optimization of cleavage of RNA species by RNase H. In some embodiments, the invention provides oligonucleotides that possess two or more regions of differing conformation, and at least one transitional nucleobase positioned between the regions that is capable of modulating transfer of the helical conformation characteristic of the region bound to the 3'hydroxy thereof, to the region bound to the 5' hydroxyl thereof.

21 Claims, No Drawings

(56) References Cited

OTHER PUBLICATIONS

Kawasaki et al., "Uniformly Modified 2'-Deoxy-2'-fluoro Phosphorothioate Oligonucleotides as Nuclease-Resistant Antisense Compounds with High Affinity and Specificity for RNA Targets" J. Med. Chem. (1993) 36:831-841.

Kumar et al., "The First Analogues of LNA (Locked Nucleic Acids): Phosphorothioate-LNA and 2'-ThioLNA" Bioorg. Med. Chem. Lett. (1998) 8:2219-2222.

Lima et al., "Binding Affinity and Specificity of *Escherichia coli* Rnase H1: Impact on the Kinetics of Catalysis of Antisense Oligonucleotide-RNA Hybrids" Biochemistry (1997) 36:390-398.

Lima et al., "Human Rnase H1 Uses One Tyrptophan and Two Lysines to Position the Enzyme at the 3'-DNA/5'-RNA Terminus of the Heteroduplex Substrate" J. Biol. Chem. (2003) 278(50):49860-49867.

Moran et al., "Difluorotoluene, a Nonpolar Isostere for Thymine, Codes Specifically and Efficiently for Adenine in DNA Replication" J. Am. Chem. Soc. (1997) 119:2056-2057.

Nielsen et al., "Sequence-Selective Recognition of DNA by Strand Displacement with a Thymine-Substituted Polyamide" Scence (1991) 254:1497-1500.

Parikh et al., "Uracil-DNA glycosylase—DNA substrate and product structures: Conformational strain promotes catalytic efficiency by coupled stereoelectronic effects " PNAS (2000) 10:5083-5088.

Renneberg et al., "Watson-Crick Base-Pairing Properties of Tricyclo-DNA" J. Am. Chem. Soc. (2002) 124:5993-6002.

Scaringe, "RNA Oligonucleotide Synthesis via 5'-Silyl-2'-Orthoester Chemistry" Methods (2001) 23:206-217.

Singh et al., "LNA (locked nucleic acids): synthesis and high-affinity nucleic acid recognition" Chem. Commun. (1998) 4:455-456.

Trapane et al., "DNA Triple Helixes with C-Nucleosides (Deoxypseudouridine) in the Second Strand" J. Am. Chem. Soc. (1994) 116:8412-8413.

Wang et al., "Cyclohexene Nucleic Acids (CeNA): Serum Stable Oligonucleotides that Activate RNase H and Increase Duplex Stability with Complementary RNA" J. Am. Chem. Soc. (2000) 122:8595-8602.

Wouters et al., "5'-Substituted Pyrimidine 1,5-Anhydrohexitols: Conformational Analysis and Interaction with Viral Thymidine Kinase" Bioorg. Med. Chem. Lett. (1999) 9:1563-1566.

Wu et al., "Molecular Cloning and Expression of cDNA for Human RNase H" Antisense Nucleic Acid Drug Discov. (1998) 8:53-61.

Wu et al., "Properties of Cloned and Expressed Human RNase H1" J. Biol. Chem. (1999) 274(40):28270-28278.

Wu et al., "Investigating the Structure of Human RNase H1 by Site-directed Mutagenesis" J. Biol. Chem. (2001) 276(26):23547-23553.

Zhu et al., "DNA duplexes flanked by hybrid duplexes: The solution structure of chimeric junctions in [r(cgcg)d(TATACGCG)]2" Biochemistry (1995) 34:2372-2380.

International Search Report for application PCT/US05/08428 dated Feb. 16, 2006.

European Search Report for application EP 05725530.9 dated Jan. 5, 2011.

* cited by examiner

SEQUENCE LISTING

```
<160> NUMBER OF SEQ ID NOS: 28

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1
ctacgctttc cacgcacagt                                           20

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 2
agtttaggtc tccgatcgtc                                           20

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 3
ctgctagcct ctggatttga                                           20

<210> SEQ ID NO 4
<211> LENGTH: 2160
<212> TYPE: DNA
<213> ORGANISM: Mus musculus

<400> SEQUENCE: 4
ggcgccctgc tctcccggcg gggcggcgga gggggcgggc tggccggcgc acggtgatgt      60
ggcgggactc tttgtgcact gcggcaggat acgcgcttgg gcgtcgggac gcggctgcgc     120
tcagctctct cctctcggaa gctgcagcca tgatggaagt ttgagagttg agccgctgtg     180
```

```
aggccaggcc cggcgcaggc gagggagatg agagacggcg gcggccacgg cccagagccc    240
ctctcagcgc ctgtgagcag ccgcggggc agcgccctcg gggagccggc cgggcggcgg      300
cggcggcagc ggcggcgggc ctcgcctcct cgtcgtctgt tctaaccggg cagcttctga    360
gcagcttcgg agagagacgg tggaagaagc cgtgggctcg agcggagcc ggcgcaggct      420 cggcggctgc acctcccgct cctggagcgg ggggagaag cggcggcggc ggccgcggct      480
ccggggaggg ggtcggagtc gcctgtcacc attgccaggg ctgggaacgc cggagagttg    540
ctctctcccc ttctcctgcc tccaacacgg cggcggcggc ggcggcacgt ccagggaccc    600
gggccggtgt taagcctccc gtccgccgcc gccgcaccc cctggcccg ggctccggag      660 gccgccggag gaggcagccg ctgcgaggat tatccgtctt ctccccattc cgctgcctcg    720
gctgccaggc ctctggctgc tgaggagaag caggcccagt ctctgcaacc atccagcagc    780
cgccgcagca gccattaccc ggctgcggtc cagggccaag cggcagcaga gcgaggggca    840
tcagcgaccg ccaagtccag agccatttcc atcctgcaga agaagcctcg ccaccagcag    900
cttctgccat ctctctcctc cttttcttc agccacaggc tcccagacat gacagccatc      960
atcaaagaga tcgttagcag aaacaaaagg agatatcaag aggatggatt cgacttagac    1020
ttgacctata tttatccaaa tattattgct atgggatttc ctgcagaaag acttgaaggt    1080
gtatacagga caatattga tgatgtagta aggttttgg attcaaagca taaaaaccat      1140
tacaagatat acaatctatg tgctgagaga cattatgaca ccgccaaatt taactgcaga    1200
gttgcacagt atccttttga agaccataac ccaccacagc tagaacttat caaacccttc    1260
tgtgaagatc ttgaccaatg gctaagtgaa gatgacaatc atgttgcagc aattcactgt    1320
aaagctggaa agggacggac tggtgtaatg atttgtgcat attattgca tcggggcaaa    1380 ttttttaaagg cacaagaggc cctagatttt tatggggaag taaggaccag agacaaaaag    1440
ggagtcacaa ttcccagtca gaggcgctat gtatattatt atagctacct gctaaaaaat    1500
cacctggatt acagacccgt ggcactgctg tttcacaaga tgatgtttga aactattcca    1560
atgttcagtg gcggaacttg caatcctcag tttgtggtct gccagctaaa ggtgaagata    1620
tattcctcca attcaggacc cacgcggcgg aggacaagt tcatgtactt tgagttccct     1680
cagccattgc ctgtgtgtgg tgatatcaaa gtagagttct tccacaaaca gaacaagatg    1740
ctcaaaaagg acaaaatgtt tcacttttgg gtaaatacgt tcttcatacc aggaccagag    1800
gaaacctcag aaaagtgga aatggaagt ctttgtgatc aggaaatcga tagcatttgc      1860
agtatagagc gtgcagataa tgacaaggag tatcttgtac tcaccctaac aaaaaacgat    1920
cttgacaaag caaacaaaga caaggccaac cgatacttct ctccaaattt taaggtgaaa    1980
ctatacttta caaaaacagt agaggagcca tcaaatccag aggctagcag ttcaacttct    2040
gtgactccag atgttagtga caatgaacct gatcattata gatattctga caccactgac    2100
tctgatccag agaatgaacc ttttgatgaa gatcagcatt cacaaattac aaaagtctga    2160
```

<210> SEQ ID NO 5
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 5
atgacaatca tgttgcagca attc                                            24

```
<210> SEQ ID NO 6
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 6
cgatgcaata aatatgcaca aatca                                         25

<210> SEQ ID NO 7
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 7
ctgtaaagct ggaaagggac ggactggt                                      28

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 8
ccttccctga aggttcctcc                                               20

<210> SEQ ID NO 9

<400> SEQUENCE: 9

000

<210> SEQ ID NO 10
<211> LENGTH: 12
<212> TYPE: RNA
<213> ORGANISM: Artificial Sequence
<220> FEATURE:
<223> OTHER INFORMATION: Synthetic oligonucleotide

<400> SEQUENCE: 10
cgcgaauucg cg                                                       12

<210> SEQ ID NO 11
<211> LENGTH: 12
<212> TYPE: RNA
<213> ORGANISM: Artificial Sequence
<220> FEATURE:
<223> OTHER INFORMATION: Synthetic oligonucleotide

<400> SEQUENCE: 11
gcgcuuaagc gc                                                       12

<210> SEQ ID NO 12
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 12
cgagaggcgg acgggaccg                                                19
```

```
<210> SEQ ID NO 13
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1-19
<223> OTHER INFORMATION: Bases at these positions are RNA

<400> SEQUENCE: 13
cgagaggcgg acgggaccgt t                                              21

<210> SEQ ID NO 14
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1-3, 5-8, 10-14, 16, 18, 19
<223> OTHER INFORMATION: Bases at these positions are RNA
<220> FEATURE:
<221> NAME/KEY: modified_base
<222> LOCATION: 1-3, 5-8, 10-14, 16, 18, 19
<223> OTHER INFORMATION: modified 2'position

<400> SEQUENCE: 14
cggtcccgtc cgcctctcgt t                                              21

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: 4
<223> OTHER INFORMATION: tetrafluoroindole

<400> SEQUENCE: 15
ctgctagcct ctggatttga                                                20

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: 5
<223> OTHER INFORMATION: tetrafluoroindole

<400> SEQUENCE: 16
ctgctagcct ctggatttga                                                20

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: 6
<223> OTHER INFORMATION: tetrafluoroindole
```

-continued

```
<400> SEQUENCE: 17
ctgctagcct ctggatttga                                                    20

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: 7
<223> OTHER INFORMATION: tetrafluoroindole

<400> SEQUENCE: 18
ctgctagcct ctggatttga                                                    20

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: 8
<223> OTHER INFORMATION: tetrafluoroindole

<400> SEQUENCE: 19
ctgctagcct ctggatttga                                                    20

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: 10
<223> OTHER INFORMATION: tetrafluoroindole

<400> SEQUENCE: 20
ctgctagcct ctggatttga                                                    20

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: 5
<223> OTHER INFORMATION: N-3-methyl-2'MOE-thymidine

<400> SEQUENCE: 21
ctgctagcct ctggatttga                                                    20

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: 17
```

```
<223> OTHER INFORMATION: tetrafluoroindole

<400> SEQUENCE: 22
ctgctagcct ctggatttga                                                    20

<210> SEQ ID NO 23
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: 16
<223> OTHER INFORMATION: tetrafluoroindole

<400> SEQUENCE: 23
ctgctagcct ctggatttga                                                    20

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: 15
<223> OTHER INFORMATION: tetrafluoroindole

<400> SEQUENCE: 24
ctgctagcct ctggatttga                                                    20

<210> SEQ ID NO 25
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: 14
<223> OTHER INFORMATION: tetrafluoroindole

<400> SEQUENCE: 25
ctgctagcct ctggatttga                                                    20

<210> SEQ ID NO 26
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: 13
<223> OTHER INFORMATION: tetrafluoroindole

<400> SEQUENCE: 26
ctgctagcct ctggatttga                                                    20

<210> SEQ ID NO 27
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
```

```
<222> LOCATION: 5, 15
<223> OTHER INFORMATION: tetrafluoroindole

<400> SEQUENCE: 27
ctgctagcct ctggatttga                                                    20

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: 16
<223> OTHER INFORMATION: N-3-methyl-2'MOE-thymidine

<400> SEQUENCE: 28
ctgctagcct ctggatttga                                                    20
```

US 8,790,919 B2

COMPOSITIONS AND METHODS FOR OPTIMIZING CLEAVAGE OF RNA BY RNASE H

CROSS REFERENCE TO RELATED APPLICATIONS

This application is the U.S. National Stage filing for International Application Ser. No. PCT/US2005/008428 filed Mar. 15, 2005, which claims priority to U.S. Provisional Patent Applications 60/553,646 filed Mar. 15, 2004, 60/567, 016 filed Apr. 29, 2004, 60/609,516 filed Sep. 13, 2004, each of which is incorporated herein by reference in its entirety.

SEQUENCE LISTING

A sequence listing is filed herewith in accordance with CFR 1.821 and is hereby incorporated by reference.

FIELD OF THE INVENTION

The present invention provides compositions and methods for the optimization of cleavage of RNA species by RNase H. In some embodiments, the invention provides oligonucleotides that possess two or more regions of differing conformation, and at least one transitional nucleobase positioned between the regions that is capable of modulating transfer of the helical conformation characteristic of the region bound to the 3'hydroxy thereof, to the region bound to the 5' hydroxyl thereof.

BACKGROUND OF THE INVENTION

RNase H hydrolyzes RNA in RNA-DNA hybrids. RNase H activity appears to be ubiquitous in eukaryotes and bacteria. Although RNases H constitute a family of proteins of varying molecular weight, the nucleolytic activity and substrate requirements appear to be similar for the various isotypes. For example, all RNases H studied to date function as endonucleases exhibiting limited sequence specificity and requiring divalent cations (e.g., $Mg^{2+}$, $Mn^{2+}$) to produce cleavage products with 5'-phosphate and 3'-hydroxyl termini.

Recently, two human RNase H genes have been cloned and expressed. RNase H1 is a 286 amino acid protein and is expressed ubiquitously in human cells and tissues. The amino acid sequence of human RNase H1 displays strong homology with RNase H1 from yeast, chicken, E. coli and mouse. Human RNase H2 shares strong amino acid sequence homology with RNase H2 from C. elegans, yeast and E. coli. Although the biological roles for the human enzymes are not fully understood, RNase H2 appears to be involved in de novo DNA replication and RNase H1 has been shown in mice to be important for mitochondrial DNA replication.

The structure of human RNase H1 was shown to consist of a 73 amino acid region homologous with the RNA-binding domain of yeast RNase H1 at the amino-terminus of the protein and separated from the catalytic domain by a 62 amino acid spacer region. The catalytic domain is highly conserved with the amino acid sequences of other RNase H1 proteins and contains the key catalytic and substrate binding residues required for activity. Site-directed mutagenesis of human RNase H1 revealed that the spacer region was required for RNase H activity. Although the RNA-binding domain was shown not to be required for RNase H activity, this region was responsible for the enhanced binding affinity of the human enzyme for the heteroduplex substrate as well as the strong positional preference for cleavage exhibited by the enzyme.

The RNA-binding domain of human RNase H1 is conserved in other eukaryotic RNases H1 and the highly conserved lysines at positions 59 and 60 of human RNase H1 have been shown to be important for binding to the heteroduplex substrate. The conserved tryptophan at position 43 was responsible for properly positioning the enzyme on the substrate for catalysis.

Human RNase H1 exhibits a strong positional preference for cleavage, i.e., human RNase H1 cleaves the heteroduplex substrate between 7 to 12 nucleotides from the 5'-RNA/3'-DNA terminus. Based on site-directed mutagenesis of both human RNase H1 and the heteroduplex substrate, the RNA-binding domain was shown to be responsible for the observed positional preference for cleavage. The RNA-binding domain of human RNase H1 appeared to bind to the 3'-DNA/5'-RNA pole of the heteroduplex substrate with the catalytic site of the enzyme positioned slightly less than one helical turn from the RNA-binding domain. Substitution of either the terminal 3'-DNA with a single ribonucleotide or 5'-RNA with a 2'-methoxyethoxy deoxyribonucleotide was shown to cause a concomitant 3'-shift of the first 5'-cleavage site on the RNA, suggesting that altering duplex geometry interferes with proper positioning of the enzyme on the heteroduplex for cleavage. Although the interaction between the RNA-binding domain and the heteroduplex substrate has been characterized, the mechanism by which the catalytic domain of RNase H1 recognizes the substrate has not been fully elucidated.

Human RNase H1 is a nuclease that cleaves RNA exclusively in an RNA/DNA duplex via a double-strand DNase cleavage mechanism. Neither double-strand RNA (dsRNA) or DNA (dsDNA) duplexes support RNase H1 activity. The observed structural differences between the RNA/DNA heteroduplex and dsRNA and dsDNA duplexes suggest a possible role for the helical geometry and the sugar conformation of the DNA and RNA in the selective cleavage of the heteroduplex substrate by human RNase H1. Specifically, the deoxyribonucleotides within dsDNA form a southern $C_{2'}$-endo sugar conformation resulting in a B-form helical conformation, whereas ribonucleotides within dsRNA form a northern $C_{3'}$-endo pucker and an A-form helical geometry. In contrast, the deoxyribonucleotides of the RNA/DNA heteroduplex have been shown to adopt an eastern $O_{4'}$-endo sugar pucker resulting in a helical conformation where the RNA strand adopts A-form geometry and the DNA strand shares both the A- and B-form helical conformations. The conformational diversity observed for the DNA strand is likely a function of the intrinsic flexibility of the deoxyribonucleotide compared to RNA, and may also be important for human RNase H1 activity. DNA also differs from RNA in that the furanose ring of deoxynucleotide is much more flexible, i.e., exhibit a nearly symmetrical potential energy barrier for both south and north sugar conformations.

Consistent with these observations, heteroduplexes containing 2'-ara-fluoro deoxyribonucleotides, which have been shown to exhibit a sugar conformation comparable to DNA when hybridized to RNA, have also been shown to support RNase H1 activity. On the other hand, heteroduplexes consisting of RNA/2'-alkoxy modified deoxyribonucleotides, exhibiting $C_{3'}$-endo sugar pucker and an A-form helical geometry when hybridized to RNA do not support human RNase H1 activity. It has previously been shown that both E. coli and human RNases H1 bind A-form duplexes (e.g., RNA/ RNA, 2'-methoxyethoxy/RNA and 2'-methoxy/RNA) with comparable affinity to the DNA/RNA heteroduplex substrate but do not cleave the A-form duplexes. In this case, the size and position of the 2'-substituents of RNA and 2'-alkoxy nucleotides suggest possible steric interference with RNase H1 as the 2'-substituents are positioned within the minor groove of the heteroduplex; a region predicted to be the binding site for the enzyme. Alternatively, the sugar conformation and flexibility map play a decisive role in RNase H1 activity.

It can be seen that optimizing the cleavage of RNase H targets would be of great benefit. This invention is directed to this, as well as other, important ends.

SUMMARY OF THE INVENTION

In some embodiments, the invention provides methods of modulating the concentration of a targeted RNA molecule in a eukaryotic cell comprising the step of contacting said cell with an oligonucleotide having:

a) a first region of nucleotides of one conformation which, when bound to said targeted RNA, forms a substrate for cleavage by an RNase;

b) a second region of nucleotides having a different conformation which, when bound to said targeted RNA molecule does not form a substrate for cleavage by an RNase, and c) a transition moiety which modulates the transmission of the conformation of said second region into said first region.

In one embodiment of the invention the second region is positioned 5' to the first region. In other embodiments, the oligonucleotide further comprises a third region of nucleotides having a conformation different than the conformation of said first region, said third region when bound to said targeted RNA molecule does not form a substrate for cleavage by an RNase. In yet other embodiments the third region of nucleotides has a conformation different than the conformation of said first region, said third region is positioned 3' to said first region and when bound to said targeted RNA molecule does not form a substrate for cleavage by an RNase. In another embodiment, the third region has the same conformation as the second region.

In another embodiment of the invention the first region comprises deoxynucleotides. In other embodiments, the second region comprises 2'-O-alkoxyalkyl ribonucleotides, where preferably the 2'-O-alkoxyalkyl ribonucleotides are 2'-O-methoxyethyl ribonucleotides. In some aspects of the invention the internucleotide linkages in the first or second regions are phosphorothioates.

In other embodiments the transition moiety is positioned between said first and said second regions and is a region of 2-10 nucleotides comprising at least one modified nucleotide, or flexible hydrocarbon internucleotide linker. In another embodiment of the invention the modified nucleotide is selected from a modified base nucleotide, a modified sugar nucleotide, a modified or unmodified sugar abasic nucleotide, a THF nucleotide, or an acyclic nucleotide. In further embodiments the modified base nucleotide comprises a modified base moiety which does not form hydrogen bonds with the bases of the targeted RNA molecule and can optionally π stack with adjacent bases. In yet other embodiments, the modified base moiety is a universal base, a promiscuous base, a size expanded base or a fluorinated base. In some preferred embodiments, the modified base moiety is tetrafluoroindolyl or a moiety selected from formulas I, II, II, IV, V, VI, VII, VIII, or IX. In other embodiments, the modified sugar nucleotide is a 2'-ara-modified nucleotide, preferably the 2'-ara-modified nucleotide is a 2'-ara-fluoro nucleotide. In other embodiments, the flexible hydrocarbon internucleotide linker is $C_3$-$C_6$ alkylene. In another embodiment of the invention the eukaryotic cell is present in an animal.

In some embodiments, the invention provides compounds of the Formula:

$$(T_2)_j\text{-}(T_3)_k\text{-}(T_1)_m\text{-}(T_4)_n\text{-}(T_1)_p\text{-}(T_5)_q\text{-}(T_2)_r$$

wherein
each $T_1$ is a 2'-deoxyribonucleotide;
each $T_2$ is a nucleotide having a higher binding affinity for a RNA target as compared to the binding affinity of a 2'-deoxyribonucleotide for said RNA target;
each $T_3$, $T_4$ and $T_5$ are transition moieties;
j and r independently are 0 to 10, and together the sum of j and r is at least 2;
m and p independently are 1 to 20, and together the sum of m and p is at least 5;
k, n and q independently are 0 to 3, and together the sum of k, n and q is at least 1.

In some embodiments, $T_2$ comprises a nucleotide having a northern conformation. In some such embodiments, $T_2$ comprises a nucleotide having a 2'-modification. In some further embodiments, the 2'-modification is hydroxyl, —O-alkyl, —O-alkyl-O-alkyl, S-alkyl, S-alkyl-O-alkyl, —F, —O—$CH_2CH_2$—O—$CH_3$, —O—$CH_3$, —O—$CH_2$—CH=$CH_2$ or a group having one of formula $I_a$ or $II_a$:

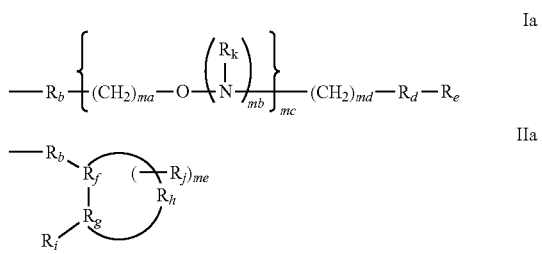

wherein:
$R_b$ is O, S or NH;
$R_d$ is a single bond, O, S or C(=O);
$R_e$ is $C_1$-$C_{10}$ alkyl, N($R_k$)($R_m$), N($R_k$)($R_n$), N=C($R_p$)($R_q$), N=C($R_p$)($R_r$) or has formula $III_a$;

$R_p$ and $R_q$ are each independently hydrogen or $C_1$-$C_{10}$ alkyl;
$R_r$ is —$R_x$-$R_y$;
each $R_s$, $R_t$, $R_u$ and $R_v$ is, independently, hydrogen, C(O)$R_w$, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, alkylsulfonyl, arylsulfonyl, a chemical functional group or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl;
or optionally, $R_u$ and $R_v$, together form a phthalimido moiety with the nitrogen atom to which they are attached;
each $R_w$ is, independently, substituted or unsubstituted $C_1$-$C_{10}$ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, isobutyryl, phenyl or aryl;
$R_k$ is hydrogen, a nitrogen protecting group or —$R_x$—$R_y$;
$R_p$ is hydrogen, a nitrogen protecting group or —$R_x$—$R_y$;

$R_x$ is a bond or a linking moiety;

$R_y$ is a chemical functional group, a conjugate group or a solid support medium;

each $R_m$ and $R_n$ is, independently, H, a nitrogen protecting group, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, wherein the substituent groups are selected from hydroxyl, amino, alkoxy, carboxy, benzyl, phenyl, nitro, thiol, thioalkoxy, halogen, alkyl, aryl, alkenyl, alkynyl; $NH_3^+$, $N(R_u)(R_v)$, guanidino and acyl where said acyl is an acid amide or an ester;

or $R_m$ and $R_n$, together, are a nitrogen protecting group, are joined in a ring structure that optionally includes an additional heteroatom selected from N and O or are a chemical functional group;

$R_i$ is $OR_z$, $SR_z$, or $N(R_z)_2$;

each $R_z$ is, independently, H, $C_1$-$C_8$ alkyl, $C_1$-$C_8$ haloalkyl, C(=NH)N(H)$R_u$, C(=O)N(H)$R_u$ or OC(=O)N(H)$R_u$;

$R_f$, $R_g$ and $R_h$ comprise a ring system having from about 4 to about 7 carbon atoms or having from about 3 to about 6 carbon atoms and 1 or 2 heteroatoms wherein said heteroatoms are selected from oxygen, nitrogen and sulfur and wherein said ring system is aliphatic, unsaturated aliphatic, aromatic, or saturated or unsaturated heterocyclic;

$R_j$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(R_k)(R_m)$ $OR_k$, halo, $SR_k$ or CN;

$m_a$ is 1 to about 10;

each mb is, independently, 0 or 1;

mc is 0 or an integer from 1 to 10;

md is an integer from 1 to 10;

me is from 0, 1 or 2; and provided that when mc is 0, md is greater than 1.

In some embodiments, each of j and r are at least 2. In some further embodiments, $T_3$, $T_4$ and $T_5$ each comprise a nucleotide having one of an eastern or southern conformation. In some embodiments, at least one of $T_3$, $T_4$ and $T_5$ comprise a 2'-fluoro-arabinonucleotide. In some embodiments, each of $T_3$, $T_4$ and $T_5$ comprise a 2'-fluoro-arabinonucleotide.

In some embodiments, each of n and p are 0.

In some embodiments, each $T_2$ comprises a nucleotide having a 2'-modification;

each of j and r are at least 2; and $T_3$, $T_4$ and $T_5$ each comprise a nucleotide having one of an eastern or southern conformation. In some such embodiments, $T_3$, $T_4$ and $T_5$ each comprise a nucleotide having an eastern conformation. In some embodiments, at least one of $T_3$, $T_4$ and $T_5$ comprise a 2'-fluoro-arabinonucleotide, an abasic nucleotide, a THF nucleoside, or a nucleotide having a nucleobase selected from Formulas I, II, and III:

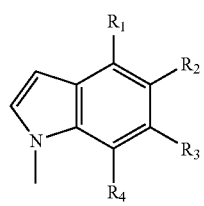

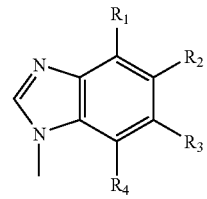

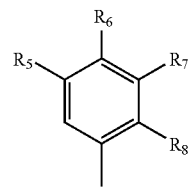

wherein:

each of $R_{1-8}$ is independently selected from H, halogen and $C_{1-3}$ alkyl. In some embodiments, $R_{1-8}$ is independently selected from fluorine and methyl. In some embodiments, nucleobase is selected from Formulas IV, V or VI:

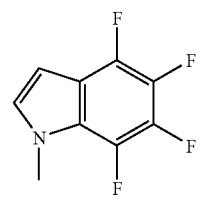

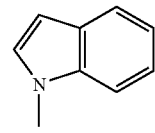

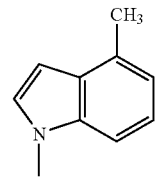

or Formulas VII, VIII, IX, X or XI:

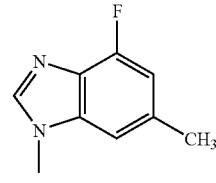

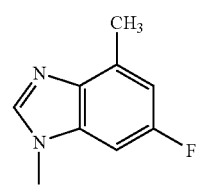

-continued

IX

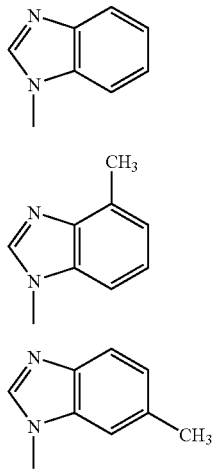

or Formulas XII or XIII:

XII

XIII

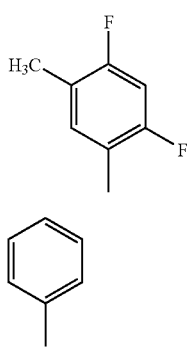

In some embodiments, j and r are each from 2 to 5, and m is 10 to 16. In some embodiments, j is 2, r is 2 and m is 14-18. In some embodiments, j is 2, r is 2 and m is 16. In some embodiments, j is 4, r is 4 and m is 10-14. In some embodiments, j is 4, r is 4 and m is 12. In some embodiments, j is 5, r is 5 and m is 8-12. In some embodiments, j is 5, r is 5 and m is 10.

In some embodiments, the invention provides methods of increasing one of the rate of cleavage or the position of cleavage of a target RNA by RNase H comprising:

selecting an oligonucleotide having an RNase H cleaving region and a non-RNase H cleaving region;

selecting a transition moiety capable of modulating transfer of the helical conformation characteristic of an oligonucleotide bound to its 3'hydroxy to an oligonucleotide bound to its 5' hydroxyl;

interspacing said transition moiety in said oligonucleotide positioned between said RNase H cleaving region and said non-RNase H cleaving region; and binding said oligonucleotide to said target RNA in the presence of RNase H.

In some embodiments, the oligonucleotide has the Formula:

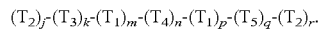

In some embodiments, the transition moiety bears a nucleobase having one of the structures IV-XIII, supra.

In some embodiments, the transition moiety has the Formula Z:

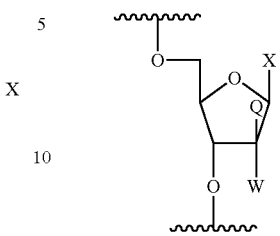

wherein:
X is selected from hydrogen, substituted or unsubstituted indolyl, substituted or unsubstituted benzimidazolyl, substituted or unsubstituted purinyl, or substituted or unsubstituted pyrimidinyl;
Q is selected from hydrogen or halogen;
W is selected from hydrogen or a 2'-substituent.

In some embodiments, the transition moiety is a 2'-fluoro-arabinonucleotide.

In some embodiments, the invention provides antisense oligonucleotides, comprising:
at least 2 conformationally different regions with a junction between each of said conformationally different regions, wherein each junction comprises at least one transition moiety capable of modulating transfer of the helical conformation characteristic of an oligonucleotide bound to its 3'hydroxy to an oligonucleotide bound to its 5' hydroxyl.

In some embodiments, the conformationally different regions each comprise at least two nucleotides. In further embodiments, the nucleotides of each conformationally different region each possess the same type of sugar conformation. In some embodiments, the type of sugar conformation is selected from Eastern, Northern and Southern.

In some embodiments, the transition moiety is a base-modified nucleotide or a sugar-modified nucleotide.

In some embodiments, base-modified nucleotide has the Formula Z.

In some embodiments, the 2'-substituent is a substituted or unsubstituted aliphatic ether.

In some embodiments, X is selected from Formulas I-XIII. In some such embodiments, W is H, and Q is F.

Also provided are methods of inhibiting gene expression, comprising contacting one or more cells, a tissue or an animal with one or more compositions of the invention.

The following applications are incorporated herein by reference, each in their entirety: 60/553,646 filed Mar. 15, 2004; 60/567,016 filed Apr. 29, 2004; and 60/609,516 filed Sep. 13, 2004.

DETAILED DESCRIPTION OF THE INVENTION

The present invention provides compounds and methods for the optimization of cleavage of RNA targets by RNAse H. By determining the structure activity relationships for the interaction between the catalytic domain of human RNase H1 and the RNA/DNA heteroduplex substrate by systematically evaluating the influence of sugar conformation, it has been discovered that nucleotides minimizing bulk in the minor groove and flexibility in the catalytic area are beneficial to enzyme efficiency. Modified nucleotides were introduced into the oligodeoxyribonucleotides at the human RNase H1 preferred cleavage sites on the heteroduplex and consisted of the DNA-like southern $C_2$-endo, RNA-like northern $C_3$-endo and eastern $O_{4'}$-endo biased sugars with and without 2'-substituents (FIG. 1A). In addition, varying degrees of conformational flexibility were introduced into the heteroduplex substrate by incorporating modified deoxyribonucleotides that Π-stack with the adjacent deoxyribonucleotides but do not form hydrogen bonds with the bases of the RNA strand, abasic deoxynucleotides, hydrocarbon intranucleotide linkers and the ganciclovir modified deoxyribonucleotide (FIG. 1B). The initial cleavage rates ($V_O$) as well as site-specific cleavage rates for the modified heteroduplexes were compared with the wild type DNA/RNA heteroduplex.

It has been discovered in accordance with the present invention that the incorporation of one or more transition moietys in an antisense oligonucleotide can optimize the rate of cleavage of the duplex formed between the RNA target and the antisense oligonucleotide. In some embodiments, the transition moietys are interspersed at the junction between regions of the antisense oligonucleotide that possess different conformation. While not wishing to be bound by a particular theory, it is believed that optimizing the helical geometry of the heteroduplex for RNase H1 cleavage can be accomplished by interspersing one or more transition moietys at the junction of regions of different conformation in an antisense oligonucleotide. For example, in accordance with some embodiments of the invention, a gapmer having a plurality of regions of at least two differing conformation types can have one or more transition moietys positioned at the junction of the regions.

In some embodiments, the nucleotides of the "wing" regions of the gapmer can have A form geometry (e.g., northern conformation). Examples of such nucleotides are those having 2'-modifications, for example 2'-MOE. In some embodiments, the "gap" regions have H-form geometry, for example DNA nucleotides. Generally, the transition moiety or nucleotides will be present at the junction of the regions, so as to impart a transition between the two regions of differing conformation.

In some embodiments, it is beneficial to minimize the lengths of the "wings" of the gapmer, and/or to further substitute 2'-substituted (e.g. MOE) nucleotides with one or more additional nuclease resistant modifications (e.g., methylphosphonate, phosphonoacetate, dangling steric blockers, etc.). In some embodiments, it also is beneficial to optimize helical conformation for cleavage, for example by use of, inter alia, norm-canonical base pairs.

Because the catalytic site of bound RNase H1 is located about one full helical turn from the RNA binding site, in some embodiments, it is beneficial to have at least one transition moiety located 5 to 10 nucleobases from the 3'-terminus of the antisense oligonucleotide, or 6 to 9 nucleobases from the 3'-terminus of the antisense oligonucleotide, or 7 to 8 nucleobases from the 3'-terminus of the antisense oligonucleotide. In addition to the benefit of altering the helical geometry and eliminate bulk in the minor groove, it is believed that the transitional nucleobases can correct conformational transmission from one conformational region to the next.

As used herein, the term transition moiety (or "flexible nucleotide") is intended to mean a nucleotide that capable of modulating transfer of the helical conformation characteristic of an oligonucleotide bound to its 3'hydroxy to an oligonucleotide bound to its 5' hydroxyl, when the oligonucleotide is in a duplex with RNA.

Examples of such transition moietys include those that having one of an eastern or southern conformation, 2'-fluoroarabinonucleotide, abasic nucleotides, and THF nucleosides. Further examples include nucleotides having a nucleobase selected from Formulas I, II, and III:

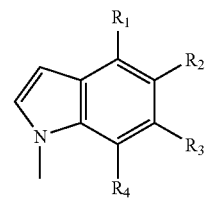

I

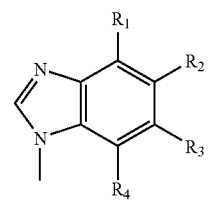

II

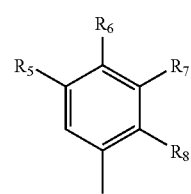

III wherein:

each of $R_{1-8}$ is independently selected from H, halogen and $C_{1-3}$ alkyl. In some embodiments, $R_{1-8}$ is independently selected from fluorine and methyl. In some embodiments, nucleobase is selected from Formulas IV, V or VI:

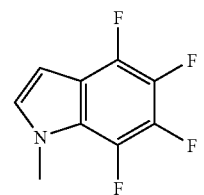

IV

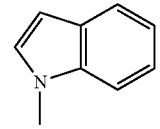

V

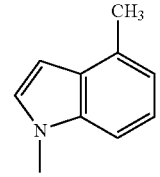

VI or Formulas VII, VIII, IX, X or XI:

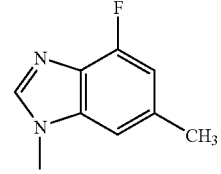

VII

-continued

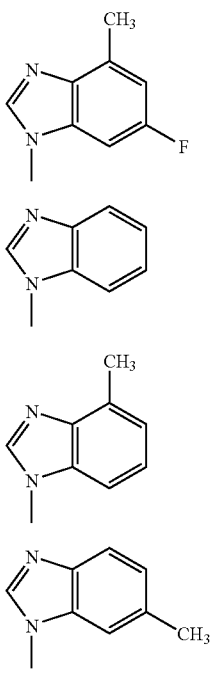

or Formulas XII or XIII:

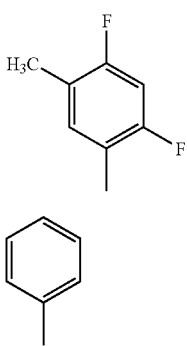

In some embodiments, the invention provides compounds of the Formula:

$(T_2)_j-(T_3)_k-(T_1)_m-(T_4)_n-(T_1)_p-(T_5)_q-(T_2)_r$ wherein
each $T_1$ is a 2'-deoxyribonucleotide;
each $T_2$ is a nucleotide having a higher binding affinity for a RNA target as compared to the binding affinity of a 2'-deoxyribonucleotide for said RNA target;
each $T_3$, $T_4$ and $T_5$ are transition moietys;
j and r independently are 0 to 10, and together the sum of j and r is at least 2;
m and p independently are 1 to 20, and together the sum of m and p is at least 5;
k, n and q independently are 0 to 3, and together the sum of k, n and q is at least 1.

In some embodiments, $T_2$ comprises a nucleotide having a northern conformation.

In some such embodiments, $T_2$ comprises a nucleotide having a 2'-modification.

In some embodiments, j and r are each from 2 to 5, and m is 10 to 16. In some embodiments, j is 2, r is 2 and m is 14-18. In some embodiments, j is 2, r is 2 and m is 16. In some embodiments, j is 4, r is 4 and m is 10-14. In some embodiments, j is 4, r is 4 and m is 12. In some embodiments, j is 5, r is 5 and m is 8-12. In some embodiments, j is 5, r is 5 and m is 10.

In some embodiments, the invention provides methods of increasing one of the rate of cleavage or the position of cleavage of a target RNA by RNase H comprising:
selecting an oligonucleotide having an RNase H cleaving region and a non-RNase H cleaving region;
selecting a transition moiety capable of modulating transfer of the helical conformation characteristic of an oligonucleotide bound to its 3'hydroxy to an oligonucleotide bound to its 5' hydroxyl;
interspacing said transition moiety in said oligonucleotide positioned between said RNase H cleaving region and said non-RNase H cleaving region; and
binding said oligonucleotide to said target RNA in the presence of RNase H.

In some embodiments, the oligonucleotide has the Formula:

$(T_2)_j-(T_3)_k-(T_1)_m-(T_4)_n-(T_1)_p-(T_5)_q-(T_2)_r$.

In some embodiments, the transition moiety bears a nucleobase having one of the structures IV-XIII, supra.

Compounds of the present invention will be useful for the modulation of gene expression. In one aspect of the present invention a targeted cell, group of cells, a tissue or an animal is contacted with a composition of the invention to effect reduction of message that can directly inhibit gene expression. In another embodiment the reduction of message indirectly upregulates a non-targeted gene through a pathway that relates the targeted gene to a non-targeted gene. Methods and models for the regulation of genes using oligomeric compounds of the invention are illustrated in the examples.

In another aspect a method of inhibiting gene expression is disclosed comprising contacting one or more cells, a tissue or an animal with a compound of the invention.

Compositions of the invention modulate gene expression by hybridizing to a nucleic acid target resulting in loss of its normal function. As used herein, the term "target nucleic acid" or "nucleic acid target" is used for convenience to encompass any nucleic acid capable of being targeted including without limitation DNA, RNA (including pre-mRNA and mRNA or portions thereof) transcribed from such DNA, and also cDNA derived from such RNA. In a preferred embodiment of the invention the target nucleic acid is a messenger RNA. In a further preferred embodiment the degradation of the targeted messenger RNA is facilitated by a RISC complex that is formed with oligomeric compounds of the invention. In another preferred embodiment the degradation of the targeted messenger RNA is facilitated by a nuclease such as RNaseH.

The hybridization of an oligomeric compound of this invention with its target nucleic acid is generally referred to as "antisense". Consequently, the preferred mechanism in the practice of some preferred embodiments of the invention is referred to herein as "antisense inhibition." Such antisense inhibition is typically based upon hydrogen bonding-based hybridization of oligonucleotide strands or segments such that at least one strand or segment is cleaved, degraded, or otherwise rendered inoperable. In this regard, it is presently preferred to target specific nucleic acid molecules and their functions for such antisense inhibition.

The functions of DNA to be interfered with can include replication and transcription. Replication and transcription, for example, can be from an endogenous cellular template, a vector, a plasmid construct or otherwise. The functions of RNA to be interfered with can include functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA. In the context of the present invention, "modulation" and "modulation of expression" mean either an increase (stimulation) or a decrease (inhibition) in the amount or levels of a nucleic acid molecule encoding the gene, e.g., DNA or RNA. Inhibition is often the preferred form of modulation of expression and mRNA is often a preferred target nucleic acid.

The compositions and methods of the present invention are also useful in the study, characterization, validation and modulation of small non-coding RNAs. These include, but are not limited to, microRNAs (miRNA), small nuclear RNAs (snRNA), small nucleolar RNAs (snoRNA), small temporal RNAs (stRNA) and tiny non-coding RNAs (tncRNA) or their precursors or processed transcripts or their association with other cellular components.

Small non-coding RNAs have been shown to function in various developmental and regulatory pathways in a wide range of organisms, including plants, nematodes and mammals. MicroRNAs are small non-coding RNAs that are processed from larger precursors by enzymatic cleavage and inhibit translation of mRNAs. stRNAs, while processed from precursors much like miRNAs, have been shown to be involved in developmental timing regulation. Other non-coding small RNAs are involved in events as diverse as cellular splicing of transcripts, translation, transport, and chromosome organization.

As modulators of small non-coding RNA function, the compositions of the present invention find utility in the control and manipulation of cellular functions or processes such as regulation of splicing, chromosome packaging or methylation, control of developmental timing events, increase or decrease of target RNA expression levels depending on the timing of delivery into the specific biological pathway and translational or transcriptional control. In addition, the compositions of the present invention can be modified in order to optimize their effects in certain cellular compartments, such as the cytoplasm, nucleus, nucleolus or mitochondria.

The compositions of the present invention can further be used to identify components of regulatory pathways of RNA processing or metabolism as well as in screening assays or devices.

Oligomeric Compounds

In the context of the present invention, the term "oligomeric compound" refers to a polymeric structure capable of hybridizing a region of a nucleic acid molecule. This term includes oligonucleotides, oligonucleosides, oligonucleotide analogs, oligonucleotide mimetics and combinations of these. Oligomeric compounds are routinely prepared linearly but can be joined or otherwise prepared to be circular and may also include branching. Oligomeric compounds can included double stranded constructs such as for example two strands hybridized to form double stranded compounds. The double stranded compounds can be linked or separate and can include overhangs on the ends. In general an oligomeric compound comprises a backbone of linked momeric subunits where each linked momeric subunit is directly or indirectly attached to a heterocyclic base moiety. Oligomeric compounds may also include monomeric subunits that are not linked to a heterocyclic base moiety thereby providing abasic sites. The linkages joining the monomeric subunits, the sugar moieties or surrogates and the heterocyclic base moieties can be independently modified giving rise to a plurality of motifs for the resulting oligomeric compounds including hemimers, gapmers and chimeras.

As is known in the art, a nucleoside is a base-sugar combination. The base portion of the nucleoside is normally a heterocyclic base moiety. The two most common classes of such heterocyclic bases are purines and pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. The respective ends of this linear polymeric structure can be joined to form a circular structure by hybridization or by formation of a covalent bond, however, open linear structures are generally preferred. Within the oligonucleotide structure, the phosphate groups are commonly referred to as forming the internucleoside linkages of the oligonucleotide. The normal internucleoside linkage of RNA and DNA is a 3' to 5' phosphodiester linkage.

In the context of this invention, the term "oligonucleotide" refers to an oligomer or polymer of ribonucleic acid (RNA) or deoxyribonucleic acid (DNA). This term includes oligonucleotides composed of naturally-occurring nucleobases, sugars and covalent internucleoside linkages. The term "oligonucleotide analog" refers to oligonucleotides that have one or more non-naturally occurring portions which function in a similar manner to oligonucleotides. Such non-naturally occurring oligonucleotides are often preferred the naturally occurring forms because of desirable properties such as, for example, enhanced cellular uptake, enhanced affinity for nucleic acid target and increased stability in the presence of nucleuses.

In the context of this invention, the term "oligonucleoside" refers to a sequence of nucleosides that are joined by internucleoside linkages that do not have phosphorus atoms. Internucleoside linkages of this type include short chain alkyl, cycloalkyl, mixed heteroatom alkyl, mixed heteroatom cycloalkyl, one or more short chain heteroatomic and one or more short chain heterocyclic. These internucleoside linkages include but are not limited to siloxane, sulfide, sulfoxide, sulfone, acetyl, formacetyl, thioformacetyl, methylene formacetyl, thioformacetyl, alkeneyl, sulfamate; methyleneimino, methylenehydrazino, sulfonate, sulfonamide, amide and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

Further included in the present invention are oligomeric compounds such as antisense oligomeric compounds, antisense oligonucleotides, ribozymes, external guide sequence (EGS) oligonucleotides, alternate splicers, primers, probes, and other oligomeric compounds which hybridize to at least a portion of the target nucleic acid. As such, these oligomeric compounds may be introduced in the form of single-stranded, double-stranded, circular or hairpin oligomeric compounds and may contain structural elements such as internal or terminal bulges or loops. Once introduced to a system, the oligomeric compounds of the invention may elicit the action of one or more enzymes or structural proteins to effect modification of the target nucleic acid.

One non-limiting example of such an enzyme is RNAse H, a cellular endonuclease which cleaves the RNA strand of an RNA:DNA duplex. It is known in the art that single-stranded antisense oligomeric compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While the preferred form of antisense oligomeric compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

In addition to the modifications described above, the nucleosides of the oligomeric compounds of the invention can have a variety of other modification so long as these other modifications either alone or in combination with other nucleosides enhance one or more of the desired properties described above. Thus, for nucleotides that are incorporated into oligonucleotides of the invention, these nucleotides can have sugar portions that correspond to naturally-occurring sugars or modified sugars. Representative modified sugars include carbocyclic or acyclic sugars, sugars having substituent groups at one or more of their 2', 3' or 4' positions and sugars having substituents in place of one or more hydrogen atoms of the sugar. Additional nucleosides amenable to the present invention having altered base moieties and or altered sugar moieties are disclosed in U.S. Pat. No. 3,687,808 and PCT application PCT/US89/02323.

Altered base moieties or altered sugar moieties also include other modifications consistent with the spirit of this invention. Such oligonucleotides are best described as being structurally distinguishable from, yet functionally interchangeable with, naturally occurring or synthetic wild type oligonucleotides. All such oligonucleotides are comprehended by this invention so long as they function effectively to mimic the structure of a desired RNA or DNA strand. A class of representative base modifications include tricyclic cytosine analog, termed "G clamp" (Lin, et al, *J. Am. Chem. Soc.* 1998, 120, 8531). This analog makes four hydrogen bonds to a complementary guanine (G) within a helix by simultaneously recognizing the Watson-Crick and Hoogsteen faces of the targeted G. This G clamp modification when incorporated into phosphorothioate oligonucleotides, dramatically enhances antisense potencies in cell culture. The oligonucleotides of the invention also can include phenoxazine-substituted bases of the type disclosed by Flanagan, et al., *Nat. Biotechnol.* 1999, 17(1), 48-52.

The oligomeric compounds in accordance with this invention preferably comprise from about 8 to about 80 nucleobases (i.e. from about 8 to about 80 linked nucleosides). One of ordinary skill in the art will appreciate that the invention embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases in length.

In one preferred embodiment, the oligomeric compounds of the invention are 12 to 50 nucleobases in length. One having ordinary skill in the art will appreciate that this embodies oligomeric compounds of 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases in length.

In another preferred embodiment, the oligomeric compounds of the invention are 15 to 30 nucleobases in length. One having ordinary skill in the art will appreciate that this embodies oligomeric compounds of 15, 16, 17, 18, 19, 20, 21, 22, 23, 24, 25, 26, 27, 28, 29, or 30 nucleobases in length.

Particularly preferred oligomeric compounds are oligonucleotides from about 12 to about 50 nucleobases, even more preferably those comprising from about 15 to about 30 nucleobases.

Oligomeric compounds used in the compositions of the present invention can also be modified to have one or more stabilizing groups that are generally attached to one or both termini of oligomeric compounds to enhance properties such as for example nuclease stability. Included in stabilizing groups are cap structures. By "cap structure or terminal cap moiety" is meant chemical modifications, which have been incorporated at either terminus of oligonucleotides (see for example Wincott et al., WO 97/26270, incorporated by reference herein). These terminal modifications protect the oligomeric compounds having terminal nucleic acid molecules from exonuclease degradation, and can help in delivery and/or localization within a cell. The cap can be present at the 5'-terminus (5'-cap) or at the 3'-terminus (3'-cap) or can be present on both termini. In non-limiting examples, the 5'-cap includes inverted abasic residue (moiety), 4',5'-methylene nucleotide; 1-(beta-D-erythrofuranosyl) nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (for more details see Wincott et al., International PCT publication No. WO 97/26270, incorporated by reference herein).

Particularly preferred 3'-cap structures of the present invention include, for example 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Tyer, 1993, Tetrahedron 49, 1925; incorporated by reference herein).

Oligomer and Monomer Modifications

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally preferred. In addition, linear compounds may have internal nucleobase complementarity and may therefore fold in a manner as to produce a fully or partially double-stranded compound. Within oligonucleotides, the phosphate groups are commonly referred to as forming the internucleoside linkage or in conjunction with the sugar ring the backbone of the oligonucleotide. The normal internucleoside linkage that makes up the backbone of RNA and DNA is a 3' to 5' phosphodiester linkage.

Chimeric Oligomeric Compounds

It is not necessary for all positions in a oligomeric compound to be uniformly modified, and in fact more than one of the aforementioned modifications may be incorporated in a single oligomeric compound or even at a single monomeric subunit such as a nucleoside within a oligomeric compound. The present invention also includes oligomeric compounds which are chimeric oligomeric compounds. "Chimeric" oligomeric compounds or "chimeras," in the context of this invention, are oligomeric compounds containing two or more chemically distinct regions, each made up of at least one monomer unit, i.e., a nucleotide in the case of a nucleic acid based oligomer.

Chimeric oligomeric compounds typically contain at least one region modified so as to confer increased resistance to nuclease degradation, increased cellular uptake, and/or increased binding affinity for the target nucleic acid. An additional region of the oligomeric compound may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of inhibition of gene expression. Consequently, comparable results can often be obtained with shorter oligomeric compounds when chimeras are used, compared to for example phosphorothioate deoxyoligonucleotides hybridizing to the same target region. Cleavage of the RNA target can be routinely detected by gel electrophoresis and, if necessary, associated nucleic acid hybridization techniques known in the art.

Chimeric oligomeric compounds of the invention may be formed as composite structures of two or more oligonucleotides, oligonucleotide analogs, oligonucleosides and/or oligonucleotide mimetics as described above. Such oligomeric compounds have also been referred to in the art as hybrids hemimers, gapmers or inverted gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

Oligomer Mimetics

Another preferred group of oligomeric compounds amenable to the present invention includes oligonucleotide mimetics. The term mimetic as it is applied to oligonucleotides is intended to include oligomeric compounds wherein only the furanose ring or both the furanose ring and the internucleotide linkage are replaced with novel groups, replacement of only the furanose ring is also referred to in the art as being a sugar surrogate. The heterocyclic base moiety or a modified heterocyclic base moiety is maintained for hybridization with an appropriate target nucleic acid. One such oligomeric compound, an oligonucleotide mimetic that has been shown to have excellent hybridization properties, is referred to as a peptide nucleic acid (PNA). In PNA oligomeric compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA oligomeric compounds include, but are not limited to, U.S. Pat. Nos. 5,539,082; 5,714,331; and 5,719,262, each of which is herein incorporated by reference. Further teaching of PNA oligomeric compounds can be found in Nielsen et al., *Science*, 1991, 254, 1497-1500.

One oligonucleotide mimetic that has been reported to have excellent hybridization properties, is peptide nucleic acids (PNA). The backbone in PNA compounds is two or more linked aminoethylglycine units which gives PNA an amide containing backbone. The heterocyclic base moieties are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

PNA has been modified to incorporate numerous modifications since the basic PNA structure was first prepared. The basic structure is shown below:

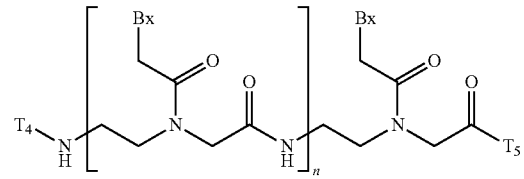

wherein

Bx is a heterocyclic base moiety;

$T_4$ is hydrogen, an amino protecting group, —C(O)R$_5$, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, alkylsulfonyl, arylsulfonyl, a chemical functional group, a reporter group, a conjugate group, a D or L α-amino acid linked via the α-carboxyl group or optionally through the ω-carboxyl group when the amino acid is aspartic acid or glutamic acid or a peptide derived from D, L or mixed D and L amino acids linked through a carboxyl group, wherein the substituent groups are selected from hydroxyl, amino, alkoxy, carboxy, benzyl, phenyl, nitro, thiol, thioalkoxy, halogen, alkyl, aryl, alkenyl and alkynyl;

$T_5$ is —OH, —N(Z$_1$)Z$_2$, R$_5$, D or L α-amino acid linked via the α-amino group or optionally through the ω-amino group when the amino acid is lysine or ornithine or a peptide derived from D, L or mixed D and L amino acids linked through an amino group, a chemical functional group, a reporter group or a conjugate group;

$Z_1$ is hydrogen, $C_1$-$C_6$ alkyl, or an amino protecting group;

$Z_2$ is hydrogen, $C_1$-$C_6$ alkyl, an amino protecting group, —C(=O)—(CH$_2$)$_n$-J-$Z_3$, a D or L α-amino acid linked via the α-carboxyl group or optionally through the ω-carboxyl group when the amino acid is aspartic acid or glutamic acid or a peptide derived from D, L or mixed D and L amino acids linked through a carboxyl group;

$Z_3$ is hydrogen, an amino protecting group, —$C_1$-$C_6$ alkyl, —C(=O)—CH$_3$, benzyl, benzoyl, or —(CH$_2$)$_n$—N(H)$Z_1$;

each J is O, S or NH;

$R_5$ is a carbonyl protecting group; and n is from 2 to about 50.

Another class of oligonucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. A preferred class of linking groups have been selected to give a non-ionic oligomeric compound. The non-ionic morpholino-based oligomeric compounds are less likely to have undesired interactions with cellular proteins. Morpholino-based oligomeric compounds are non-ionic mimics of oligonucleotides which are less likely to form undesired interactions with cellular proteins (Dwaine A. Braasch and David R. Corey, *Biochemistry*, 2002, 41(14), 4503-4510). Morpholino-based oligomeric compounds are disclosed in U.S. Pat. No. 5,034,506, issued Jul. 23, 1991. The morpholino class of oligomeric compounds have been prepared having a variety of different linking groups joining the monomeric subunits.

Morpholino nucleic acids have been prepared having a variety of different linking groups ($L_2$) joining the monomeric subunits. The basic formula is shown below:

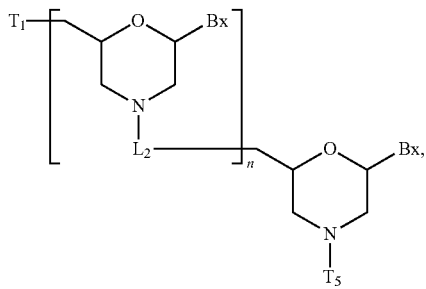

wherein $T_1$ is hydroxyl or a protected hydroxyl;

$T_5$ is hydrogen or a phosphate or phosphate derivative;

$L_2$ is a linking group; and n is from 2 to about 50.

A further class of oligonucleotide mimetic is referred to as cyclohexenyl nucleic acids (CeNA). The furanose ring normally present in an DNA/RNA molecule is replaced with a cyclohenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., *J. Am. Chem. Soc.,* 2000, 122, 8595-8602). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation. Furthermore the incorporation of CeNA into a sequence targeting RNA was stable to serum and able to activate *E. Coli* RNase resulting in cleavage of the target RNA strand.

The general formula of CeNA is shown below:

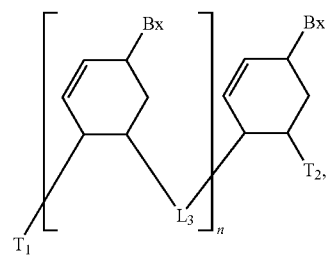

wherein each Bx is a heterocyclic base moiety;

$T_1$ is hydroxyl or a protected hydroxyl; and $T_2$ is hydroxyl or a protected hydroxyl.

Another class of oligonucleotide mimetic (anhydrohexitol nucleic acid) can be prepared from one or more anhydrohexitol nucleosides (see, Wouters and Herdewijn, *Bioorg. Med. Chem. Lett.,* 1999, 9, 1563-1566) and would have the general formula:

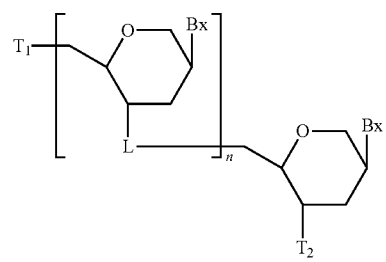

A further preferred modification includes Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage is preferably a methylene (—CH$_2$—)$_n$ group bridging the 2' oxygen atom and the 4' carbon atom wherein n is 1 or 2 (Singh et al., Chem. Commun., 1998, 4, 455-456). LNA and LNA analogs display very high duplex thermal stabilities with complementary DNA and RNA (Tm=+3 to +10 C), stability towards 3'-exonucleolytic degradation and good solubility properties. The basic structure of LNA showing the bicyclic ring system is shown below:

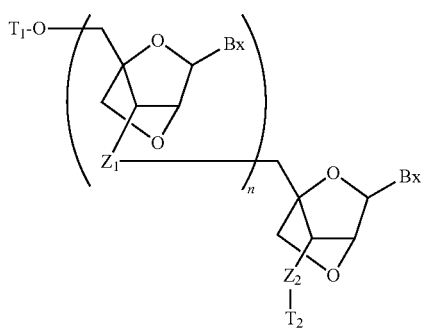

The conformations of LNAs determined by 2D NMR spectroscopy have shown that the locked orientation of the LNA nucleotides, both in single-stranded LNA and in duplexes, constrains the phosphate backbone in such a way as to introduce a higher population of the N-type conformation (Petersen et al., J. Mol. Recognit., 2000, 13, 44-53). These conformations are associated with improved stacking of the nucleobases (Wengel et al., Nucleosides Nucleotides, 1999, 18, 1365-1370).

LNA has been shown to form exceedingly stable LNA: LNA duplexes (Koshkin et al., J. Am. Chem. Soc., 1998, 120, 13252-13253). LNA:LNA hybridization was shown to be the most thermally stable nucleic acid type duplex system, and the RNA-mimicking character of LNA was established at the duplex level. Introduction of 3 LNA monomers (T or A) significantly increased melting points (Tm=+15/+11) toward DNA complements. The universality of LNA-mediated hybridization has been stressed by the formation of exceedingly stable LNA:LNA duplexes. The RNA-mimicking of LNA was reflected with regard to the N-type conformational restriction of the monomers and to the secondary structure of the LNA:RNA duplex.

LNAs also form duplexes with complementary DNA, RNA or LNA with high thermal affinities. Circular dichroism (CD) spectra show that duplexes involving fully modified LNA (esp. LNA:RNA) structurally resemble an A-form RNA:RNA duplex. Nuclear magnetic resonance (NMR) examination of an LNA:DNA duplex confirmed the 3'-endo conformation of an LNA monomer. Recognition of double-stranded DNA has also been demonstrated suggesting strand invasion by LNA. Studies of mismatched sequences show that LNAs obey the Watson-Crick base pairing rules with generally improved selectivity compared to the corresponding unmodified reference strands.

Novel types of LNA-oligomeric compounds, as well as the LNAs, are useful in a wide range of diagnostic and therapeutic applications. Among these are antisense applications, PCR applications, strand-displacement oligomers, substrates for nucleic acid polymerases and generally as nucleotide based drugs.

Potent and nontoxic antisense oligonucleotides containing LNAs have been described (Wahlestedt et al., Proc. Natl. Acad. Sci. U.S.A., 2000, 97, 5633-5638.) The authors have demonstrated that LNAs confer several desired properties to antisense agents. LNA/DNA copolymers were not degraded readily in blood serum and cell extracts. LNA/DNA copolymers exhibited potent antisense activity in assay systems as disparate as G-protein-coupled receptor signaling in living rat brain and detection of reporter genes in *Escherichia coli*. Lipofectin-mediated efficient delivery of LNA into living human breast cancer cells has also been accomplished.

The synthesis and preparation of the LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). LNAs and preparation thereof are also described in WO 98/39352 and WO 99/14226.

The first analogs of LNA, phosphorothioate-LNA and 2'-thio-LNAs, have also been prepared (Kumar et al., Bioorg. Med. Chem. Lett., 1998, 8, 2219-2222). Preparation of locked nucleoside analogs containing oligodeoxyribonucleotide duplexes as substrates for nucleic acid polymerases has also been described (Wengel et al., PCT International Application WO 98-DK393 19980914). Furthermore, synthesis of 2'-amino-LNA, a novel conformationally restricted high-affinity oligonucleotide analog with a handle has been described in the art (Singh et al., J. Org. Chem., 1998, 63, 10035-10039). In addition, 2'-Amino- and 2'-methylamino-LNA's have been prepared and the thermal stability of their duplexes with complementary RNA and DNA strands has been previously reported.

Further oligonucleotide mimetics have been prepared to include bicyclic and tricyclic nucleoside analogs having the formulas (amidite monomers shown):

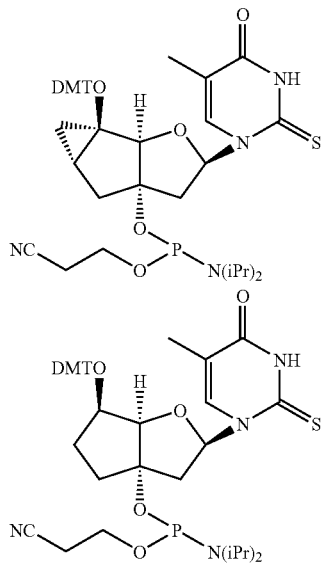

(see Steffens et al., *Helv. Chim. Acta*, 1997, 80, 2426-2439; Steffens et al., *J. Am. Chem. Soc.*, 1999, 121, 3249-3255; and Renneberg et al., *J. Am. Chem. Soc.*, 2002, 124, 5993-6002). These modified nucleoside analogs have been oligomerized using the phosphoramidite approach and the resulting oligomeric compounds containing tricyclic nucleoside analogs have shown increased thermal stabilities (Tm's) when hybridized to DNA, RNA and itself. Oligomeric compounds containing bicyclic nucleoside analogs have shown thermal stabilities approaching that of DNA duplexes.

Another class of oligonucleotide mimetic is referred to as phosphonomonoester nucleic acids incorporate a phosphorus group in a backbone the backbone. This class of olignucleotide mimetic is reported to have useful physical and biological and pharmacological properties in the areas of inhibiting gene expression (antisense oligonucleotides, ribozymes, sense oligonucleotides and triplex-forming oligonucleotides), as probes for the detection of nucleic acids and as auxiliaries for use in molecular biology.

The general formula (for definitions of Markush variables see: U.S. Pat. Nos. 5,874,553 and 6,127,346 herein incorporated by reference in their entirety) is shown below.

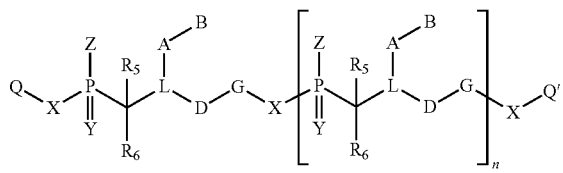

Another oligonucleotide mimetic has been reported wherein the furanosyl ring has been replaced by a cyclobutyl moiety.

Modified Internucleoside Linkages

Specific examples of preferred antisense oligomeric compounds useful in this invention include oligonucleotides containing modified e.g. non-naturally occurring internucleoside linkages. As defined in this specification, oligonucleotides having modified internucleoside linkages include internucleoside linkages that retain a phosphorus atom and internucleoside linkages that do not have a phosphorus atom. For the purposes of this specification, and as sometimes referenced in the art, modified oligonucleotides that do not have a phosphorus atom in their internucleoside backbone can also be considered to be oligonucleosides.

In the *C. elegans* system, modification of the internucleotide linkage (phosphorothioate) did not significantly interfere with RNAi activity. Based on this observation, it is suggested that certain preferred oligomeric compounds of the invention can also have one or more modified internucleoside linkages. A preferred phosphorus containing modified internucleoside linkage is the phosphorothioate internucleoside linkage.

Preferred modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

In more preferred embodiments of the invention, oligomeric compounds have one or more phosphorothioate and/or heteroatom internucleoside linkages, in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester internucleotide linkage is represented as —O—P(=O)(OH)—O—$CH_2$—]. The MMI type internucleoside linkages are disclosed in the above referenced U.S. Pat. No. 5,489,677. Preferred amide internucleoside linkages are disclosed in the above referenced U.S. Pat. No. 5,602,240.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

Modified Sugars

Oligomeric compounds of the invention may also contain one or more substituted sugar moieties. Preferred oligomeric compounds comprise a sugar substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$$NH_2$, O($CH_2$)$_n$$CH_3$, O($CH_2$)$_n$O$NH_2$, and O($CH_2$)$_n$ON[($CH_2$)$_n$$CH_3$]$_2$, where n and m are from 1 to about 10. Other preferred oligonucleotides comprise a sugar substituent group selected from: $C_1$ to $C_{10}$ lower alkyl, substituted lower alkyl, alkenyl, alkynyl, alkaryl, aralkyl, O-alkaryl or O-aralkyl, SH, S$CH_3$, OCN, Cl, Br, CN, C$F_3$, OC$F_3$, SO$CH_3$, S$O_2$$CH_3$, ON$O_2$, N$O_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2$$CH_2$O$CH_3$, also known as 2'-O-(2-methoxyethyl) or 2'-MOE) (Martin et al., *Helv. Chim. Acta*, 1995, 78, 486-504) i.e., an alkoxyalkoxy group. A further preferred modification includes 2'-dimethylamino-oxyethoxy, i.e., a O(CH$_2$)$_2$ON(CH$_3$)$_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—CH2OCH$_2$N(CH$_3$)$_2$.

Other preferred sugar substituent groups include methoxy (—O—CH$_3$), aminopropoxy (—OCH$_2$CH$_2$CH$_2$NH$_2$), allyl (—CH$_2$—CH═CH$_2$), —O-allyl (—O—C$_1$H$_2$—CH═CH$_2$) and fluoro (F). 2'-Sugar substituent groups may be in the arabino (up) position or ribo (down) position. A preferred 2'-arabino modification is 2'-F. Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

Further representative sugar substituent groups include groups of formula I$_a$ or II$_a$:

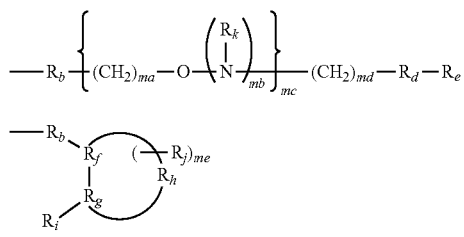

wherein:
R$_b$ is O, S or NH;
R$_d$ is a single bond, O, S or C(═O);
R$_e$ is C$_1$-C$_{10}$ alkyl, N(R$_k$)(R$_m$), N(R$_k$)(R$_n$), N═C(R$_p$)C(R$_q$), N═C(R$_p$)(R$_r$) or has formula III$_a$;

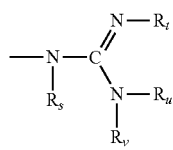

R$_p$ and R$_q$ are each independently hydrogen or C$_1$-C$_{10}$ alkyl;
R$_r$ is —R$_x$—R$_y$;
each R$_s$, R$_t$, R$_u$ and R$_v$ is, independently, hydrogen, C(O)R$_w$, substituted or unsubstituted C$_1$-C$_{10}$ alkyl, substituted or unsubstituted C$_2$-C$_{10}$ alkenyl, substituted or unsubstituted C$_2$-C$_{10}$ alkynyl, alkylsulfonyl, arylsulfonyl, a chemical functional group or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl;
or optionally, R$_u$, and R$_v$, together form a phthalimido moiety with the nitrogen atom to which they are attached;
each R$_w$ is, independently, substituted or unsubstituted C$_1$-C$_{10}$ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, isobutyryl, phenyl or aryl;
R$_k$ is hydrogen, a nitrogen protecting group or —R$_x$—R$_y$;
R$_p$ is hydrogen, a nitrogen protecting group or —R$_x$—R$_y$;
R$_x$ is a bond or a linking moiety;
R$_y$ is a chemical functional group, a conjugate group or a solid support medium;
each R$_m$ and R$_n$ is, independently, H, a nitrogen protecting group, substituted or unsubstituted C$_1$-C$_{10}$ alkyl, substituted or unsubstituted C$_2$-C$_{10}$ alkenyl, substituted or unsubstituted C$_2$-C$_{10}$ alkynyl, wherein the substituent groups are selected from hydroxyl, amino, alkoxy, carboxy, benzyl, phenyl, nitro, thiol, thioalkoxy, halogen, alkyl, aryl, alkenyl, alkynyl; NH$_3^+$, N(R$_u$)(R$_v$), guanidino and acyl where the acyl is an acid amide or an ester;
or R$_m$ and R$_n$, together, are a nitrogen protecting group, are joined in a ring structure that optionally includes an additional heteroatom selected from N and O or are a chemical functional group;
R$_i$ is OR$_z$, SR$_z$, or N(R$_z$)$_2$;
each R$_z$ is, independently, H, C$_1$-C$_8$ alkyl, C$_1$-C$_8$ haloalkyl, C(═NH)N(H)R$_u$, C(═O)N(H)R$_u$ or OC(═O)N(H)R$_u$;
R$_f$, R$_g$ and R$_h$ comprise a ring system having from about 4 to about 7 carbon atoms or having from about 3 to about 6 carbon atoms and 1 or 2 heteroatoms wherein said heteroatoms are selected from oxygen, nitrogen and sulfur and wherein said ring system is aliphatic, unsaturated aliphatic, aromatic, or saturated or unsaturated hetero cyclic;
R$_j$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, N(R$_k$)(R$_m$) OR$_k$, halo, SR$_k$ or CN;
m$_a$ is 1 to about 10;
each mb is, independently, 0 or 1;
mc is 0 or an integer from 1 to 10;
md is an integer from 1 to 10;
me is from 0, 1 or 2; and
provided that when mc is 0, md is greater than 1.

Representative substituents groups of Formula I are disclosed in U.S. patent application Ser. No. 09/130,973, filed Aug. 7, 1998, entitled "Capped 2'-Oxyethoxy Oligonucleotides," hereby incorporated by reference in its entirety.

Representative cyclic substituent groups of Formula II are disclosed in U.S. patent application Ser. No. 09/123,108, filed Jul. 27, 1998, entitled "RNA Targeted 2'-Oligomeric compounds that are Conformationally Preorganized," hereby incorporated by reference in its entirety.

Particularly preferred sugar substituent groups include O[(CH$_2$)$_n$O]$_m$CH$_3$, O(CH$_2$)$_n$OCH$_3$, O(CH$_2$)$_n$NH$_2$, O(CH$_2$)$_n$CH$_3$, O(CH$_2$)$_n$ONH$_2$, and O(CH$_2$)$_n$ON[(CH$_2$)$_n$CH$_3$)]$_2$, where n and m are from 1 to about 10.

Representative guanidino substituent groups that are shown in formula III and IV are disclosed in co-owned U.S. patent application Ser. No. 09/349,040, entitled "Functionalized Oligomers", filed Jul. 7, 1999, hereby incorporated by reference in its entirety.

Representative acetamido substituent groups are disclosed in U.S. Pat. No. 6,147,200 which is hereby incorporated by reference in its entirety.

Representative dimethylaminoethyloxyethyl substituent groups are disclosed in International Patent Application PCT/US99/17895, entitled "2'-O-Dimethylaminoethyloxyethyl-Oligomeric compounds", filed Aug. 6, 1999, hereby incorporated by reference in its entirety.

Modified Nucleobases/Naturally Occurring Nucleobases

Oligomeric compounds may also include nucleobase (often referred to in the art simply as "base" or "heterocyclic base moiety") modifications or substitutions. As used herein, "unmodified" or "natural" nucleobases include the purine bases adenine (A) and guanine (G), and the pyrimidine bases thymine (T), cytosine (C) and uracil (U). Modified nucleobases also referred herein as heterocyclic base moieties include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278) and are presently preferred base substitutions, even more particularly when combined with 2'-O-methoxyethyl sugar modifications.

Oligomeric compounds of the present invention can also include polycyclic heterocyclic compounds in place of one or more heterocyclic base moieties. A number of tricyclic heterocyclic compounds have been previously reported. These compounds are routinely used in antisense applications to increase the binding properties of the modified strand to a target strand. The most studied modifications are targeted to guanosines hence they have been termed G-clamps or cytidine analogs. Many of these polycyclic heterocyclic compounds have the general formula:

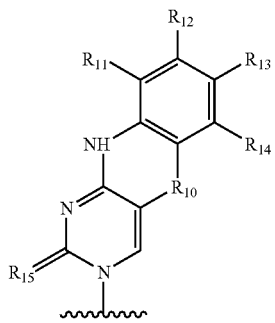

Representative cytosine analogs that make 3 hydrogen bonds with a guanosine in a second strand include 1,3-diazaphenoxazine-2-one ($R_{10}$=O, $R_{11}$-$R_{14}$=H) [Kurchavov, et al., *Nucleosides and Nucleotides*, 1997, 16, 1837-1846], 1,3-diazaphenothiazine-2-one ($R_{10}$=S, $R_{11}$-$R_{14}$=H), [Lin, K.-Y.; Jones, R. J.; Matteucci, M. J. Am. Chem. Soc. 1995, 117, 3873-3874] and 6,7,8,9-tetrafluoro-1,3-diazaphenoxazine-2-one ($R_{10}$=O, $R_{11}$-$R_{14}$=F) [Wang, J.; Lin, K.-Y., Matteucci, M. Tetrahedron Lett. 1998, 39, 8385-8388]. Incorporated into oligonucleotides these base modifications were shown to hybridize with complementary guanine and the latter was also shown to hybridize with adenine and to enhance helical thermal stability by extended stacking interactions (also see U.S. patent application entitled "Modified Peptide Nucleic Acids" filed May 24, 2002, Ser. No. 10/155,920; and U.S. patent application entitled "Nuclease Resistant Chimeric Oligonucleotides" filed May 24, 2002, Ser. No. 10/013,295, both of which are commonly owned with this application and are herein incorporated by reference in their entirety).

Further helix-stabilizing properties have been observed when a cytosine analog/substitute has an aminoethoxy moiety attached to the rigid 1,3-diazaphenoxazine-2-one scaffold ($R_{10}$=O, $R_{11}$=—O—($CH_2$)$_2$—$NH_2$, $R_{12\text{-}14}$=H) [Lin, K.-Y.; Matteucci, M. J. Am. Chem. Soc. 1998, 120, 8531-8532]. Binding studies demonstrated that a single incorporation could enhance the binding affinity of a model oligonucleotide to its complementary target DNA or RNA with a $\Delta T_m$ of up to 18° relative to 5-methyl cytosine (dC5$^{me}$), which is the highest known affinity enhancement for a single modification, yet. On the other hand, the gain in helical stability does not compromise the specificity of the oligonucleotides. The $T_m$ data indicate an even greater discrimination between the perfect match and mismatched sequences compared to dC5$^{me}$. It was suggested that the tethered amino group serves as an additional hydrogen bond donor to interact with the Hoogsteen face, namely the O6, of a complementary guanine thereby forming 4 hydrogen bonds. This means that the increased affinity of G-clamp is mediated by the combination of extended base stacking and additional specific hydrogen bonding.

Further tricyclic heterocyclic compounds and methods of using them that are amenable to the present invention are disclosed in U.S. Pat. No. 6,028,183, which issued on May 22, 2000, and U.S. Pat. No. 6,007,992, which issued on Dec. 28, 1999, the contents of both are commonly assigned with this application and are incorporated herein in their entirety.

The enhanced binding affinity of the phenoxazine derivatives together with their uncompromised sequence specificity makes them valuable nucleobase analogs for the development of more potent antisense-based drugs. In fact, promising data have been derived from in vitro experiments demonstrating that heptanucleotides containing phenoxazine substitutions are capable to activate RNaseH, enhance cellular uptake and exhibit an increased antisense activity [Lin, K-Y; Matteucci, M. J. Am. Chem. Soc. 1998, 120, 8531-8532]. The activity enhancement was even more pronounced in case of G-clamp, as a single substitution was shown to significantly improve the in vitro potency of a 20mer 2'-deoxyphosphorothioate oligonucleotides [Flanagan, W. M.; Wolf, J. J.; Olson, P.; Grant, D.; Lin, K.-Y.; Wagner, R. W.; Matteucci, M. Proc. Natl. Acad. Sci. USA, 1999, 96, 3513-3518]. Nevertheless, to optimize oligonucleotide design and to better understand the impact of these heterocyclic modifications on the biological activity, it is important to evaluate their effect on the nuclease stability of the oligomers.

Further modified polycyclic heterocyclic compounds useful as heterocyclic bases are disclosed in but not limited to, the above noted U.S. Pat. No. 3,687,808, as well as U.S. Pat. Nos. 4,845,205; 5,130,302; 5,134,066; 5,175,273; 5,367,066; 5,432,272; 5,434,257; 5,457,187; 5,459,255; 5,484,908; 5,502,177; 5,525,711; 5,552,540; 5,587,469; 5,594,121; 5,596,091; 5,614,617; 5,645,985; 5,646,269; 5,750,692; 5,830,653; 5,763,588; 6,005,096; and 5,681,941, and U.S. patent application Ser. No. 09/996,292 filed Nov. 28, 2001, certain of which are commonly owned with the instant application, and each of which is herein incorporated by reference.

Additional Modified Nucleobases

The term "universal base" as used herein, refers to a monomer in a first sequence that can pair with a naturally occurring base, i.e A, C, G, T or U at a corresponding position in a second sequence of a duplex in which one or more of the following is true: (1) there is essentially no pairing between the two; or (2) the pairing between them occurs non-discriminantly with each of the naturally occurring bases and without significant destabilization of the duplex. For examples of universal bases see Survey and summary: the applications of universal DNA base analogs. Loakes, D. *Nucleic Acids Research,* 2001, 29, 12, 2437-2447.

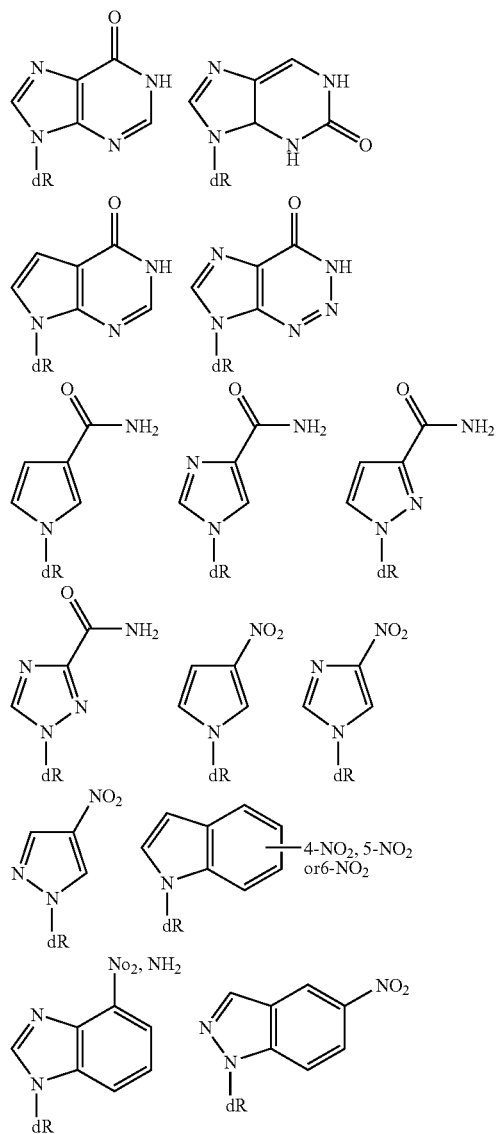

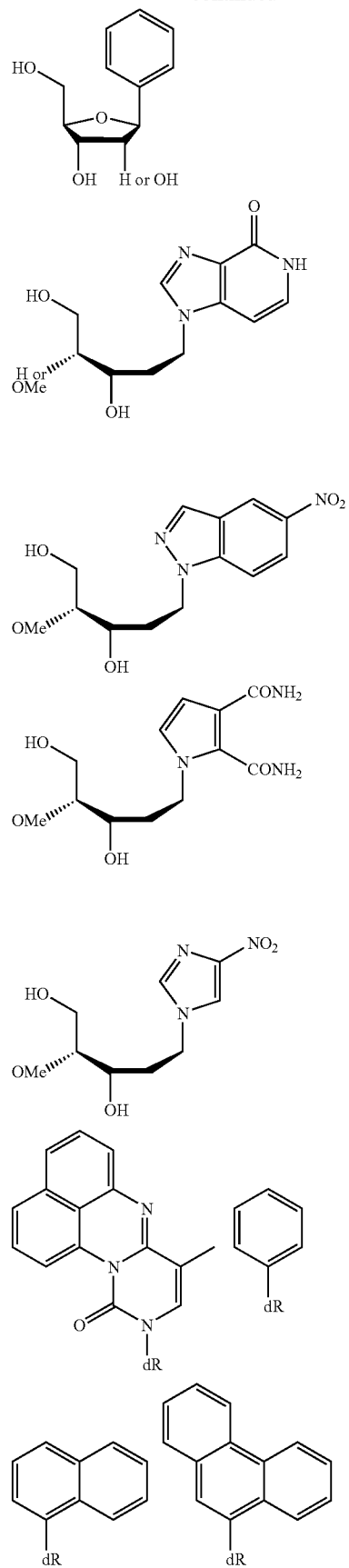

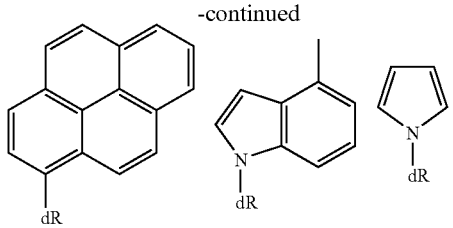

The term "hydrophobic base" as used herein, refers to a monomer in a first sequence that can pair with a naturally occurring base, i.e A, C, G, T or U at a corresponding position in a second sequence of a duplex in which one or more of the following is true: (1) the hydrophobic base acts as a non-polar close size and shape mimic (isostere) of one of the naturally occurring nucleosides; or (2) the hydrophobic base lacks all hydrogen bonding functionality on the Watson-Crick pairing edge.

For examples of adenine isosteres, see Probing the requirements for recognition and catalysis in Fpg and MutY with nonpolar adenine isosteres. Francis, A W, Helquist, S A, Kool, E T, David, S S. *J. Am. Chem. Soc.*, 2003, 125, 16235-16242 or Structure and base pairing properties of a replicable non-polar isostere for deoxyadenosine. Guckian, K M, Morales, J C, Kool, E T. *J. Org. Chem.*, 1998, 63, 9652-96565.

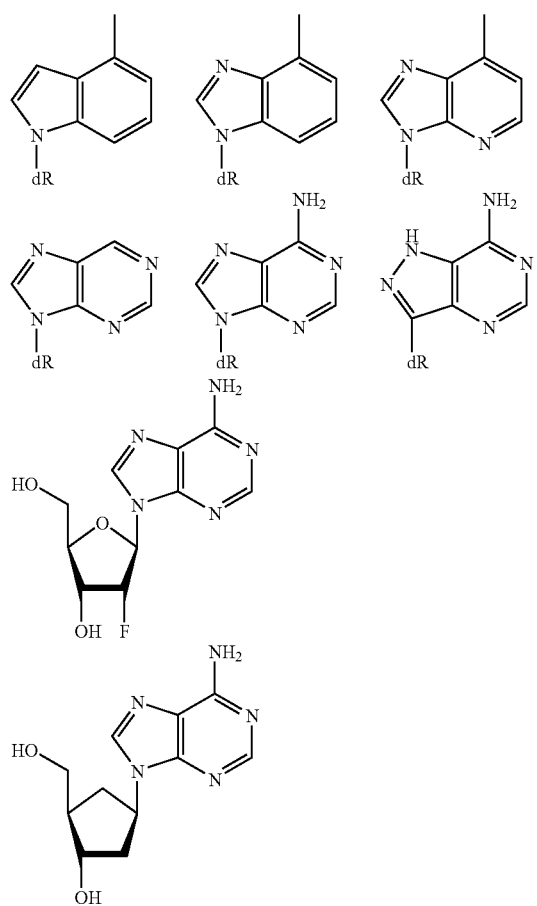

For an example of a cytosine isostere, see Hydrolysis of RNA/DNA hybrids containing nonpolar pyrimidine isostreres defines regions essential for HIV type polypurine tract selection. Rausch, J W, Qu, J, Yi-Brunozzi H Y, Kool, E T, LeGrice, S F J. *Proc. Natl. Acad. Sci.*, 2003, 100, 11279-11284.

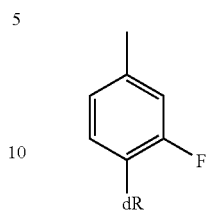

For an example of a guanosine isostere, see A highly effective nonpolar isostere of doeoxguanosine: synthesis, structure, stacking and base pairing. O'Neil, B M, Ratto, J E, Good, K L, Tahmassebi, D C, Helquist, S A, Morales, J C, Kool, E T. *J. Org. Chem.*, 2002, 67, 5869-5875.

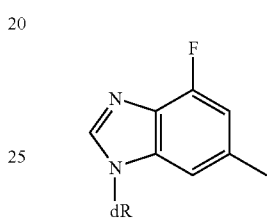

For an example of a thymidine isostere, see A thymidine triphosphate shape analog lacking Watson-Crick pairing ability is replicated with high sequence selectivity. Moran, S, Ren, R X-F, Kool, E T. *Proc. Natl. Acad. Sci.*, 1997, 94, 10506-10511 or Difluorotoluene, a nonpolar isostere for thymidine, codes specifically and efficiently for adenine in DNA replication. *J. Am. Chem. Soc.* 1997, 119, 2056-2057.

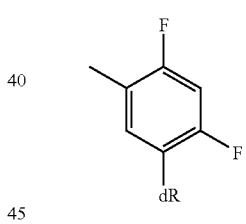

The term "promiscuous base" as used herein, refers to a monomer in a first sequence that can pair with a naturally occurring base, i.e A, C, G, T or U at a corresponding position in a second sequence of a duplex in which the promiscuous base can pair non-discriminantly with more than one of the naturally occurring bases, i.e. A, C, G, T, U, but not with all four of them. For an example, see Polymerase recognition of synthetic oligodeoxyribonucleotides incorporating degenerate pyrimidine and purine bases. Hill, F.; Loakes, D.; Brown, D. M. *Proc. Natl. Acad. Sci.*, 1998, 95, 4258-4263.

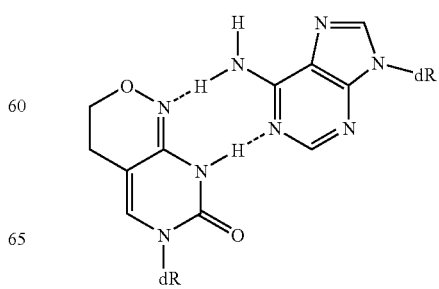

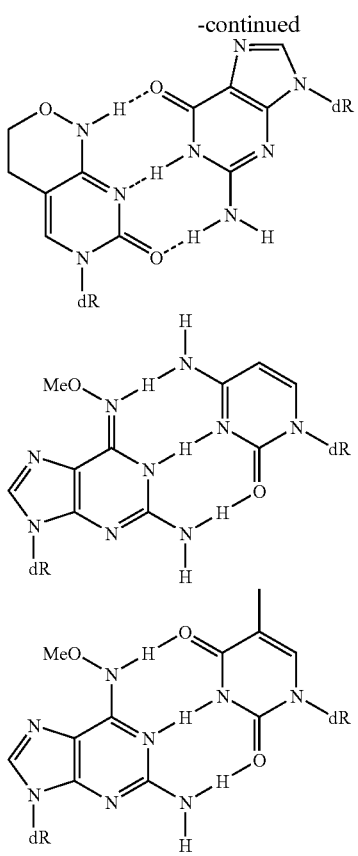

The term "size expanded base" as used herein, refers to analogs of naturally occurring nucleobases that are larger in size and retain their Watson-Crick pairing ability. For examples see A four-base paired genetic helix with expanded size. Liu, B, Gao, J, Lynch, S R, Saito, D, Maynard, L, Kool, E T., *Science*, 2003, 302, 868-871 and Toward a new genetic system with expanded dimension: size expanded analogues of deoxyadenosine and thymidine. Liu, H, Goa, J, Maynard, Y, Saito, D, Kool, E T, *J. Am. Chem. Soc.* 2004, 126, 1102-1109.

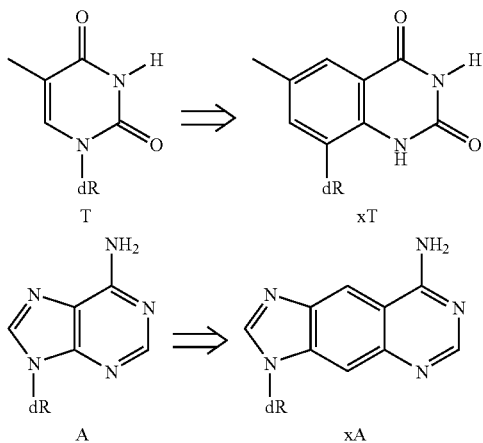

The term fluorinated nucleobase as used herein, refers to a nucleobase or nucleobase analog, wherein one or more of the aromatic ring substituents is a fluoroine atom. It may be possible that all of the ring substituents are fluoroine atoms. For examples of fluorinated nucleobases see fluorinated DNA bases as probes of electrostatic effects in DNA base stacking. Lai, J S, QU, J, Kool, E T, *Angew. Chem. Int. Ed.*, 2003, 42, 5973-5977 and Selective pairing of polyfluorinated DNA bases, Lai, J S, Kool, E T, *J. Am. Chem. Soc.*, 2004, 126, 3040-3041 and The effect of universal fluorinated nucleobases on the catalytic activity of ribozymes, Kloppfer, A E, Engels, J W, *Nucleosides, Nucleotides & Nucleic Acids*, 2003, 22, 1347-1350 and Synthesis of 2'aminoalkyl-substituted fluorinated nucleobases and their influence on the kinetic properties of hammerhead ribozymes, Klopffer, A E, Engels, J W, *ChemBioChem.*, 2003, 5, 707-716

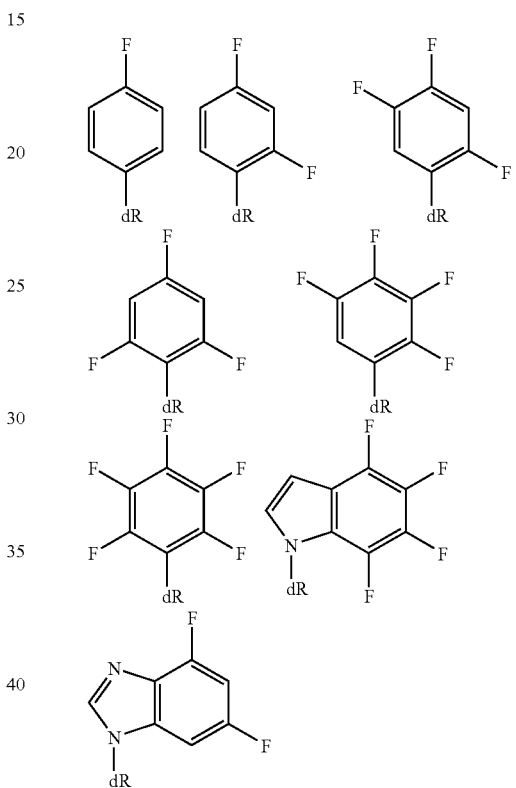

Conjugates

Oligomeric compounds used in the compositions of the present invention can also be modified to have one or more moieties or conjugates which enhance the activity, cellular distribution or cellular uptake of the resulting oligomeric compounds. In one embodiment such modified oligomeric compounds are prepared by covalently attaching conjugate groups to functional groups such as hydroxyl or amino groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference. Conjugate moieties include but are not limited to lipid moieties such as a cholesterol moiety (Letsinger et al., *Proc. Natl. Acad. Sci. USA,* 1989, 86, 6553-6556), cholic acid (Manoharan et al., *Bioorg. Med. Chem. Let.,* 1994, 4, 1053-1060), a thioether, e.g., hexyl-5-tritylthiol (Manoharan et al., *Ann. N.Y. Acad. Sci.,* 1992, 660, 306-309; Manoharan et al., *Bioorg. Med. Chem. Let.,* 1993, 3, 2765-2770), a thiocholesterol (Oberhauser et al., *Nucl. Acids Res.,* 1992, 20, 533-538), an aliphatic chain, e.g., dodecandiol or undecyl residues (Saison-Behmoaras et al., *EMBO J.,* 1991, 10, 1111-1118; Kabanov et al., *FEBS Lett.,* 1990, 259, 327-330; Svinarchuk et al., *Biochimie,* 1993, 75, 49-54), a phospholipid, e.g., di-hexadecyl-rac-glycerol or triethylammonium 1,2-di-O-hexadecyl-rac-glycero-3-H-phosphonate (Manoharan et al., *Tetrahedron Lett.,* 1995, 36, 3651-3654; Shea et al., *Nucl. Acids Res.,* 1990, 18, 3777-3783), a polyamine or a polyethylene glycol chain (Manoharan et al., *Nucleosides & Nucleotides,* 1995, 14, 969-973), or adamantane acetic acid (Manoharan et al., *Tetrahedron Lett.,* 1995, 36, 3651-3654), a palmityl moiety (Mishra et al., *Biochim. Biophys. Acta,* 1995, 1264, 229-237), or an octadecylamine or hexylamino-carbonyl-oxycholesterol moiety (Crooke et al., *J. Pharmacol. Exp. Ther.,* 1996, 277, 923-937.

The oligomeric compounds of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

3'-Endo Modifications

In one aspect of the present invention oligomeric compounds include nucleosides synthetically modified to induce a 3'-endo sugar conformation. A nucleoside can incorporate synthetic modifications of the heterocyclic base moiety, the sugar moiety or both to induce a desired 3'-endo sugar conformation. These modified nucleosides are used to mimic RNA like nucleosides so that particular properties of an oligomeric compound can be enhanced while maintaining the desirable 3'-endo conformational geometry. There is an apparent preference for an RNA type duplex (A form helix, predominantly 3'-endo) as a requirement of RNA interference which is supported in part by the fact that duplexes composed of 2'-deoxy-2'-F-nucleosides appear efficient in triggering RNAi response in the *C. elegans* system. Properties that are enhanced by using more stable 3'-endo nucleosides include but aren't limited to modulation of pharmacokinetic properties through modification of protein binding, protein off-rate, absorption and clearance; modulation of nuclease stability as well as chemical stability; modulation of the binding affinity and specificity of the oligomer (affinity and specificity for enzymes as well as for complementary sequences); and increasing efficacy of RNA cleavage. The present invention provides oligomeric compounds having one or more nucleosides modified in such a way as to favor a C3'-endo type conformation.

Scheme 1

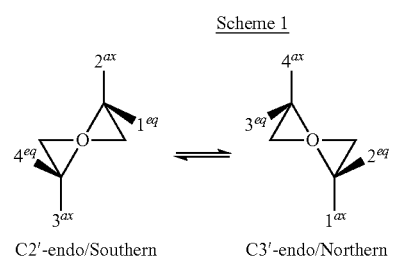

C2'-endo/Southern      C3'-endo/Northern

Nucleoside conformation is influenced by various factors including substitution at the 2', 3' or 4'-positions of the pentofuranosyl sugar. Electronegative substituents generally prefer the axial positions, while sterically demanding substituents generally prefer the equatorial positions (Principles of Nucleic Acid Structure, Wolfgang Sanger, 1984, Springer-Verlag.) Modification of the 2' position to favor the 3'-endo conformation can be achieved while maintaining the 2'-OH as a recognition element, as illustrated in FIG. 2, below (Gallo et al., Tetrahedron (2001), 57, 5707-5713. Harry-O'kuru et al., J. Org. Chem., (1997), 62(6), 1754-1759 and Tang et al., J. Org. Chem. (1999), 64, 747-754.) Alternatively, preference for the 3'-endo conformation can be achieved by deletion of the 2'-OH as exemplified by 2'deoxy-2'-nucleosides (Kawasaki et al., J. Med. Chem. (1993), 36, 831-841), which adopts the 3'-endo conformation positioning the electronegative fluorine atom in the axial position. Other modifications of the ribose ring, for example substitution at the 4'-position to give 4'-F modified nucleosides (Guillerm et al., Bioorganic and Medicinal Chemistry Letters (1995), 5, 1455-1460 and Owen et al., J. Org. Chem. (1976), 41, 3010-3017), or for example modification to yield methanocarba nucleoside analogs (Jacobson et al., J. Med. Chem. Lett. (2000), 43, 2196-2203 and Lee et al., Bioorganic and Medicinal Chemistry Letters (2001), 11, 1333-1337) also induce preference for the 3'-endo conformation. Some modifications actually lock the conformational geometry by formation of a bicyclic sugar moiety e.g. locked nucleic acid (LNA, Singh et al, Chem. Commun. (1998), 4, 455-456), and ethylene bridged nucleic acids (ENA, Morita et al, Bioorganic & Medicinal Chemistry Letters (2002), 12, 73-76.)

Examples of modified nucleosides amenable to the present invention are shown below. These examples are meant to be representative and not exhaustive.

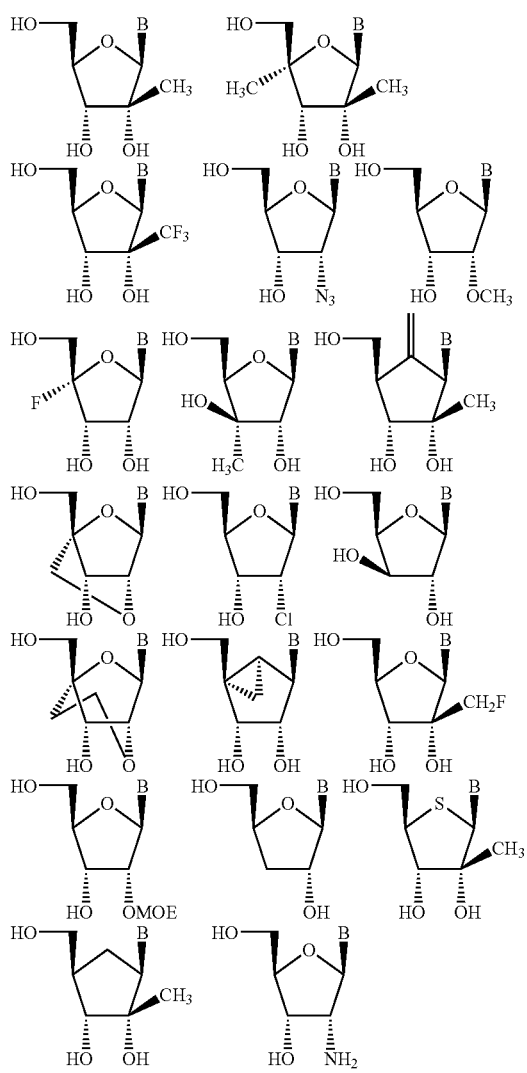

The preferred conformation of modified nucleosides and their oligomers can be estimated by various methods such as molecular dynamics calculations, nuclear magnetic resonance spectroscopy and CD measurements. Hence, modifications predicted to induce RNA like conformations, A-form duplex geometry in an oligomeric context, are selected for use in one or more of the oligomeric compounds of the present invention. The synthesis of numerous of the modified nucleosides amenable to the present invention are known in the art (see for example, Chemistry of Nucleosides and Nucleotides Vol 1-3, ed. Leroy B. Townsend, 1988, Plenum press, and the examples section below.) Nucleosides known to be inhibitors/substrates for RNA dependent RNA polymerases (for example HCV NS5B In one aspect, the present invention is directed to oligomeric compounds that are prepared having enhanced properties compared to native RNA against nucleic acid targets. A target is identified and an oligomeric compound is selected having an effective length and sequence that is complementary to a portion of the target sequence. Each nucleoside of the selected sequence is scrutinized for possible enhancing modifications. A preferred modification would be the replacement of one or more RNA nucleosides with nucleosides that have the same 3'-endo conformational geometry. Such modifications can enhance chemical and nuclease stability relative to native RNA while at the same time being much cheaper and easier to synthesize and/or incorporate into an oligomeric compound. The selected sequence can be further divided into regions and the nucleosides of each region evaluated for enhancing modifications that can be the result of a chimeric configuration. Consideration is also given to the termini (e.g. 5' and 3'-termini) as there are often advantageous modifications that can be made to one or more of the terminal monomeric subunits. In one aspect of the invention, desired properties and or activity of oligomeric compounds are enhanced by the inclusion of a 5'-phosphate or modified phosphate moiety.

The terms used to describe the conformational geometry of homoduplex nucleic acids are "A Form" for RNA and "B Form" for DNA. The respective conformational geometry for RNA and DNA duplexes was determined from X-ray diffraction analysis of nucleic acid fibers (Arnott and Hukins, Biochem. Biophys. Res. Comm., 1970, 47, 1504.) In general, RNA:RNA duplexes are more stable and have higher melting temperatures (Tm's) than DNA:DNA duplexes (Sanger et al., Principles of Nucleic Acid Structure, 1984, Springer-Verlag; New York, N.Y.; Lesnik et al., Biochemistry, 1995, 34, 10807-10815; Conte et al., Nucleic Acids Res., 1997, 25, 2627-2634). The increased stability of RNA has been attributed to several structural features, most notably the improved base stacking interactions that result from an A-form geometry (Searle et al., Nucleic Acids Res., 1993, 21, 2051-2056). The presence of the 2' hydroxyl in RNA biases the sugar toward a C3' endo pucker, i.e., also designated as Northern pucker, which causes the duplex to favor the A-form geometry. In addition, the 2' hydroxyl groups of RNA can form a network of water mediated hydrogen bonds that help stabilize the RNA duplex (Egli et al., Biochemistry, 1996, 35, 8489-8494). On the other hand, deoxy nucleic acids prefer a C2' endo sugar pucker, i.e., also known as Southern pucker, which is thought to impart a less stable B-form geometry (Sanger, W. (1984) Principles of Nucleic Acid Structure, Springer-Verlag, New York, N.Y.). As used herein, B-form geometry is inclusive of both C2'-endo pucker and O4'-endo pucker. This is consistent with Berger, et. al., Nucleic Acids Research, 1998, 26, 2473-2480, who pointed out that in considering the furanose conformations which give rise to B-form duplexes consideration should also be given to a O4'-endo pucker contribution.

DNA:RNA hybrid duplexes, however, are usually less stable than pure RNA:RNA duplexes, and depending on their sequence may be either more or less stable than DNA:DNA duplexes (Searle et al., Nucleic Acids Res., 1993, 21, 2051-2056). The structure of a hybrid duplex is intermediate between A- and B-form geometries, which may result in poor stacking interactions (Lane et al., Eur. J. Biochem., 1993, 215, 297-306; Fedoroff et al., J. Mol. Biol., 1993, 233, 509-523; Gonzalez et al., Biochemistry, 1995, 34, 4969-4982; Horton et al., J. Mol. Biol., 1996, 264, 521-533). The stability of the duplex formed between a target RNA and a synthetic sequence is central to therapies such as but not limited to antisense and RNA interference as these mechanisms require the binding of a synthetic strand of oligomeric compound to an RNA target strand. In the case of antisense, effective inhibition of the mRNA requires that the antisense DNA have a very high binding affinity with the mRNA. Otherwise the desired interaction between the synthetic strand and target mRNA strand will occur infrequently, resulting in decreased efficacy.

One routinely used method of modifying the sugar puckering is the substitution of the sugar at the 2'-position with a substituent group that influences the sugar geometry. The influence on ring conformation is dependant on the nature of the substituent at the 2'-position. A number of different substituents have been studied to determine their sugar puckering effect. For example, 2'-halogens have been studied showing that the 2'-fluoro derivative exhibits the largest population (65%) of the C3'-endo form, and the 2'-iodo exhibits the Lowest population (7%). The populations of adenosine (2'-OH) versus deoxyadenosine (2'-H) are 36% and 19%, respectively. Furthermore, the effect of the 2'-fluoro group of adenosine dimers (Z'-deoxy-2'-fluoroadenosine-2'-deoxy-2'-fluoro-adenosine) is further correlated to the stabilization of the stacked conformation.

As expected, the relative duplex stability can be enhanced by replacement of 2'-OH groups with 2'-F groups thereby increasing the C3'-endo population. It is assumed that the highly polar nature of the 2'-F bond and the extreme preference for C3'-endo puckering may stabilize the stacked conformation in an A-form duplex. Data from UV hypochromicity, circular dichroism, and $^1$H NNM also indicate that the degree of stacking decreases as the electronegativity of the halo substituent decreases. Furthermore, steric bulk at the 2'-position of the sugar moiety is better accommodated in an A-form duplex than a B-form duplex. Thus, a 2'-substituent on the 3'-terminus of a dinucleoside monophosphate is thought to exert a number of effects on the stacking conformation: steric repulsion, furanose puckering preference, electrostatic repulsion, hydrophobic attraction, and hydrogen bonding capabilities. These substituent effects are thought to be determined by the molecular size, electronegativity, and hydrophobicity of the substituent. Melting temperatures of complementary strands is also increased with the 2'-substituted adenosine diphosphates. It is not clear whether the 3'-endo preference of the conformation or the presence of the substituent is responsible for the increased binding. However, greater overlap of adjacent bases (stacking) can be achieved with the 3'-endo conformation.

One synthetic 2'-modification that imparts increased nuclease resistance and a very high binding affinity to nucleotides is the 2-methoxyethoxy (2'-MOE, 2'-OCH$_2$CH$_2$OCH$_3$) side chain (Baker et al., *J. Biol. Chem.*, 1997, 272, 11944-12000). One of the immediate advantages of the 2'-MOE substitution is the improvement in binding affinity, which is greater than many similar 2' modifications such as O-methyl, O-propyl, and O-aminopropyl. Oligonucleotides having the 2'-O-methoxyethyl substituent also have been shown to be antisense inhibitors of gene expression with promising features for in vivo use (Martin, P., *Helv. Chim. Acta*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926). Relative to DNA, the oligonucleotides having the 2'-MOE modification displayed improved RNA affinity and higher nuclease resistance. Chimeric oligonucleotides having 2'-MOE substituents in the wing nucleosides and an internal region of deoxy-phosphorothioate nucleotides (also termed a gapped oligonucleotide or gapmer) have shown effective reduction in the growth of tumors in animal models at low doses. 2'-MOE substituted oligonucleotides have also shown outstanding promise as antisense agents in several disease states. One such MOE substituted oligonucleotide is presently being investigated in clinical trials for the treatment of CMV retinitis.

To better understand the higher RNA affinity of 2'-O-methoxyethyl substituted RNA and to examine the conformational properties of the 2'-O-methoxyethyl substituent, two dodecamer oligonucleotides were synthesized having SEQ ID NO: 10 (CGC GAA UUC GCG) and SEQ ID NO: 11 (GCG CUU AAG CGC). These self-complementary strands have every 2'-position modified with a 2'-O-methoxyethyl. The duplex was crystallized at a resolution of 1.7 Ångstrom and the crystal structure was determined. The conditions used for the crystallization were 2 mM oligonucleotide, 50 mM Na Hepes pH 6.2-7.5, 10.50 mM MgCl$_2$, 15% PEG 400. The crystal data showed: space group C2, cell constants a=41.2 Å, b=34.4 Å, c=46.6 Å, =92.4°. The resolution was 1.7 Å at –170° C. The current R=factor was 20% (R$_{free}$ 26%).

This crystal structure is believed to be the first crystal structure of a fully modified RNA oligonucleotide analogue. The duplex adopts an overall A-form conformation and all modified sugars display a C3'-endo pucker. In most of the 2'-O-substituents, the torsion angle around the A'-B' bond, (as depicted below), of the ethylene glycol linker has a gauche conformation. For 2'-O-MOE, A' and B' are methylene moieties of the ethyl portion of the MOE and R' is the methoxy portion.

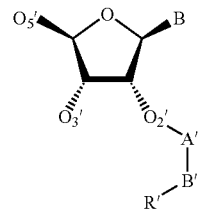

In the crystal, the 2'-O-MOE RNA duplex adopts a general orientation such that the crystallographic 2-fold rotation axis does not coincide with the molecular 2-fold rotation axis. The duplex adopts the expected A-type geometry and all of the 24 2'-O-MOE substituents were visible in the electron density maps at full resolution. The electron density maps as well as the temperature factors of substituent atoms indicate flexibility of the 2'-O-MOE substituent in some cases.

Most of the 2'-O-MOE substituents display a gauche conformation around the C—C bond of the ethyl linker. However, in two cases, a trans conformation around the C—C bond is observed. The lattice interactions in the crystal include packing of duplexes against each other via their minor grooves. Therefore, for some residues, the conformation of the 2'-O-substituent is affected by contacts to an adjacent duplex. In general, variations in the conformation of the substituents (e.g. g$^+$ or g$^−$ around the C—C bonds) create a range of interactions between substituents, both inter-strand, across the minor groove, and intra-strand. At one location, atoms of substituents from two residues are in van der Waals contact across the minor groove. Similarly, a close contact occurs between atoms of substituents from two adjacent intra-strand residues.

Previously determined crystal structures of A-DNA duplexes were for those that incorporated isolated 2'-O-methyl T residues. In the crystal structure noted above for the 2'-O-MOE substituents, a conserved hydration pattern has been observed for the 2'-O-MOE residues. A single water molecule is seen located between O2', O3' and the methoxy oxygen atom of the substituent, forming contacts to all three of between 2.9 and 3.4 Å. In addition, oxygen atoms of substituents are involved in several other hydrogen bonding contacts. For example, the methoxy oxygen atom of a particular 2'-O-substituent forms a hydrogen bond to N3 of an adenosine from the opposite strand via a bridging water molecule.

In several cases a water molecule is trapped between the oxygen atoms O2', O3' and OC' of modified nucleosides. 2'-O-MOE substituents with trans conformation around the C—C bond of the ethylene glycol linker are associated with close contacts between OC' and N2 of a guanosine from the opposite strand, and, water-mediated, between OC' and N3(G). When combined with the available thermodynamic data for duplexes containing 2'-O-MOE modified strands, this crystal structure allows for further detailed structure-stability analysis of other modifications.

In extending the crystallographic structure studies, molecular modeling experiments were performed to study further enhanced binding affinity of oligonucleotides having 2'-O-modifications. The computer simulations were conducted on compounds of SEQ ID NO: 10, above, having 2'-O-modifications located at each of the nucleosides of the oligonucleotide. The simulations were performed with the oligonucleotide in aqueous solution using the AMBER force field method (Cornell et al., *J. Am. Chem. Soc.,* 1995, 117, 5179-5197) (modeling software package from UCSF, San Francisco, Calif.). The calculations were performed on an Indigo2 SGI machine (Silicon Graphics, Mountain View, Calif.).

Further 2'-O-modifications that will have a 3'-endo sugar influence include those having a ring structure that incorporates a two atom portion corresponding to the A' and B' atoms of Structure II. The ring structure is attached at the 2' position of a sugar moiety of one or more nucleosides that are incorporated into an oligonucleotide. The 2'-oxygen of the nucleoside links to a carbon atom corresponding to the A' atom of Structure II. These ring structures can be aliphatic, unsaturated aliphatic, aromatic or heterocyclic. A further atom of the ring (corresponding to the B' atom of Structure II), bears a further oxygen atom, or a sulfur or nitrogen atom. This oxygen, sulfur or nitrogen atom is bonded to one or more hydrogen atoms, alkyl moieties, or haloalkyl moieties, or is part of a further chemical moiety such as a ureido, carbamate, amide or amidine moiety. The remainder of the ring structure restricts rotation about the bond joining these two ring atoms. This assists in positioning the "further oxygen, sulfur or nitrogen atom" (part of the R position as described above) such that the further atom can be located in close proximity to the 3'-oxygen atom (O3') of the nucleoside.

Another preferred 2'-sugar substituent group that gives a 3'-endo sugar conformational geometry is the 2'-OMe group. 2'-Substitution of guanosine, cytidine, and uridine dinucleoside phosphates with the 2'-OMe group showed enhanced stacking effects with respect to the corresponding native (2'-OH) species leading to the conclusion that the sugar is adopting a C3'-endo conformation. In this case, it is believed that the hydrophobic attractive forces of the methyl group tend to overcome the destabilizing effects of its steric bulk.

The ability of oligonucleotides to bind to their complementary target strands is compared by determining the melting temperature ($T_m$) of the hybridization complex of the oligonucleotide and its complementary strand. The melting temperature ($T_m$), a characteristic physical property of double helices, denotes the temperature (in degrees centigrade) at which 50% helical (hybridized) versus coil (unhybridized) forms are present. $T_m$ is measured by using the UV spectrum to determine the formation and breakdown (melting) of the hybridization complex. Base stacking, which occurs during hybridization, is accompanied by a reduction in UV absorption (hypochromicity). Consequently, a reduction in UV absorption indicates a higher $T_m$. The higher the $T_m$, the greater the strength of the bonds between the strands.

Freier and Altmann, Nucleic Acids Research, (1997) 25:4429-4443, have previously published a study on the influence of structural modifications of oligonucleotides on the stability of their duplexes with target RNA. In this study, the authors reviewed a series of oligonucleotides containing more than 200 different modifications that had been synthesized and assessed for their hybridization affinity and Tm. Sugar modifications studied included substitutions on the 2'-position of the sugar, 3'-substitution, replacement of the 4'-oxygen, the use of bicyclic sugars, and four member ring replacements. Several nucleobase modifications were also studied including substitutions at the 5, or 6 position of thymine, modifications of pyrimidine heterocycle and modifications of the purine heterocycle. Modified internucleoside linkages were also studied including neutral, phosphorus and non-phosphorus containing internucleoside linkages.

Increasing the percentage of C3'-endo sugars in a modified oligonucleotide targeted to an RNA target strand should preorganize this strand for binding to RNA. Of the several sugar modifications that have been reported and studied in the literature, the incorporation of electronegative substituents such as 2'-fluoro or 2'-alkoxy shift the sugar conformation towards the 3' endo (northern) pucker conformation. This preorganizes an oligonucleotide that incorporates such modifications to have an A-form conformational geometry. This A-form conformation results in increased binding affinity of the oligonucleotide to a target RNA strand.

Molecular modeling experiments were performed to study further enhanced binding affinity of oligonucleotides having 2'-O-modifications. Computer simulations were conducted on compounds having SEQ ID NO: 10, r(CGC GAA UUC GCG), having 2'-O-modifications of the invention located at each of the nucleoside of the oligonucleotide. The simulations were performed with the oligonucleotide in aqueous solution using the AMBER force field method (Cornell et al, *J. Am. Chem. Soc.,* 1995, 117, 5179-5197) (modeling software package from UCSF, San Francisco, Calif.). The calculations were performed on an Indigo2 SGI machine (Silicon Graphics, Mountain View, Calif.).

In addition, for 2'-substituents containing an ethylene glycol motif, a gauche interaction between the oxygen atoms around the O—C—C—O torsion of the side chain may have a stabilizing effect on the duplex (Freier ibid.). Such gauche interactions have been observed experimentally for a number of years (Wolfe et al., *Acc. Chem. Res.,* 1972, 5, 102; Abe et al., *J. Am. Chem. Soc.,* 1976, 98, 468). This gauche effect may result in a configuration of the side chain that is favorable for duplex formation. The exact nature of this stabilizing configuration has not yet been explained. While we do not want to be bound by theory, it may be that holding the O—C—C—O torsion in a single gauche configuration, rather than a more random distribution seen in an alkyl side chain, provides an entropic advantage for duplex formation.

Representative 2'-substituent groups amenable to the present invention that give A-form conformational properties (3'-endo) to the resultant duplexes include 2'-O-alkyl, 2'-O-substituted alkyl and 2'-fluoro substituent groups. Preferred for the substituent groups are various alkyl and aryl ethers and thioethers, amines and monoalkyl and dialkyl substituted amines. It is further intended that multiple modifications can be made to one or more of the oligomeric compounds of the invention at multiple sites of one or more monomeric subunits (nucleosides are preferred) and or internucleoside linkages to enhance properties such as but not limited to activity in a selected application. Tables I through VII list nucleoside and internucleotide linkage modifications/replacements that have been shown to give a positive εTm per modification when the modification/replacement was made to a DNA strand that was hybridized to an RNA complement.

TABLE I

Modified DNA strand having 2'-substituent groups that gave an overall increase in Tm against an RNA complement:

| | Positive ΔTm/mod |
|---|---|
| 2'-substituents | 2'-OH |
| | 2'-O—$C_1$-$C_4$ alkyl |
| | 2'-O—$(CH_2)_2CH_3$ |
| | 2'-O—$CH_2CH$=$CH_2$ |
| | 2'-F |
| | 2'-O—$(CH_2)_2$—O—$CH_3$ |
| | 2'-[O—$(CH_2)_2]_2$—O—$CH_3$ |
| | 2'-[O—$(CH_2)_2]_3$—O—$CH_3$ |
| | 2'-[O—$(CH_2)_2]_4$—O—$CH_3$ |
| | 2'-[O—$(CH_2)_2]_3$—O—$(CH_2)_8CH_3$ |
| | 2'-O—$(CH_2)_2CF_3$ |
| | 2'-O—$(CH_2)_2OH$ |
| | 2'-O—$(CH_2)_2F$ |
| | 2'-O—$CH_2CH(CH_3)F$ |
| | 2'-O—$CH_2CH(CH_2OH)OH$ |
| | 2'-O—$CH_2CH(CH_2OCH_3)OCH_3$ |
| | 2'-O—$CH_2CH(CH_3)OCH_3$ |
| | 2'-O—$CH_2$—$C_{14}H_7O_2$(—$C_{14}H_7O_2$ = Anthraquinone) |
| | 2'-O—$(CH_2)_3$—$NH_2$* |
| | 2'-O—$(CH_2)_4$—$NH_2$* |

*These modifications can increase the Tm of oligonucleotides but can also decrease the Tm depending on positioning and number (motiff dependant).

TABLE II

Modified DNA strand having modified sugar ring (see structure below) that gave an overall increase in Tm against an RNA complement:

Positive ΔTm/mod

| Q | —S— |
|---|---|
| | —$CH_2$— |

Note: In general ring oxygen substitution with sulfur or methylene had only a minor effect on Tm for the specific motiffs studied. Substitution at the 2'-position with groups shown to stabilize the duplex were destabilizing when $CH_2$ replaced the ring O. This is thought to be due to the necessary gauche interaction between the ring O with particular 2'-substituents (for example —O—$CH_3$ and —(O—$CH_2CH_2)_3$—O—$CH_3$.

TABLE III

Modified DNA strand having modified sugar ring that give an overall increase in Tm against an RNA complement:

TABLE III-continued

| | Positive ΔTm/mod |
|---|---|
| —C(H)$R_1$ effects | OH |
| ($R_2$, $R_3$ both = H) | $CH_3$* |
| | $CH_2OH$* |
| | $OCH_3$* |

*These modifications can increase the Tm of oligonucleotides but can also decrease the Tm depending on positioning and number (motiff dependant).

TABLE IV

Modified DNA strand having bicyclic substitute sugar modifications that give an overall increase in TM against an RNA complement:

| Formula | Positive ΔTm/mod |
|---|---|
| I | + |
| II | + |

TABLE V

Modified DNA strand having modified heterocyclic base moieties that give an overall increase in Tm against an RNA complement:

| Modification/Formula | Positive ΔTm/mod |
|---|---|
| Heterocyclic base modifications | 2-thioT |
| | 2'-O-methylpseudoU |
| | 7-halo-7-deaza purines |
| | 7-propyne-7-deaza purines |
| | 2-aminoA(2,6-diaminopurine) |

| ($R_2$, $R_3$ = H), $R_1$ = | Br |
|---|---|
| | C/C—$CH_3$ |
| | $(CH_2)_3NH_2$ |
| | $CH_3$ |

TABLE V-continued

Modified DNA strand having modified heterocyclic base moieties that give an overall increase in Tm against an RNA complement:

| | Positive ΔTm/mod |
|---|---|
| Motiffs-disubstitution | |
| $R_1$ = C/C—$CH_3$, $R_2$ = H, $R_3$ = | F |
| $R_1$ = C/C—$CH_3$, $R_2$ = H | $R_3$ = O—$(CH_2)_2$—O—$CH_3$ |
| $R_1$ = O—$CH_3$, $R_2$ = H, | $R_3$ = O—$(CH_2)_2$—O—$CH_3$* |

*This modification can increase the Tm of oligonucleotides but can also decrease the Tm depending on positioning and number (motiff dependant).

Substitution at $R_1$ can be stabilizing, substitution at $R_2$ is generally greatly destabilizing (unable to form anti conformation), motiffs with stabilizing 5 and 2'-substituent groups are generally additive e.g. increase stability.

Substitution of the O4 and O2 positions of 2'-O-methyl uridine was greatly duplex destabilizing as these modifications remove hydrogen binding sites that would be an expected result. 6-Aza T also showed extreme destabilization as this substitution reduces the $pK_a$ and shifts the nucleoside toward the enol tautomer resulting in reduced hydrogen bonding.

TABLE VI m DNA strand having at least one modified phosphorus containing internucleoside linkage and the effect on the Tm against an RNA complement:

| ΔTm/mod+ | ΔTm/mod− |
|---|---|
| phosphoramidate (the 3'-bridging atom replaced with an N(H)R group, stabilization effect enhanced when also have 2'-F) | phosphorothioate[1] phosphoramidate[1] methyl phosphonates[1] ([1] one of the non-bridging oxygen atoms replaced with S, N(H)R or —$CH_3$) |

TABLE VII

DNA strand having at least one non-phosphorus containing internucleoside linkage and the effect on the Tm against an RNA complement Positive ΔTm/mod —$CH_2C$(=O)$NHCH_2$—*
—$CH_2C$(=O)$N(CH_3)CH_2$—*
—$CH_2C$(=O)$N(CH_2CH_2CH_3)CH_2$—*
—$CH_2C$(=O)$N(H)CH_2$—(motiff with 5'-propyne on T's)
—$CH_2N(H)C$(=O)$CH_2$—*
—$CH_2N(CH_3)OCH_2$—*
—$CH_2N(CH_3)N(CH_3)CH_2$—*

*This modification can increase the Tm of oligonucleotides but can also decrease the Tm depending on positioning and number (motiff dependant).

Notes: In general carbon chain internucleotide linkages were destabilizing to duplex formation. This destabilization was not as severe when double and tripple bonds were utilized. The use of glycol and flexible ether linkages were also destabilizing.

Preferred ring structures of the invention for inclusion as a 2'-O modification include cyclohexyl, cyclopentyl and phenyl rings as well as heterocyclic rings having spacial footprints similar to cyclohexyl, cyclopentyl and phenyl rings. Particularly preferred 2'-O-substituent groups of the invention are listed below including an abbreviation for each:

| 2'-O-(trans 2-methoxy cyclohexyl) | 2'-O-(TMCHL) |
|---|---|
| 2'-O-(trans 2-methoxy cyclopentyl) | 2'-O-(TMCPL) |
| 2'-O-(trans 2-ureido cyclohexyl) | 2'-O-(TUCHL) |
| 2'-O-(trans 2-methoxyphenyl) | 2'-O-(2MP) |

Structural details for duplexes incorporating such 2-O-substituents were analyzed using the described AMBER force field program on the Indigo2 SGI machine. The simulated structure maintained a stable A-form geometry throughout the duration of the simulation. The presence of the 2' substitutions locked the sugars in the C3'-endo conformation.

The simulation for the TMCHL modification revealed that the 2'-O-(TMCHL) side chains have a direct interaction with water molecules solvating the duplex. The oxygen atoms in the 2'-O-(TMCHL) side chain are capable of forming a water-mediated interaction with the 3' oxygen of the phosphate backbone. The presence of the two oxygen atoms in the 2'-O-(TMCHL) side chain gives rise to favorable gauche interactions. The barrier for rotation around the O—C—C—O torsion is made even larger by this novel modification. The preferential preorganization in an A-type geometry increases the binding affinity of the 2'-O-(TMCHL) to the target RNA. The locked side chain conformation in the 2'-O-(TMCHL) group created a more favorable pocket for binding water molecules. The presence of these water molecules played a key role in holding the side chains in the preferable gauche conformation. While not wishing to be bound by theory, the bulk of the substituent, the diequatorial orientation of the substituents in the cyclohexane ring, the water of hydration and the potential for trapping of metal ions in the conformation generated will additionally contribute to improved binding affinity and nuclease resistance of oligonucleotides incorporating nucleosides having this 2'-O-modification.

As described for the TMCHL modification above, identical computer simulations of the 2'-O-(TMCPL), the 2'-O-(2 MP) and 2'-O-(TUCHL) modified oligonucleotides in aqueous solution also illustrate that stable A-form geometry will be maintained throughout the duration of the simulation. The presence of the 2' substitution will lock the sugars in the C3'-endo conformation and the side chains will have direct interaction with water molecules solvating the duplex. The oxygen atoms in the respective side chains are capable of forming a water-mediated interaction with the 3' oxygen of the phosphate backbone. The presence of the two oxygen atoms in the respective side chains give rise to the favorable gauche interactions. The barrier for rotation around the respective O—C—C—O torsions will be made even larger by respective modification. The preferential preorganization in A-type geometry will increase the binding affinity of the respective 2'-O-modified oligonucleotides to the target RNA. The locked side chain conformation in the respective modifications will create a more favorable pocket for binding water molecules. The presence of these water molecules plays a key role in holding the side chains in the preferable gauche conformation. The bulk of the substituent, the diequatorial orientation of the substituents in their respective rings, the water of hydration and the potential trapping of metal ions in the conformation generated will all contribute to improved binding affinity and nuclease resistance of oligonucleotides incorporating nucleosides having these respective 2'-O-modification.

Ribose conformations in C2'-modified nucleosides containing S-methyl groups were examined. To understand the influence of 2'-O-methyl and 2'-S-methyl groups on the conformation of nucleosides, we evaluated the relative energies of the 2'-O- and 2'-S-methylguanosine, along with normal deoxyguanosine and riboguanosine, starting from both C2'-endo and C3'-endo conformations using ab initio quantum mechanical calculations. All the structures were fully optimized at HF/6-31G* level and single point energies with electron-correlation were obtained at the MP2/6-31G*//HF/6-31G* level. As shown in Table VIII, the C2'-endo conformation of deoxyguanosine is estimated to be 0.6 kcal/mol more stable than the C3'-endo conformation in the gas-phase. The conformational preference of the C2'-endo over the C3'-endo conformation appears to be less dependent upon electron correlation as revealed by the MP2/6-31G*//HF/6-31G* values which also predict the same difference in energy. The opposite trend is noted for riboguanosine. At the HF/6-31G* and MP2/6-31G*//HF/6-31G* levels, the C3'-endo form of riboguanosine is shown to be about 0.65 and 1.41 kcal/mol more stable than the C2'endo form, respectively.

TABLE VIII

Relative energies* of the C3'-endo and C2'-endo conformations of representative nucleosides.

|  | HF/6-31G | MP2/6-31-G | CONTINUUM MODEL | AMBER |
| --- | --- | --- | --- | --- |
| dG | 0.60 | 0.56 | 0.88 | 0.65 |
| rG | −0.65 | −1.41 | −0.28 | −2.09 |
| 2'-O-MeG | −0.89 | −1.79 | −0.36 | −0.86 |
| 2'-S-MeG | 2.55 | 1.41 | 3.16 | 2.43 |

*energies are in kcal/mol relative to the C2'-endo conformation

Table VIII also includes the relative energies of 2'-O-methylguariosine and 2'-S-methylguanosine in C2'-endo and C3'-endo conformation. This data indicates the electronic nature of C2'-substitution has a significant impact on the relative stability of these conformations. Substitution of the 2'-O-methyl group increases the preference for the C3'-endo conformation (when compared to riboguanosine) by about 0.4 kcal/mol at both the HF/6-31G* and MP2/6-31G*//HF/6-31G* levels. In contrast, the 2'-S-methyl group reverses the trend. The C2'-endo conformation is favored by about 2.6 kcal/mol at the HF/6-31G* level, while the same difference is reduced to 1.41 kcal/mol at the MP2/6-31G*//HF/6-31G* level. For comparison, and also to evaluate the accuracy of the molecular mechanical force-field parameters used for the 2'-O-methyl and 2'-S-methyl substituted nucleosides, we have calculated the gas phase energies of the nucleosides. The results reported in Table 1 indicate that the calculated relative energies of these nucleosides compare qualitatively well with the ab initio calculations.

Additional calculations were also performed to gauge the effect of salvation on the relative stability of nucleoside conformations. The estimated solvation effect using HF/6-31G* geometries confirms that the relative energetic preference of the four nucleosides in the gas-phase is maintained in the aqueous phase as well (Table 1). Solvation effects were also examined using molecular dynamics simulations of the nucleosides in explicit water. From these trajectories, one can observe the predominance of C2'-endo conformation for deoxyriboguanosine and 2'-S-methylriboguanosine while riboguanosine and 2'-O-methylriboguanosine prefer the C3'-endo conformation. These results are in much accord with the available NMR results on 2'-S-methylribonucleosides. NMR studies of sugar puckering equilibrium using vicinal spin-coupling constants have indicated that the conformation of the sugar ring in 2'-S-methylpyrimidine nucleosides show an average of >75% S-character, whereas the corresponding purine analogs exhibit an average of >90% S-pucker [Fraser, A., Wheeler, P., Cook, P. D. and Sanghvi, Y. S., *J. Heterocycl. Chem.*, 1993, 30, 1277-1287]. It was observed that the 2'-S-methyl substitution in deoxynucleoside confers more conformational rigidity to the sugar conformation when compared with deoxyribonucleosides.

Structural features of DNA:RNA, OMe-DNA:RNA and SMe-DNA:RNA hybrids were also observed. The average RMS deviation of the DNA:RNA structure from the starting hybrid coordinates indicate the structure is stabilized over the length of the simulation with an approximate average RMS deviation of 1.0 Å. This deviation is due, in part, to inherent differences in averaged structures (i.e. the starting conformation) and structures at thermal equilibrium. The changes in sugar pucker conformation for three of the central base pairs of this hybrid are in good agreement with the observations made in previous NMR studies. The sugars in the RNA strand maintain very stable geometries in the C3'-endo conformation with ring pucker values near 0°. In contrast, the sugars of the DNA strand show significant variability.

The average RMS deviation of the OMe-DNA:RNA is approximately 1.2 Å from the starting A-form conformation; while the SMe-DNA:RNA shows a slightly higher deviation (approximately 1.8 Å) from the starting hybrid conformation. The SMe-DNA strand also shows a greater variance in RMS deviation, suggesting the S-methyl group may induce some structural fluctuations. The sugar puckers of the RNA complements maintain C3'-endo puckering throughout the simulation. As expected from the nucleoside calculations, however, significant differences are noted in the puckering of the OMe-DNA and SMe-DNA strands, with the former adopting C3'-endo, and the latter, C1'-exo/C2'-endo conformations.

An analysis of the helicoidal parameters for all three hybrid structures has also been performed to further characterize the duplex conformation. Three of the more important axis-base-pair parameters that distinguish the different forms of the duplexes, X-displacement, propeller twist, and inclination, are reported in Table 2. Usually, an X-displacement near zero represents a B-form duplex; while a negative displacement, which is a direct measure of deviation of the helix from the helical axis, makes the structure appear more A-like in conformation. In A-form duplexes, these values typically vary from −4 Å to −5 Å. In comparing these values for all three hybrids, the SMe_DNA:RNA hybrid shows the most deviation from the A-form value, the OMe_DNA:RNA shows the least, and the DNA:RNA is intermediate. A similar trend is also evident when comparing the inclination and propeller twist values with ideal A-form parameters. These results are further supported by an analysis of the backbone and glycosidic torsion angles of the hybrid structures. Glycosidic angles (X) of A-form geometries, for example, are typically near −159° while B form values are near −102°. These angles are found to be −162°, −133°, and −108° for the OMe-DNA, DNA, and SMe-DNA strands, respectively. All RNA complements adopt an X angle close to −160°. In addition, "crankshaft" transitions were also noted in the backbone torsions of the central UpU steps of the RNA strand in the SMe-DNA:RNA and DNA;RNA hybrids. Such transitions suggest some local conformational changes may occur to relieve a less favorable global conformation. Taken overall, the results indicate the amount of A-character decreases as OMe-DNA:RNA>DNA:RNA>SMe-DNA:RNA, with the latter two adopting more intermediate conformations when compared to A- and B-form geometries.

TABLE IX

Average helical parameters derived from the last 500 ps of simulation time
(canonical A-and B-form values are given for comparison)

| Helicoidal Parameter | B-DNA (x-ray) | B-DNA (fibre) | A-DNA (fibre) | DNA:RNA | OMe_DNA:RNA | SMe_DNA:RNA |
|---|---|---|---|---|---|---|
| X-disp | 1.2 | 0.0 | −5.3 | −4.5 | −5.4 | −3.5 |
| Inclination | −2.3 | 1.5 | 20.7 | 11.6 | 15.1 | 0.7 |
| Propeller | −16.4 | −13.3 | −7.5 | −12.7 | −15.8 | −10.3 |

Stability of C2'-modified DNA:RNA hybrids was determined. Although the overall stability of the DNA:RNA hybrids depends on several factors including sequence-dependencies and the purine content in the DNA or RNA strands DNA:RNA hybrids are usually less stable than RNA:RNA duplexes and, in some cases, even less stable than DNA:DNA duplexes. Available experimental data attributes the relatively lowered stability of DNA:RNA hybrids largely to its intermediate conformational nature between DNA:DNA (B-family) and RNA:RNA (A-family) duplexes. The overall thermodynamic stability of nucleic acid duplexes may originate from several factors including the conformation of backbone, base-pairing and stacking interactions. While it is difficult to ascertain the individual thermodynamic contributions to the overall stabilization of the duplex, it is reasonable to argue that the major factors that promote increased stability of hybrid duplexes are better stacking interactions (electrostatic π-π interactions) and more favorable groove dimensions for hydration. The C2'-S-methyl substitution has been shown to destabilize the hybrid duplex. The notable differences in the rise values among the three hybrids may offer some explanation. While the 2'-S-methyl group has a strong influence on decreasing the base-stacking through high rise values (~3.2 Å), the 2'-O-methyl group makes the overall structure more compact with a rise value that is equal to that of A-form duplexes (~2.6 Å). Despite its overall A-like structural features, the SMe_DNA:RNA hybrid structure possesses an average rise value of 3.2 Å which is quite close to that of B-family duplexes. In fact, some local base-steps (CG steps) may be observed to have unusually high rise values (as high as 4.5 Å). Thus, the greater destabilization of 2'-S-methyl substituted DNA:RNA hybrids may be partly attributed to poor stacking interactions.

It has been postulated that RNase H binds to the minor groove of RNA:DNA hybrid complexes, requiring an intermediate minor groove width between ideal A- and B-form geometries to optimize interactions between the sugar phosphate backbone atoms and RNase H. A close inspection of the averaged structures for the hybrid duplexes using computer simulations reveals significant variation in the minor groove width dimensions as shown in Table 3. Whereas the O-methyl substitution leads to a slight expansion of the minor groove width when compared to the standard DNA:RNA complex, the S-methyl substitution leads to a general contraction (approximately 0.9 Å). These changes are most likely due to the preferred sugar puckering noted for the antisense strands which induce either A- or B-like single strand conformations. In addition to minor groove variations, the results also point to potential differences in the steric makeup of the minor groove. The O-methyl group points into the minor groove while the S-methyl is directed away towards the major groove. Essentially, the S-methyl group has flipped through the bases into the major groove as a consequence of C2'-endo puckering.

TABLE X

Minor groove widths averaged over the last 500 ps of simulation time

| Phosphate Distance | DNA:RNA | OMe_DNA:RNA | SMe_DNA:RNA | DNA:RNA (B-form) | RNA:RNA (A-form) |
|---|---|---|---|---|---|
| P5-P20 | 15.27 | 16.82 | 13.73 | 14.19 | 17.32 |
| P6-P19 | 15.52 | 16.79 | 15.73 | 12.66 | 17.12 |
| P7-P18 | 15.19 | 16.40 | 14.08 | 11.10 | 16.60 |
| P8-P17 | 15.07 | 16.12 | 14.00 | 10.98 | 16.14 |
| P9-P16 | 15.29 | 16.25 | 14.98 | 11.65 | 16.93 |
| P10-P15 | 15.37 | 16.57 | 13.92 | 14.05 | 17.69 |

Chemistries Defined

Unless otherwise defined herein, alkyl means $C_1$-$C_{12}$, preferably $C_1$-$C_8$, and more preferably $C_1$-$C_6$, straight or (where possible) branched chain aliphatic hydrocarbyl.

Unless otherwise defined herein, heteroalkyl means $C_1$-$C_{32}$, preferably $C_1$-$C_8$, and more preferably $C_1$-$C_6$, straight or (where possible) branched chain aliphatic hydrocarbyl containing at least one, and preferably about 1 to about 3, hetero atoms in the chain, including the terminal portion of the chain. Preferred heteroatoms include N, O and S.

Unless otherwise defined herein, cycloalkyl means $C_3$-$C_{12}$, preferably $C_3$-$C_8$, and more preferably $C_3$-$C_6$, aliphatic hydrocarbyl ring.

Unless otherwise defined herein, alkenyl means $C_2$-$C_{12}$, preferably $C_2$-$C_8$, and more preferably $C_2$-$C_6$ alkenyl, which may be straight or (where possible) branched hydrocarbyl moiety, which contains at least one carbon-carbon double bond.

Unless otherwise defined herein, alkynyl means $C_2$-$C_{12}$, preferably $C_2$-$C_8$, and more preferably $C_2$-$C_6$ alkynyl, which may be straight or (where possible) branched hydrocarbyl moiety, which contains at least one carbon-carbon triple bond.

Unless otherwise defined herein, heterocycloalkyl means a ring moiety containing at least three ring members, at least one of which is carbon, and of which 1, 2 or three ring members are other than carbon. Preferably the number of carbon atoms varies from 1 to about 12, preferably 1 to about 6, and the total number of ring members varies from three to about 15, preferably from about 3 to about 8. Preferred ring heteroatoms are N, O and S. Preferred heterocycloalkyl groups include morpholino, thiomorpholino, piperidinyl, piperazinyl, homopiperidinyl, homopiperazinyl, homomorpholino, homothiomorpholino, pyrrolodinyl, tetrahydrooxazolyl, tetrahydroimidazolyl, tetrahydrothiazolyl, tetrahydroisoxazolyl, tetrahydropyrrazolyl, furanyl, pyranyl, and tetrahydroisothiazolyl.

Unless otherwise defined herein, aryl means any hydrocarbon ring structure containing at least one aryl ring. Preferred aryl rings have about 6 to about 20 ring carbons. Especially preferred aryl rings include phenyl, napthyl, anthracenyl, and phenanthrenyl.

Unless otherwise defined herein, heteroaryl means a ring moiety containing at least one fully unsaturated ring, the ring consisting of carbon and non-carbon atoms. Preferably the ring system contains about 1 to about 4 rings. Preferably the number of carbon atoms varies from 1 to about 12, preferably 1 to about 6, and the total number of ring members varies from three to about 15, preferably from about 3 to about 8. Preferred ring heteroatoms are N, O and S. Preferred heteroaryl moieties include pyrazolyl, thiophenyl, pyridyl, imidazolyl, tetrazolyl, pyridyl, pyrimidinyl, purinyl, quinazolinyl, quinoxalinyl, benzimidazolyl, benzothiophenyl, etc.

Unless otherwise defined herein, where a moiety is defined as a compound moiety, such as heteroarylalkyl (heteroaryl and alkyl), aralkyl (aryl and alkyl), etc., each of the sub-moieties is as defined herein.

Unless otherwise defined herein, an electron withdrawing group is a group, such as the cyano or isocyanato group that draws electronic charge away from the carbon to which it is attached. Other electron withdrawing groups of note include those whose electronegativities exceed that of carbon, for example halogen, nitro, or phenyl substituted in the ortho- or para-position with one or more cyano, isothiocyanato, nitro or halo groups.

Unless otherwise defined herein, the terms halogen and halo have their ordinary meanings. Preferred halo (halogen) substituents are Cl, Br, and I.

The aforementioned optional substituents are, unless otherwise herein defined, suitable substituents depending upon desired properties. Included are halogens (F, Cl, Br, I), alkyl, alkenyl, and alkynyl moieties, $NO_2$, $NH_3$ (substituted and unsubstituted), acid moieties (e.g. —$CO_2H$, —$OSO_3H_2$, etc.), heterocycloalkyl moieties, hetaryl moieties, aryl moieties, etc.

Phosphate protecting groups include those described in U.S. Pat. No. 5,760,209, U.S. Pat. No. 5,614,621, U.S. Pat. No. 6,051,699, U.S. Pat. No. 6,020,475, U.S. Pat. No. 6,326,478, U.S. Pat. No. 6,169,177, U.S. Pat. No. 6,121,437, U.S. Pat. No. 6,465,628 each of which is expressly incorporated herein by reference in its entirety.

Oligomer Synthesis

Oligomerization of modified and unmodified nucleosides is performed according to literature procedures for DNA (Protocols for Oligonucleotides and Analogs, Ed. Agrawal (1993), Humana Press) and/or RNA (Scaringe, Methods (2001), 23, 206-217. Gait et al., Applications of Chemically synthesized RNA in RNA:Protein Interactions, Ed. Smith (1998), 1-36. Gallo et al., Tetrahedron (2001), 57, 5707-5713) synthesis as appropriate. In addition specific protocols for the synthesis of oligomeric compounds of the invention are illustrated in the examples below.

The oligomeric compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The present invention is also useful for the preparation of oligomeric compounds incorporating at least one 2'-O-protected nucleoside. After incorporation and appropriate deprotection the 2'-O-protected nucleoside will be converted to a ribonucleoside at the position of incorporation. The number and position of the 2-ribonucleoside units in the final oligomeric compound can vary from one at any site or the strategy can be used to prepare up to a full 2'-OH modified oligomeric compound. All 2'-O-protecting groups amenable to the synthesis of oligomeric compounds are included in the present invention. In general a protected nucleoside is attached to a solid support by for example a succinate linker. Then the oligonucleotide is elongated by repeated cycles of deprotecting the 5'-terminal hydroxyl group, coupling of a further nucleoside unit, capping and oxidation (alternatively sulfurization). In a more frequently used method of synthesis the completed oligonucleotide is cleaved from the solid support with the removal of phosphate protecting groups and exocyclic amino protecting groups by treatment with an ammonia solution. Then a further deprotection step is normally require d for removal of the more specialized protecting groups used for the protection of 2'-hydroxyl groups thereby affording the fully deprotected oligonucleotide.

A large number of 2'-O-protecting groups have been used for the synthesis of oligoribonucleotides but over the years more effective groups have been discovered. The key to an effective 2'-O-protecting group is that it is capable of selectively being introduced at the 2'-O-position and that it can be removed easily after synthesis without the formation of unwanted side products. The protecting group also needs to be inert to the normal deprotecting, coupling, and capping steps required for oligoribonucleotide synthesis. Some of the protecting groups used initially for oligoribonucleotide synthesis included tetrahydropyran-1-yl and 4-methoxytetrahydropyran-4-yl. These two groups are not compatible with all 5'-O-protecting groups so modified versions were used with 5'-DMT groups such as 1-(2-fluorophenyl)-4-methoxypiperidin-4-yl (Fpmp). Reese has identified a number of piperidine derivatives (like Fpmp) that are useful in the synthesis of oligoribonucleotides including 1-[(chloro-4-methyl)-phenyl]-4'-methoxypiperidin-4-yl (Reese et al., Tetrahedron Lett., 1986, (27), 2291). Another approach was to replace the standard 5'-DMT (dimethoxytrityl) group with protecting groups that were removed under non-acidic conditions such as levulinyl and 9-fluorenylmethoxycarbonyl. Such groups enable the use of acid labile 2'-protecting groups for oligoribonucleotide synthesis. Another more widely used protecting group initially used for the synthesis of oligoribonucleotides was the t-butyldimethylsilyl group (Ogilvie et al., Tetrahedron Lett., 1974, 2861; Hakimelahi et al., Tetrahedron Lett., 1981, (22), 2543; and Jones et al., J. Chem. Soc. Perkin I., 2762). The 2'-O-protecting groups can require special reagents for their removal such as for example the t-butyldimethylsilyl group is normally removed after all other cleaving/deprotecting steps by treatment of the oligomeric compound with tetrabutylammonium fluoride (TBAF).

One group of researchers examined a number of 2'-O-protecting groups (Pitsch, S., Chimia, 2001, (55), 320-324.) The group examined fluoride labile and photolabile protecting groups that are removed using moderate conditions. One photolabile group that was examined was the [2-(nitrobenzyl)

oxy]methyl (nbm) protecting group (Schwartz et al., Bioorg. Med. Chem. Lett., 1992, (2), 1019.) Other groups examined included a number structurally related formaldehyde acetal-derived, 2'-O-protecting groups. Also prepared were a number of related protecting groups for preparing 2'-O-alkylated nucleoside phosphoramidites including 2'-O-[(triisopropylsilyl)oxy]methyl (2'-O—CH$_2$—O—Si(iPr)$_3$, TOM). One 2'-O-protecting group that was prepared to be used orthogonally to the TOM group was 2'-O—[(R)-1-(2-nitrophenyl)ethyloxy)methyl] ((R)-mnbm).

Another strategy using a fluoride labile 5'-O-protecting group (non-acid labile) and an acid labile 2'-O-protecting group has been reported (Scaringe, Stephen A., Methods, 2001, (23) 206-217). A number of possible silyl ethers were examined for 5'-O-protection and a number of acetals and orthoesters were examined for 2'-O-protection. The protection scheme that gave the best results was 5'-O-silyl ether-2'-ACE (5'-O-bis(trimethylsiloxy)cyclododecyloxysilyl ether (DOD)-2'-O-bis(2-acetoxyethoxy)methyl (ACE). This approach uses a modified phosphoramidite synthesis approach in that some different reagents are required that are not routinely used for RNA/DNA synthesis.

Although a lot of research has focused on the synthesis of oligoribonucleotides the main RNA synthesis strategies that are presently being used commercially include 5'-O-DMT-2'-O-t-butyldimethylsilyl (TBDMS), 5'-O-DMT-2'-O-[1(2-fluorophenyl)-4-methoxypiperidin-4-yl] (FPMP), 2'-O-[(triisopropylsilyl)oxy]methyl (2'-O—CH$_2$—O—Si(iPr)$_3$ (TOM), and the 5'-O-silyl ether-2'-ACE (5'-O-bis(trimethylsiloxy)cyclododecyloxysilyl ether (DOD)-2'-O-bis(2-acetoxyethoxy)methyl (ACE). A current list of some of the major companies currently offering RNA products include Pierce Nucleic Acid Technologies, Dharmacon Research Inc., Ameri Biotechnologies Inc., and Integrated DNA Technologies, Inc. One company, Princeton Separations, is marketing an RNA synthesis activator advertised to reduce coupling times especially with TOM and TBDMS chemistries. Such an activator would also be amenable to the present invention.

The primary groups being used for commercial RNA synthesis are:
TBDMS=5'-O-DMT-2'-O-t-butyldimethylsilyl;
TOM=2'-O-[(triisopropylsilyl)oxy]methyl;
DOD/ACE=(5'-O-bis(trimethylsiloxy)cyclododecyloxysilyl ether-2'-O-bis(2-acetoxyethoxy)methyl
FPMP=5'-O-DMT-2'-O-[1(2-fluorophenyl)-4-methoxypiperidin-4-yl].

All of the aforementioned RNA synthesis strategies are amenable to the present invention. Strategies that would be a hybrid of the above e.g. using a 5'-protecting group from one strategy with a 2'-O-protecting from another strategy is also amenable to the present invention.

The preparation of ribonucleotides and oligomeric compounds having at least one ribonucleoside incorporated and all the possible configurations falling in between these two extremes are encompassed by the present invention. The corresponding oligomeric compounds can be hybridized to further oligomeric compounds including oligoribonucleotides having regions of complementarity to form double-stranded (duplexed) oligomeric compounds. Such double stranded oligonucleotide moieties have been shown in the art to modulate target expression and regulate translation as well as RNA processsing via an antisense mechanism. Moreover, the double-stranded moieties may be subject to chemical modifications (Fire et al., Nature, 1998, 391, 806-811; Timmons and Fire, Nature 1998, 395, 854; Timmons et al., Gene, 2001, 263, 103-112; Tabara et al., Science, 1998, 282, 430-431; Montgomery et al., Proc. Natl. Acad. Sci. USA, 1998, 95, 15502-15507; Tuschl et al., Genes Dev., 1999, 13, 3191-3197; Elbashir et al., Nature, 2001, 411, 494-498; Elbashir et al., Genes Dev. 2001, 15, 188-200). For example, such double-stranded moieties have been shown to inhibit the target by the classical hybridization of antisense strand of the duplex to the target, thereby triggering enzymatic degradation of the target (Tijsterman et al., Science, 2002, 295, 694-697).

The methods of preparing oligomeric compounds of the present invention can also be applied in the areas of drug discovery and target validation. The present invention comprehends the use of the oligomeric compounds and preferred targets identified herein in drug discovery efforts to elucidate relationships that exist between proteins and a disease state, phenotype, or condition. These methods include detecting or modulating a target peptide comprising contacting a sample, tissue, cell, or organism with the oligomeric compounds of the present invention, measuring the nucleic acid or protein level of the target and/or a related phenotypic or chemical endpoint at some time after treatment, and optionally comparing the measured value to a non-treated sample or sample treated with a further oligomeric compound of the invention. These methods can also be performed in parallel or in combination with other experiments to determine the function of unknown genes for the process of target validation or to determine the validity of a particular gene product as a target for treatment or prevention of a particular disease, condition, or phenotype.

Effect of nucleoside modifications on RNAi activity is evaluated according to existing literature (Elbashir et al., Nature (2001), 411, 494-498; Nishikura et al., Cell (2001), 107, 415-416; and Bass et al., Cell (2000), 101, 235-238.)

Targets of the Invention

"Targeting" an antisense oligomeric compound to a particular nucleic acid molecule, in the context of this invention, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent.

The targeting process usually also includes determination of at least one target region, segment, or site within the target nucleic acid for the antisense interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid. The terms region, segment, and site can also be used to describe an oligomeric compound of the invention such as for example a gapped oligomeric compound having 3 separate segments.

Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes)

or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding a nucleic acid target, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions which may be targeted effectively with the antisense oligomeric compounds of the present invention.

The open reading frame (ORF) or "coding region," which is known in the art to refer to the region between the translation initiation codon and the translation termination codon, is also a region which may be targeted effectively. Within the context of the present invention, a preferred region is the intragenic region encompassing the translation initiation or termination codon of the open reading frame (ORF) of a gene.

Other target regions include the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene), and the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. It is also preferred to target the 5' cap region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. Targeting splice sites, i.e., intron-exon junctions or exon-intron junctions, may also be particularly useful in situations where aberrant splicing is implicated in disease, or where an overproduction of a particular splice product is implicated in disease. Aberrant fusion junctions due to rearrangements or deletions are also preferred target sites. mRNA transcripts produced via the process of splicing of two (or more) mRNAs from different gene sources are known as "fusion transcripts". It is also known that introns can be effectively targeted using antisense oligomeric compounds targeted to, for example, DNA or pre-mRNA.

It is also known in the art that alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequences.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also preferred target nucleic acids.

The locations on the target nucleic acid to which the preferred antisense oligomeric compounds hybridize are hereinbelow referred to as "preferred target segments." As used herein the term "preferred target segment" is defined as at least an 8-nucleobase portion of a target region to which an active antisense oligomeric compound is targeted. While not wishing to be bound by theory, it is presently believed that these target segments represent accessible portions of the target nucleic acid for hybridization.

Exemplary preferred antisense oligomeric compounds include oligomeric compounds that comprise at least the 8 consecutive nucleobases from the 5'-terminus of a targeted nucleic acid e.g. a cellular gene or mRNA transcribed from the gene (the remaining nucleobases being a consecutive stretch of the same oligonucleotide beginning immediately upstream of the 5'-terminus of the antisense compound which is specifically hybridizable to the target nucleic acid and continuing until the oligonucleotide contains from about 8 to about 80 nucleobases). Similarly preferred antisense oligomeric compounds are represented by oligonucleotide sequences that comprise at least the 8 consecutive nucleobases from the 3'-terminus of one of the illustrative preferred antisense compounds (the remaining nucleobases being a consecutive stretch of the same oligonucleotide beginning immediately downstream of the 3'-terminus of the antisense compound which is specifically hybridizable to the target nucleic acid and continuing until the oligonucleotide contains from about 8 to about 80 nucleobases). One having skill in the art armed with the preferred antisense compounds illustrated herein will be able, without undue experimentation, to identify further preferred antisense compounds.

Once one or more target regions, segments or sites have been identified, antisense oligomeric compounds are chosen which are sufficiently complementary to the target, i.e., hybridize sufficiently well and with sufficient specificity, to give the desired effect.

In accordance with one embodiment of the present invention, a series of preferred compositions of nucleic acid duplexes comprising the antisense oligomeric compounds of the present invention and their complements can be designed for a specific target or targets. The ends of the strands may be modified by the addition of one or more natural or modified nucleobases to form an overhang. The sense strand of the duplex is then designed and synthesized as the complement of the antisense strand and may also contain modifications or additions to either terminus. For example, in one embodiment, both strands of the duplex would be complementary over the central nucleobases, each having overhangs at one or both termini.

For example, a duplex comprising an antisense oligomeric compound having the sequence CGAGAGGCGGACGG-GACCG (SEQ ID NO:12) and having a two-nucleobase overhang of deoxythymidine (dT) would have the following structure:

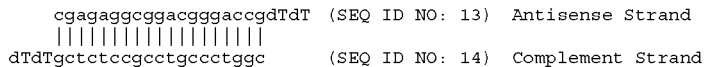

```
cgagaggcggacgggaccgdTdT  (SEQ ID NO: 13)  Antisense Strand
|||||||||||||||||||
dTdTgctctccgcctgccctggc  (SEQ ID NO: 14)  Complement Strand
```

RNA strands of the duplex can be synthesized by methods disclosed herein or purchased from various RNA synthesis companies such as for example Dharmacon Research Inc., (Lafayette, Colo.). Once synthesized, the complementary strands are annealed. The single strands are aliquoted and diluted to a concentration of 50 uM. Once diluted, 30 uL of each strand is combined with 15 uL of a 5× solution of annealing buffer. The final concentration of the buffer is 100 mM potassium acetate, 30 mM HEPES-KOH pH 7.4, and 2 mM magnesium acetate. The final volume is 75 uL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA compound is 20 uM. This solution can be stored frozen (−20° C.) and freeze-thawed up to 5 times.

Once prepared, the desired synthetic duplexes are evaluated for their ability to modulate target expression. When cells reach 80% confluency, they are treated with synthetic duplexes comprising at least one oligomeric compound of the invention. For cells grown in 96-well plates, wells are washed once with 200 μL OPTI-MEM-1 reduced-serum medium (Gibco BRL) and then treated with 130 μL of OPTI-MEM-1 containing 12 μg/mL LIPOFECTIN (Gibco BRL) and the desired dsRNA compound at a final concentration of 200 nM. After 5 hours of treatment, the medium is replaced with fresh medium. Cells are harvested 16 hours after treatment, at which time RNA is isolated and target reduction measured by RT-PCR.

In a further embodiment, the "preferred target segments" identified herein may be employed in a screen for additional oligomeric compounds that modulate the expression of a target. "Modulators" are those oligomeric compounds that decrease or increase the expression of a nucleic acid molecule encoding a target and which comprise at least an 8-nucleobase portion which is complementary to a preferred target segment. The screening method comprises the steps of contacting a preferred target segment of a nucleic acid molecule encoding a target with one or more candidate modulators, and selecting for one or more candidate modulators which decrease or increase the expression of a nucleic acid molecule encoding a target. Once it is shown that the candidate modulator or modulators are capable of modulating (e.g. either decreasing or increasing) the expression of a nucleic acid molecule encoding a target, the modulator may then be employed in further investigative studies of the function of a target, or for use as a research, diagnostic, or therapeutic agent in accordance with the present invention.

The preferred target segments of the present invention may also be combined with their respective complementary antisense oligomeric compounds of the present invention to form stabilized double-stranded (duplexed) oligonucleotides.

Hybridization

In the context of this invention, "hybridization" occurs when two sequences come together with enough base complementarity to form a double stranded region. The source of the two sequences can be synthetic or native and can occur in a single strand when the strand has regions of self complementarity. In the present invention, the preferred mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds or between an oligomeric compound and a target nucleic acid. For example, adenine and thymine are complementary nucleobases which pair through the formation of hydrogen bonds. Hybridization can occur under varying circumstances.

An antisense oligomeric compound is specifically hybridizable when binding of the compound to the target nucleic acid interferes with the normal function of the target nucleic acid to cause a loss of activity, and there is a sufficient degree of complementarity to avoid non-specific binding of the antisense oligomeric compound to non-target nucleic acid sequences under conditions in which specific binding is desired, i.e., under physiological conditions in the case of in vivo assays or therapeutic treatment, and under conditions in which assays are performed in the case of in vitro assays.

In the present invention the phrase "stringent hybridization conditions" or "stringent conditions" refers to conditions under which an oligomeric compound of the invention will hybridize to its target sequence, but to a minimal number of other sequences. Stringent conditions are sequence-dependent and will vary with different circumstances and in the context of this invention, "stringent conditions" under which oligomeric compounds hybridize to a target sequence are determined by the nature and composition of the oligomeric compounds and the assays in which they are being investigated.

"Complementary," as used herein, refers to the capacity for precise pairing of two nucleobases regardless of where the two are located. For example, if a nucleobase at a certain position of an oligomeric compound is capable of hydrogen bonding with a nucleobase at a certain position of a target nucleic acid, the target nucleic acid being a DNA, RNA, or oligonucleotide molecule, then the position of hydrogen bonding between the oligonucleotide and the target nucleic acid is considered to be a complementary position. The oligomeric compound and the further DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligonucleotide and a target nucleic acid.

It is understood in the art that the sequence of an antisense oligomeric compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure or hairpin structure). It is preferred that the antisense oligomeric compounds of the present invention comprise at least 70% sequence complementarity to a target region within the target nucleic acid, more preferably that they comprise 90% sequence complementarity and even more preferably comprise 95% sequence complementarity to the target region within the target nucleic acid sequence to which they are targeted. For example, an antisense oligomeric compound in which 18 of 20 nucleobases of the antisense oligomeric compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense oligomeric compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense oligomeric compound with a region of a target nucleic acid can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656).

Screening and Target Validation

In a further embodiment, "preferred target segments" may be employed in a screen for additional oligomeric compounds that modulate the expression of a selected protein. "Modulators" are those oligomeric compounds that decrease or increase the expression of a nucleic acid molecule encoding a protein and which comprise at least an 8-nucleobase portion which is complementary to a preferred target segment. The screening method comprises the steps of contacting a preferred target segment of a nucleic acid molecule encoding a protein with one or more candidate modulators, and selecting for one or more candidate modulators which decrease or increase the expression of a nucleic acid molecule encoding a protein. Once it is shown that the candidate modulator or modulators are capable of modulating (e.g. either decreasing or increasing) the expression of a nucleic acid molecule encoding a peptide, the modulator may then be employed in further investigative studies of the function of the peptide, or for use as a research, diagnostic, or therapeutic agent in accordance with the present invention.

The preferred target segments of the present invention may also be combined with their respective complementary antisense oligomeric compounds of the present invention to form stabilized double-stranded (duplexed) oligonucleotides. Such double stranded oligonucleotide moieties have been shown in the art to modulate target expression and regulate translation as well as RNA processing via an antisense mechanism. Moreover, the double-stranded moieties may be subject to chemical modifications (Fire et al., *Nature*, 1998, 391, 806-811; Timmons and Fire, *Nature* 1998, 395, 854; Timmons et al., *Gene*, 2001, 263, 103-112; Tabara et al., *Science*, 1998, 282, 430-431; Montgomery et al., *Proc. Natl. Acad. Sci. USA*, 1998, 95, 15502-15507; Tuschl et al., *Genes Dev.*, 1999, 13, 3191-3197; Elbashir et al., *Nature*, 2001, 411, 494-498; Elbashir et al., *Genes Dev.* 2001, 15, 188-200). For example, such double-stranded moieties have been shown to inhibit the target by the classical hybridization of antisense strand of the duplex to the target, thereby triggering enzymatic degradation of the target (Tijsterman et al., *Science*, 2002, 295, 694-697).

The compositions comprising oligomeric compounds of the present invention can also be applied in the areas of drug discovery and target validation. The present invention comprehends the use of the oligomeric compounds and preferred targets identified herein in drug discovery efforts to elucidate relationships that exist between proteins and a disease state, phenotype, or condition. These methods include detecting or modulating a target peptide comprising contacting a sample, tissue, cell, or organism with the oligomeric compounds of the present invention, measuring the nucleic acid or protein level of the target and/or a related phenotypic or chemical endpoint at some time after treatment, and optionally comparing the measured value to a non-treated sample or sample treated with a further oligomeric compound of the invention. These methods can also be performed in parallel or in combination with other experiments to determine the function of unknown genes for the process of target validation or to determine the validity of a particular gene product as a target for treatment or prevention of a particular disease, condition, or phenotype.

Effect of nucleoside modifications on RNAi activity is evaluated according to existing literature (Elbashir et al., Nature (2001), 411, 494-498; Nishikura et al., Cell (2001), 107, 415-416; and Bass et al., Cell (2000), 101, 235-238.)

Kits, Research Reagents, Diagnostics, and Therapeutics

The compositions of oligomeric compounds of the present invention can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics, the compositions of the present invention, either alone or in combination with other oligomeric compounds or therapeutics, can be used as tools in differential and/or combinatorial analyses to elucidate expression patterns of a portion or the entire complement of genes expressed within cells and tissues.

As one nonlimiting example, expression patterns within cells or tissues treated with one or more antisense oligomeric compounds are compared to control cells or tissues not treated with antisense oligomeric compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds and or oligomeric compounds that affect expression patterns.

Examples of methods of gene expression analysis known in the art include DNA arrays or microarrays (Brazma and Vilo, *FEBS Lett.,* 2000, 480, 17-24; Celis, et al., *FEBS Lett.,* 2000, 480, 2-16), SAGE (serial analysis of gene expression) (Madden, et al., *Drug Discov. Today,* 2000, 5, 415-425), READS (restriction enzyme amplification of digested cDNAs) (Prashar and Weissman, *Methods Enzymol.,* 1999, 303, 258-72), TOGA (total gene expression analysis) (Sutcliffe, et al., *Proc. Natl. Acad. Sci. U.S.A.,* 2000, 97, 1976-81), protein arrays and proteomics (Celis, et al., *FEBS Lett.,* 2000, 480, 2-16; Jungblut, et al., *Electrophoresis,* 1999, 20, 2100-10), expressed sequence tag (EST) sequencing (Celis, et al., *FEBS Lett.,* 2000, 480, 2-16; Larsson, et al., *J. Biotechnol.,* 2000, 80, 143-57), subtractive RNA fingerprinting (SuRF) (Fuchs, et al., *Anal. Biochem.,* 2000, 286, 91-98; Larson, et al., *Cytometry,* 2000, 41, 203-208), subtractive cloning, differential display (DD) (Jurecic and Belmont, *Curr. Opin. Microbiol.,* 2000, 3, 316-21), comparative genomic hybridization (Carulli, et al., *J. Cell Biochem. Suppl.,* 1998, 31, 286-96), FISH (fluorescent in situ hybridization) techniques (Going and Gusterson, *Eur. J. Cancer,* 1999, 35, 1895-904) and mass spectrometry methods (To, *Comb. Chem. High Throughput Screen,* 2000, 3, 235-41).

The compositions of the invention are useful for research and diagnostics in one sense because the oligomeric compounds of the compositions hybridize to nucleic acids encoding proteins. For example, oligonucleotides that are shown to hybridize with such efficiency and under such conditions as disclosed herein as to be effective protein inhibitors will also be effective primers or probes under conditions favoring gene amplification or detection, respectively. These primers and probes are useful in methods requiring the specific detection of nucleic acid molecules encoding proteins and in the amplification of the nucleic acid molecules for detection or for use in further studies. Hybridization of the antisense oligonucleotides, particularly the primers and probes, of the invention with a nucleic acid can be detected by means known in the art. Such means may include conjugation of an enzyme to the oligonucleotide, radiolabelling of the oligonucleotide or any other suitable detection means. Kits using such detection means for detecting the level of selected proteins in a sample may also be prepared.

The specificity and sensitivity of antisense methodologies is also harnessed by those of skill in the art for therapeutic uses. Antisense oligomeric compounds have been employed as therapeutic moieties in the treatment of disease states in animals, including humans. Antisense oligonucleotide drugs, including ribozymes, have been safely and effectively administered to humans and numerous clinical trials are presently underway. It is thus established that antisense oligomeric compounds can be useful therapeutic modalities that can be configured to be useful in treatment regimes for the treatment of cells, tissues and animals, especially humans.

For therapeutics, an animal, preferably a human, suspected of having a disease or disorder which can be treated by modulating the expression of a selected protein is treated by administering compositions of the invention in accordance with this invention. For example, in one non-limiting embodiment, the methods comprise the step of administering to the animal in need of treatment, a therapeutically effective amount of a protein inhibitor. The protein inhibitors of the present invention effectively inhibit the activity of the protein or inhibit the expression of the protein. In one embodiment, the activity or expression of a protein in an animal is inhibited by about 10%. Preferably, the activity or expression of a protein in an animal is inhibited by about 30%. More preferably, the activity or expression of a protein in an animal is inhibited by 50% or more.

For example, the reduction of the expression of a protein may be measured in serum, adipose tissue, liver or any other body fluid, tissue or organ of the animal. Preferably, the cells contained within the fluids, tissues or organs being analyzed contain a nucleic acid molecule encoding a protein and/or the protein itself.

The compositions of the invention can be utilized in pharmaceutical compositions by adding an effective amount to a suitable pharmaceutically acceptable diluent or carrier. Use of the compositions and methods of the invention may also be useful prophylactically.

Formulations

The compositions of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The compositions of the invention encompass any pharmaceutically acceptable salts, esters, or salts of such esters, or any other compound which, upon ad-ministration to an animal, including a human, is capable of providing (directly or indirectly) the biologically active metabolite or residue thereof. Accordingly, for example, the disclosure is also drawn to prodrugs and pharmaceutically acceptable salts of the compositions of the invention, pharmaceutically acceptable salts of such prodrugs, and other bioequivalents. The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the oligomeric compounds of the invention: i.e., salts that retain the desired biological activity of the parent compound and do mot impart undesired toxicological effects thereto. For oligonucleotides, preferred examples of pharmaceutically acceptable salts and their uses are further described in U.S. Pat. No. 6,287,860, which is incorporated herein in its entirety.

The present invention also includes pharmaceutical compositions and formulations which include the compositions of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

Emulsions are typically heterogenous systems of one liquid dispersed in another in the form of droplets usually exceeding 0.1 μm in diameter. Emulsions may contain additional components in addition to the dispersed phases, and the active drug which may be present as a solution in either the aqueous phase, oily phase or itself as a separate phase. Microemulsions are included as an embodiment of the present invention. Emulsions and their uses are well known in the art and are further described in U.S. Pat. No. 6,287,860, which is incorporated herein in its entirety.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes which are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860, which is incorporated herein is its entirety.

The pharmaceutical formulations and compositions of the present invention may also include surfactants. The use of surfactants in drug products, formulations and in emulsions is well known in the art. Surfactants and their uses are further described in U.S. Pat. No. 6,287,860, which is incorporated herein in its entirety.

In one embodiment, the present invention employs various penetration enhancers to effect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein in its entirety.

One of skill in the art will recognize that formulations are routinely designed according to their intended use, i.e. route of administration.

Preferred formulations for topical administration include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

For topical or other administration, oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters, pharmaceutically acceptable salts thereof, and their uses are further described in U.S. Pat. No. 6,287,860, which is incorporated herein in its entirety. Topical formulations are described in detail in U.S. patent application Ser. No. 09/315,298 filed on May 20, 1999, which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations axe those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/salts and fatty acids and their uses are further described in U.S. Pat. No. 6,287,860, which is incorporated herein in its entirety. Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally, in granular form including sprayed dried particles, or complexed to form micro or nanoparticles. Oligonucleotide complexing agents and their uses are further described in U.S. Pat. No. 6,287,860, which is incorporated herein in its entirety. Oral formulations for oligonucleotides and their preparation are described in detail in U.S. application Ser. Nos. 09/108,673 (filed Jul. 1, 1998), 09/315,298 (filed May 20, 1999) and 10/071,822, filed Feb. 8, 2002, each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Certain embodiments of the invention provide pharmaceutical compositions containing one or more of the compositions of the invention and one or more other chemotherapeutic agents which function by a non-antisense mechanism. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). When used with the compositions of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Combinations of compositions of the invention and other non-antisense drugs are also within the scope of this invention. One or more compositions of the invention can be used in combination with other therapeutic agents to create a cocktail as is currently the strategy for certain viral infections.

In another related embodiment, therapeutically effective combination therapies may comprise the use of two or more compositions of the invention wherein the multiple compositions are targeted to a single or multiple nucleic acid targets. Numerous examples of antisense oligomeric compounds are known in the art. Two or more combined compounds may be used together or sequentially Dosing The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Preparation of Human RNase H1

Human RNase H1 containing an N-terminal His-tag was expressed and purified as described in Lima, et. al., "Methods in Enzymology", Nicholson, A. W., Eds. 2001, pp 430-9, Academic Press, San Diego, Calif. Briefly, the plasmids were transfected into *E. coli* BL21 (DE3) (Novagen, WI). The bacteria was grown in Terrific Broth medium (Boi 101 Systems) at 37° C. and harvested at $OD_{600}$ of 1.2. The cells were induced with 1 mM isopropylthiogalactoside (IPTG) at 37° C. for 2 h. The cells were lysed in 6 M guanidine hydrochloride 100 mM sodium phosphate, 10 mM tris, pH 8.0 for 16-20 h at 24° C. The recombinant proteins were incubated for 1 h with 1 mL of Ni-NTA Super flow beads (Qiagen) per 50 mL of lysate. The Ni-NTA media was packed into an FPLC column and the RNase H1 proteins partially purified with sequential gradients (flow rate, 5 mL/min; buffer A, 100 mM sodium phosphate, 10 mM tris-HCl, 8 M Urea, pH 6.3; buffer B, 100 mM sodium phosphate, 10 mM tris-HCl, 2 M Urea, pH 6.3; buffer C, 100 mM sodium phosphate, 10 mM tris-HCl, 2 M Urea, 100 mM EDTA, pH 7.0). The eluent was further purified by ion exchange FPLC chromatography (Mono S Column; flow rate, 1 mL/min; buffer A, 20 mM sodium phosphate, 2 M urea, 200 mM NaCl, pH 7.0; buffer B, 20 mM sodium phosphate, 2 M urea, 2 M NaCl, pH 7.0). Fractions containing RNase H1 were pooled and concentrated. The concentrated protein was purified by RP-FPLC (Resourse RPC Column; flow rate 1 mL/min; Buffer A, 2% acetonitrile in $diH_2O$, 0.065% trifluoroacetic acid; buffer B 80% acetonitrile in $diH_2O$, 0.05% trifluoroacetic acid). Fractions were lyophilized, resuspended in $diH_2O$ and analyzed by SDS-PAGE.

Example 2

Synthesis of Oligonucleotides and Modified Oligonucleotides

The oligoribonucleotides were synthesized on a PE-ABI 380B synthesizer using 5'-O-silyl-2'-O-bis(2-acetoxyethoxy) methyl ribonucleoside phosphoramidites and procedures described by Scaringe, et. al., (*J. Am. Chem. Soc.*, 1998, 120, 11820-11821). The oligoribonucleotides were purified by reverse-phase HPLC or by precipitation 2 times out of 0.5 M NaCl with 2.5 volumes of ethyl alcohol.

The 1,4-anhydro-5-O-(4,4'-dimethoxytrityl)-2-deoxy-D-erythro-pentenol-3-[(2-cyanoethyl)-N,N-diisopropyl]phosphoramidite], 5'-O-(4,4'-dimethoxytrityl)]-3-(4-methylbenzoyl)-2-thio-thymidine-3'-[(2-cyanoethyl)-N)N-diisopropyl]phosphoramidite, 5'-O-(4,4'-dimethoxytrityl)-3'-deoxypseuodouridine-3'-[(2-cyanoethyl)-N,N-diisopropyl]phosphoramidite, 1',2'-dideoxy-1'-(2,4-difluorotoluoyl)-5'-O-(4,4'-dimethoxytrityl)-β-D-ribofuranose-3'-[(2-cyanoethyl)-N,N-diisopropyl] phosphoramidite and 5'-O-(4,4'-dimethoxytrityl)]-3-(4-methylbenzoyl)-2'-uridine-3'-[(2-cyanoethyl)-N,N-diisopropyl]phosphoramidite were procured from commercial sources (Glen Research Inc., Virginia, U.S. A). The 1-[2-deoxy-2-fluoro-5-O-(4,4'-dimethoxytrityl)]-3-[(2-cyanoethyl)-N,N-diisopropyl]phosphoramidite-β-D-[arabinofuranosyl]-thymine, 5'-O-(4,4'-dimethoxytrityl)]-2'-deoxy-2'-fluoro-thymidine-3'-[(2-cyanoethyl)-N,N-diisopropyl]phosphoramidite, 2-fluoro-6-methylbenzoimidazole deoxyribonucleotide, 4-methylbenzoimidazole deoxyribonucleotide, hydrocarbon linkers and 5'-O-(4,4'-dimethoxytrityl)]-2'-S-methyl-2'-thio-5-methyluridine-3'-[(2-cyanoethyl)-N,N-diisopropyl]phosphoramidite were synthesized as reported (Kawasaki, et. al., *J. Med. Chem.*, 1993, 36, 831-841, Yoneda, *Tetrahedron*, 1991, 47, 5329-5365 and Ikeda, et. al., *Nucleic Acids Res.* 1998, 26, 2237-2244). The nucleoside 3'-β-C-methylthymidine was synthesized from 1,2-O-isopropylidene-D-xylofuranose and converted to the 5'-O-(4,4'-dimethoxytrityl)-3'-O-(2-cyanoethyl-diisopropylamino)-phosphoramidite as previously described (Wilds, et. al., *Nucleic Acids Res.* 2000, 28, 3625-3635 and Fraser, et. al., *J. Heter. Chem.*, 1993, 30, 212-224). The 4'-α-C-methylthymidine nucleoside was synthesized in 12 steps starting from commercially available 1,2:5,6-Di-O-isopropylidene-α-D-glucofuranose purchased from Pfanstiehl, Waukegan, Ill. An alternate synthesis of this nucleoside has been reported by Sproat, et. al., *Oligonucleotide synthesis a practical approach*, Gait, M. J (ed.), IRL Press, Washington D.C., 1985, pp. 83-115 and Schmit, et. al., *Bioorg. Med. Chem. Let.* 1994, 4, 1969-1974. It was converted to 5'-O-(4,4'-dimethoxytrityl)-4'-α-C-methylthymidine-3'-O-(2-cyanoethyl)-N,N-Diisopropylphosphoramidite by following the procedure described for similar compounds by Waga, et. al., *Nucleosides & Nucleotides*, 1996, 15, 287-304 and Detmer et. al., *Eur. J. Org. Chem.* 2003, 1837-1846. Standard phosphoramidites and solid supports were used for incorporation of A, T, G, and C residues. A 0.1 M solution of each amidite in anhydrous acetonitrile was used for the synthesis of modified oligonucleotides. The oligonucleotides were synthesized on functionalized controlled pore glass (CPG) on an automated solid phase DNA synthesizer with the final DMT group retained at 5'-end. For incorporation of modified amidites, 6 equivalents of phosphoramidite solutions were delivered in two portions, each followed by a 3 min coupling wait time. All other steps in the protocol supplied by the manufacturer were used without modification. Oxidation of the internucleotide phosphite to the phosphate was carried out using 0.1 M solution of iodine in pyridine/water (20/1, v/v). with 10 min oxidation wait time. The coupling efficiencies were more than 97%. To deprotect oligonucleotides containing 2'-deoxy-2'-fluoro-thymidine and 2'-deoxy-2'-fluoro-arabinofuranosylthymine, the solid support bearing the oligonucleotides were suspended in aqueous ammonia (28-30 wt %):ethanol (3:1, 3 mL for 2 μmol scale synthesis) and heated at 55° C. for 6 h. All other modified oligonucleotides after completion of the synthesis, the solid supports bearing the oligonucleotides were suspended in aqueous ammonium hydroxide (28-30 wt %, 2 mL for 2 μmol scale synthesis) and kept at room temperature for 2 h. The solid support was filtered and the filtrate was heated at 55° C. for 6 h to complete the removal of all protecting groups. Crude oligonucleotides were purified by high performance liquid chromatography (HPLC, C-4 column, Waters, 7.8×300 mm, A=100 mM ammonium acetate, pH 6.5-7, B=acetonitrile, 5-60% of B in 55 min, flow 2.5 mL min$^{-1}$, λ 260 nm). Detritylation was achieved by adjusting the pH of the solution to 3.8 with acetic acid and keeping at room temperature until complete removal of the trityl group, as monitored by HPLC analysis. The oligonucleotides were then desalted by HPLC to yield modified oligonucleotides in 30-40% isolated yield calculated based on the loading of the 3'-base to solid support (Kanazaki, et. al., *J. Amer. Chem. Soc.* 2000, 122, 2422-2432). The oligonucleotides were characterized by electrospray mass spectroscopy (ES-MS) and their purity was assessed by HPLC and capillary gel electrophoresis (CGE). The purity of the oligonucleotides was >90%.

Oligonucleotides with abasic sites were conveniently generated by the use of uracil-DNA glycosylase (see Duncan, et. al., *Gene*, 1984, 28, 211-219). Oligonucleotides containing deoxyuridine residue were synthesized as described (vide supra). The HPLC purified oligonucleotides (0.32 mg) were dissolved in Uracil-DNA Glycosylase (149 μl, I unit in 1 μl dissolved in 30 mM HEPES-KOH (pH 7.5), 150 mM NaCl, 1 mM EDTA, 1 mM DTT, 0.05% Tween 20 and 50% glycerol) and incubated at 37° C. for 4 h. The reaction was terminated by filtering the enzyme using low binding membrane filter (0.22 μm, Millipore Inc., Bedford, Mass., USA). The release of uracil was observed in HPLC analysis of the reaction mixture (Waters C-4 3.9×300 mm, delta pack, 15 micron, 300 A°, A=100 mM ammonium acetate, B=acetonitrile 0 to 25% B in 55 min, flow 1.5 ml min$^{-1}$, λ 260 nm) and co injecting the authentic sample. The oligonucleotides were purified by HPLC (conditions same above). The purity (>90%) of the oligonucleotides was assessed by HPLC analysis.

Example 3

Preparation of $^{32}$P Labeled Substrate

The RNA substrate was 5'-end-labeled with $^{32}$P using 20 U of T$_4$ polynucleotide kinase (Promega, WI), 120 pmol (7000 Ci/mmol) [γ-$^{32}$P]ATP (ICN, CA), 40 pmol RNA, 70 mM tris, pH 7.6, 10 mM MgCl$_2$ and 50 mM DTT. The kinase reaction was incubated at 37° C. for 30 min. The labeled oligoribonucleotide was purified by electrophoresis on a 12% denaturing polyacrylamide gel (40). The specific activity of the labeled oligonucleotide is approximately 3000 to 8000 cpm/fmol.

Example 4

Preparation of the Heteroduplex

The heteroduplex substrate was prepared in 100 μL containing unlabeled oligoribonucleotide ranging from 100 to 1000 nM, 10$^5$ cpm of $^{32}$P labeled oligoribonucleotide, two-fold excess complementary oligodeoxyribonucleotide and hybridization buffer [20 mM tris, pH 7.5, 20 mM KCl]. Reactions were heated at 90° C. for 5 min, cooled to 37° C. and 60 U of Prime RNase Inhibitor (5 Prime ~3 Prime, CO) and MgCl$_2$ at a final concentration of 1 mM were added. Hybridization reactions were incubated 2-16 h at 37° C. and 1 mM tris(2-carboxyethyl)phosphate (TCEP) was added.

Example 5

Multiple-Turnover Kinetics

The human RNase H1 proteins were incubated with dilution buffer (50 mM tris, 50 mM NaCl, 100 µM TCEP, pH 7.5) for 1 h at 24° C. The heteroduplex substrate was digested with 0.4 ng of enzyme at 37° C. A 10 µl aliquot of the cleavage reaction was removed at time points ranging from 2-120 min and quenched by adding 5 µL of stop solution (8 M urea and 120 mM EDTA). The aliquots were heated at 90° C. for 2 min, resolved in a 12% denaturing polyacrylamide gel and the substrate and product bands were quantitated on a Molecular Dynamics PhosphorImager. The concentration of the converted product was plotted as a function of time. The initial cleavage rate ($V_0$) was obtained from the slope (mole RNA cleaved/min) of the best-fit line for the linear portion of the plot, which comprises, in general <10% of the total reaction and data from at least five time points. Site-specific cleavage rates were determined by plotting the concentration of the converted product for a given cleavage site as a function of time.

Oligodeoxyribonucleotides of sequence CTACGCTTTCCACGCACAGT (SEQ ID #1) were prepared with nucleotide modifications positioned within the region preferentially cleaved by human RNase H1, as indicated below, where (x) shows the position of the modification for the respective oligodeoxyribonucleotide (positions are numbered 5'→3' on the oligodeoxyribonucleotide.)

| | | |
|---|---|---|
| T7: | CTACGCxTTCCACGCACAGT | (SEQ ID NO: 1) |
| T8: | CTACGCTxTCCACGCACAGT | (SEQ ID NO: 1) |
| T9: | CTACGCTTxCCACGCACAGT | (SEQ ID NO: 1) |
| C10: | CTACGCTTTxCACGCACAGT | (SEQ ID NO: 1) |
| C11: | CTACGCTTTCxACGCACAGT | (SEQ ID NO: 1) |
| A12: | CTACGCTTTCCxCGCACAGT | (SEQ ID NO: 1) |
| C13: | CTACGCTTTCCAxGCACAGT | (SEQ ID NO: 1) |
| G14: | CTACGCTTTCCACxCACAGT | (SEQ ID NO: 1) |
| C15: | CTACGCTTTCCACGxACAGT | (SEQ ID NO: 1) |

Modified nucleotides containing conformationally biased sugar puckers, included northern biased modifications: 2-thiouridine ($S^2T$) and 2'-fluorothymidine (2'-F); southern biased modifications: 2'-methylthiothymidine (2'-S-methyl), 4'-methylthymidine (4'-methyl), 3'-methylthymidine (3'-methyl), and pseudouridine (pseudo-U); and eastern biased sugar modification: 2'-ara-fluoropyrimidine (2'-ara-Fluoro).

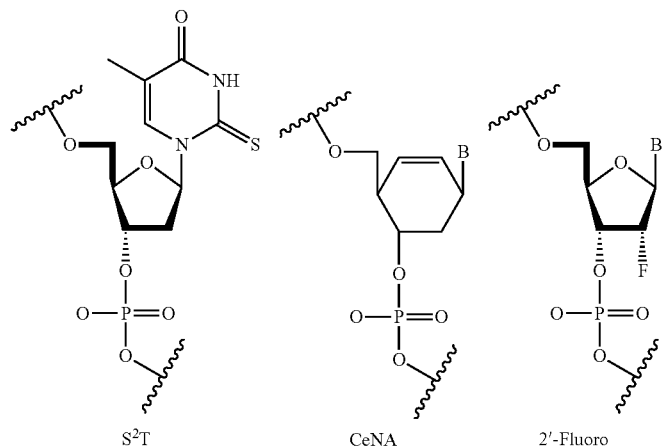

Northern or C3-endo sugar conformation $S^2T$    CeNA    2'-Fluoro

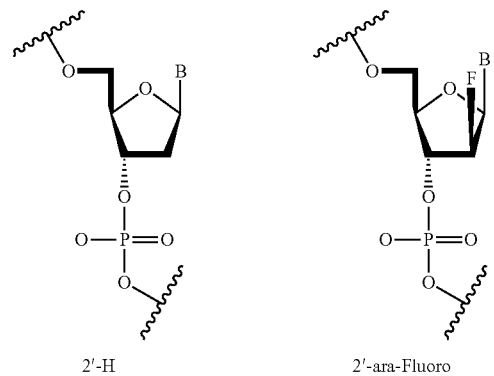

Eastern or O4-endo sugar conformation

2'-H    2'-ara-Fluoro

Southern or
C2-endo sugar conformation

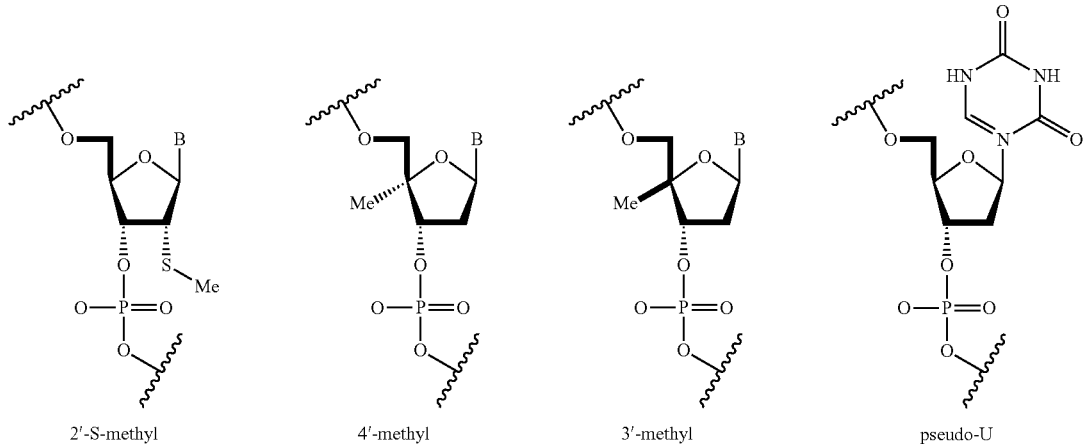

2′-S-methyl     4′-methyl     3′-methyl     pseudo-U

Structures of the modifications designed to introduce conformational flexibility (transition moietys) into the heteroduplex include: the propyl (C3'), butyl ($C_4$) and pentyl ($C_5$) hydrocarbon linkers; tetrahydrofuran (THF), abasic and ganciclovir ($G_v$) modifications; and the π-stacking 2-fluoro-6-methylbenzoimidazole (2-F-6-Me-ben), 4-methylbenzoimidazole (4-Me-ben) and 2,4-difluorotoluoyl (2,4-F-tolyl) deoxyribonucleotides, as illustrated below:

-continued

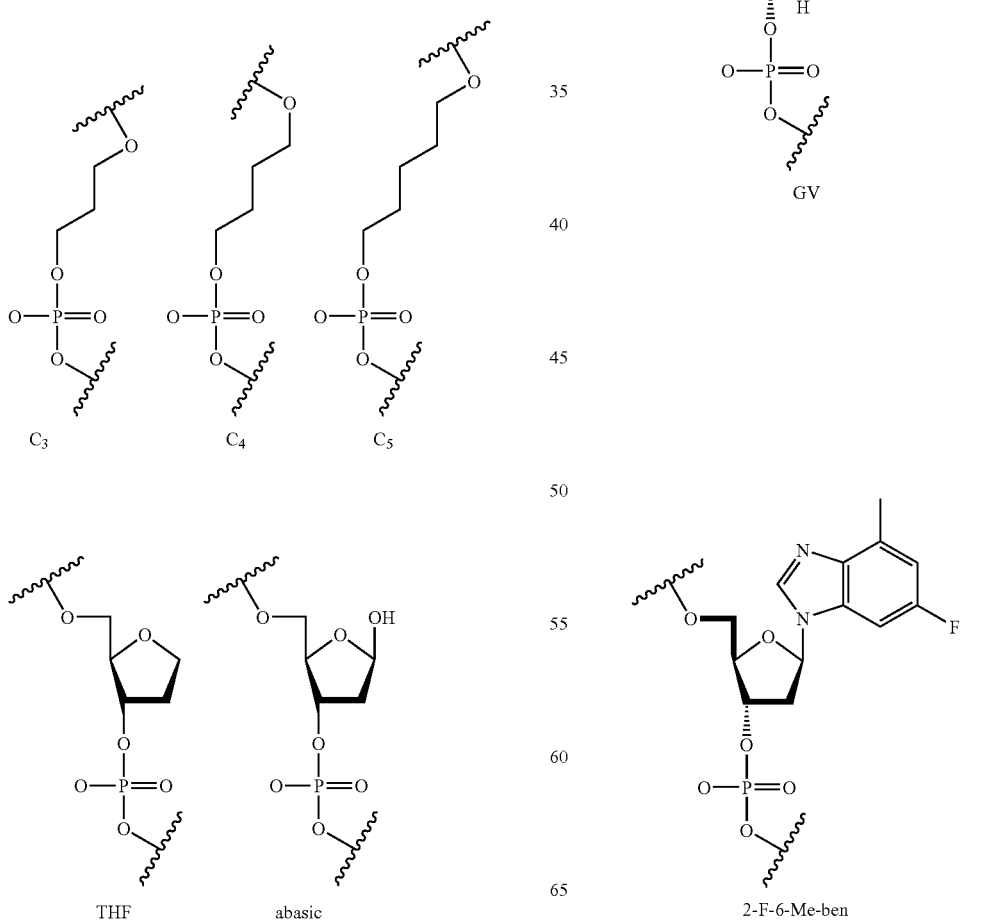

$C_3$     $C_4$     $C_5$

GV

THF     abasic     2-F-6-Me-ben

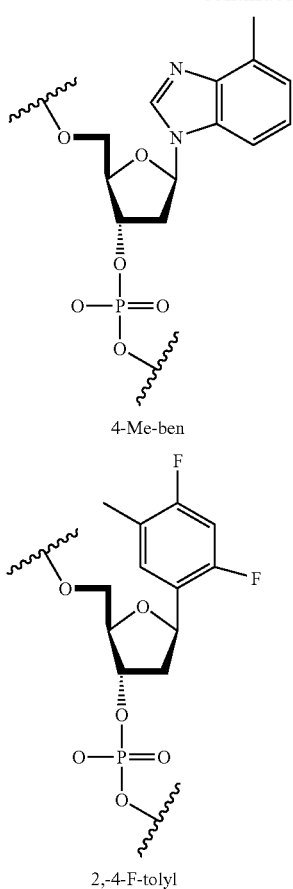

4-Me-ben

2,-4-F-tolyl

The modified oligodeoxyribonucleotides were annealed to complementary RNA and the heteroduplexes digested with human RNase H1 under multiple-turnover conditions as described above. Initial cleavage rates ($V_0$) as well as site-specific cleavage rates, i.e. initial cleavage rates for each human RNase H1 cleavage site, were determined (see Table XI).

TABLE XI

Relative initial cleavage rates and site-specific for modified heteroduplex substrates.

| Modification | Position of Modification | Ratio Site-Specific Cleavage Rate[1] (modified/unmodified) | | | | | Ratio $V_0$[2] (modified/ unmodified) |
|---|---|---|---|---|---|---|---|
| | | −2 | −1 | 0 | +1 | +2 | |
| 2'-ara-Fluoro | $T_7$ | 0.9 | 1.1 | 0.9 | 1.0 | — | 1.1 |
| | $T_8$ | 1.3 | 1.5 | 0.8 | 1.5 | 1.5 | 1.1 |
| | $T_9$ | 1.0 | 1.1 | 1.5 | 0.6 | 0.4 | 1.1 |
| | $C_{10}$ | 0.7 | 1.1 | 0.8 | 1.0 | 0.6 | 1.2 |
| | $C_{13}$ | 1.1 | 0.7 | 0.6 | 0.8 | 0.6 | 1.1 |
| | $C_{15}$ | — | — | 1.1 | 1.3 | 0.4 | 1.1 |
| Pseudo-U | $T_7$ | 0.8 | 0.7 | 0.6 | 0.6 | — | 0.9 |
| | $T_8$ | 1.4 | 1.3 | 0.7 | 0.2 | 0.3 | 1.1 |
| | $T_9$ | 1.0 | 0.8 | 1.0 | 0.2 | 0.2 | 1.2 |
| 2'-Fluoro | $T_7$ | 0.5 | 0.2 | 0.2 | 0.1 | — | 0.6 |
| | $T_8$ | 0.8 | 0.6 | 0.2 | 0.3 | 0.6 | 0.7 |
| | $T_9$ | 1.1 | 0.9 | 0.2 | 0.3 | 0.6 | 0.7 |
| $S^2U$ | $T_7$ | 0.4 | 0.4 | 0.2 | 0.1 | — | 0.5 |
| | $T_8$ | 1.1 | 0.6 | 0.0 | 0.0 | 0.7 | 0.7 |
| | $T_9$ | 1.3 | 1.0 | 0.3 | 0.3 | 0.9 | 0.7 |

TABLE XI-continued

Relative initial cleavage rates and site-specific for modified heteroduplex substrates.

| Modification | Position of Modification | Ratio Site-Specific Cleavage Rate[1] (modified/unmodified) | | | | | Ratio $V_0$[2] (modified/ unmodified) |
|---|---|---|---|---|---|---|---|
| | | −2 | −1 | 0 | +1 | +2 | |
| 2'-S-Methyl | $T_7$ | 0.6 | 0.6 | 0.1 | 0 | — | 0.5 |
| | $T_8$ | 0.5 | 0.6 | 0.1 | 0 | 0 | 0.4 |
| | $T_9$ | 0.7 | 0.6 | 0.2 | 0.1 | 0.3 | 0.4 |
| 4'-Methyl | $T_7$ | 0.5 | 0.3 | 0 | 0 | — | 0.5 |
| | $T_8$ | 0.3 | 0.1 | 0 | 0 | 0 | 0.6 |
| | $T_9$ | 0 | 0 | 0 | 0 | 0 | 0.3 |
| 3'-Methyl | $T_7$ | 0.3 | 0.7 | 1.0 | 0.8 | — | 0.8 |
| | $T_8$ | 1.6 | 0.8 | 0.7 | 0.1 | 0.1 | 0.8 |
| | $T_9$ | 1.3 | 0.7 | 0.6 | 0.2 | 0 | 0.7 |
| Propyl linker | $A_{12}$ | 0.6 | 0 | 0 | 0 | 0 | 0.5 |
| | $G_{14}$ | — | 0 | 0 | 0 | 0 | 0.6 |
| | $C_{15}$ | — | — | 0 | 0 | 0 | 0.5 |
| Butyl linker | $A_{12}$ | 0.5 | 0.1 | 0 | 0 | 0 | 0.5 |
| | $C_{15}$ | — | — | 0.1 | 0 | 0.6 | 0.5 |
| Pentyl linker | $A_{12}$ | 0.1 | 0.1 | 0 | 0.5 | 0.9 | 0.6 |
| | $C_{15}$ | — | — | 0.1 | 0 | 0.9 | 0.5 |
| Tetrahydrofuran | $A_{12}$ | 0 | 0 | 0 | 0.6 | 0.5 | 0.4 |
| | $G_{14}$ | — | 0.5 | 0 | 0.1 | 0 | 0.4 |
| Abasic | $T_9$ | 0.6 | 0.3 | 0.2 | 0.3 | 0.2 | 0.6 |
| | $C_{10}$ | 0.5 | 0.4 | 0.5 | 0.3 | 0.1 | 0.6 |
| | $C_{11}$ | 0.6 | 0.3 | 0.2 | 0.3 | 0.2 | 0.5 |
| Gancyclovir | $G_{14}$ | — | 0.1 | 0.5 | 0.3 | 0.4 | 0.4 |
| 4-F-6-Me-ben | $G_{14}$ | — | 0.8 | 0.8 | 0.9 | 0.9 | 0.8 |
| 4-Me-ben | $A_{12}$ | 0.7 | 0.7 | 0.9 | 0.9 | 0.5 | 0.8 |
| 2,4-F-tolyl | $T_9$ | 0.9 | 1.0 | 1.3 | 0.8 | 0.2 | 0.8 |
| | $C_{10}$ | 1.3 | 1.5 | 1.0 | 1.0 | 0.1 | 0.9 |
| | $C_{11}$ | 1.3 | 1.1 | 0.8 | 0.7 | 0.5 | 1.1 |

[1]Ratio site-specific cleavage rates represents the initial cleavage rates for the modified heteroduplexes divided by the unmodified substrate.
[2]Ratio $V_0$ represents the initial cleavage rates for the modified heteroduplexes divided by the unmodified substrate.
— Dashed lines indicate positions not cleaved by human RNase H1 for the unmodified substrate and modified heteroduplexes.
The $V_0$ values are an average of three measurements with estimated errors of CV < 10%.

The initial cleavage rates ($V_0$) observed for the modified heteroduplexes were predominantly dependant on the class of modification tested rather the position of the specific modification within the oligodeoxynucleotide (Table XI). For example, several modified heteroduplexes (e.g., 4'-methylthymidine, tetrahydrofuran, gancyclovir and the hydrocarbon linkers) exhibited initial cleavage rates 2 to 3-fold slower than the $V_0$ of the unmodified substrate whereas the 2'-ara-fluoropyrimidine, pseudouridine and π-stacking deoxyribonucleotides, (e.g., 2-fluoro-6-methylbenzoimidazole, 4-methylbenzoimidazole and 2,4-difluorotoluoyl deoxyribonucleotides) modified heteroduplexes exhibited initial cleavage rates comparable to the rate observed for the unmodified substrate (Table XI). It is important to note that a 2-fold reduction of the initial cleavage rate due to a single nucleotide modification is significant considering that human RNase H1 cleaves the substrate at multiple positions within the heteroduplex. In contrast, the initial cleavage rates for the heteroduplexes containing the same modification at different positions within the substrate showed only a ±10 percent difference in the cleavage rates (Table XI). Nor did the effects vary as a function of the specific nucleotide modified. For example, the cleavage rates at the ribonucleotide opposing an abasic site was 0.2, 0.5 and 0.2 of the control at, respectively, positions 9, 10 and 11. The relative cleavage rates at positions 9 and 11 were comparable even though positions 9 and 11 in the natural substrates were thymidine and cytosine. Moreover, the effects on the cleavage at adjacent sites were comparable. Similar results were observed for other modifications that produced dramatic reductions in the cleavage rates, (e.g., 2'-fluoro) and modifications that had little to no effect on the cleavage rates, (2'-ara-fluoro).

The modifications that exhibited the greatest impact on the site-specific cleavage rate for the ribonucleotide opposing the modification also exhibited the broadest effect on the site-specific cleavage rates surrounding ribonucleotides. The tetrahydrofuran, hydrocarbon linkers, 4'-methylthymidine and abasic deoxyribonucleotide modifications which significantly reduced or ablated the site-specific cleavage rates for the ribonucleotide opposing the modification also showed significantly slower site-specific cleavage rates for the surrounding 3' and 5'-ribonucleotides, (e.g., positions −2 to +2) compared with the unmodified substrate (Table XI). Interestingly, with the exception of 4'-methylthymidine, these modifications were predicted to impart the greatest degree of conformational flexibility at the site of the modification. The heteroduplexes containing the pseudouridine, 2'-ara-fluoropyrimidine, 3'-methylthymidine and Π-stacking deoxyribonucleotides modifications which exhibited little to no reduction in the site-specific cleavage rate for the ribonucleotide opposing the modification also showed only a modest reduction in the site-specific rates for the surrounding ribonucleotides (Table XI). For a majority of the modified deoxyribonucleotides tested, the influence on the human RNase H1 activity of the adjacent ribonucleotides appeared to be unidirectional. For example, the 2'-methylthiothymidine, 3'-methylthymidine, 2-thiouridine, 2'-fluorothymidine and pseudouridine reduced the site-specific cleavage rates for the adjacent 3'-ribonucleotides more significantly than the 5'-ribonucleotides.

Although there was generally quite a good correlation between the effects on the cleavage rate at the ribonucleotide opposing the modification and the overall cleavage rate, there were interesting exceptions. Consider 2'-thiothymidine, this modification at position 8 ablated the cleavage at the opposing site and reduced the relative overall rate to 0.7, while the same modification at position 7 reduced the relative site-specific rate to 0.2 of control and the overall relative rate to 0.5. These results can be explained different effects on the site-specific cleavage rates of adjacent ribonucleotides. In contrast, the effects of the 4'-methylthymidine modifications on the overall rates were less significant than on the site-specific rates for the opposing and surrounding ribonucleotides and this is due to the fact that the ablated cleavage sites account for approximately half of the total site-specific cleavage rates.

Within the context of nucleic acid duplexes, the degree of pseudorotation of the sugar between the southern to the northern conformation sets into motion a series of structural changes that ultimately result in the formation of B-form or A-form duplexes (see Saenger, W. (1984) *Principles of Nucleic Acid Structure*, Springer-Verlag, New York). The shift in helical conformation resulting from the pseudorotation of the sugar starts with the change in the torsion angles of the glycosyl and C4-C5 bonds. The spatial orientation of the glycosyl bond in turn dictates the distance between the internucleotide phosphates, the rotation and axial rise per nucleotide, the tilt of the base-pair and the dislocation of the base pairs from the helical axis.

These factors combined, control the depth and width of the major and minor grooves. RNA/DNA heteroduplexes are unique in that these duplexes exhibit an intermediate structure between the canonical A-form and B-form helical geometry. At approximately 9 Å the minor groove width for the heteroduplex is approximately midway between the minor groove widths for A-form (~11 Å) and B-form (~6 Å) duplexes (see Fedoroff, et. al., *J. Mol. Biol.* 1993, 233, 509-523 and Egli, et. al., *Biochemistry* 1996, 35, 8489-8494). The RNA sugars of the heteroduplex exhibit a northern sugar conformation whereas the DNA sugars form an eastern $O_4$,-endo sugar conformation. The intrastrand phosphate distances for the heteroduplex also differ from canonical A-form and B-form duplexes in that the DNA strand maintains an intrastrand phosphate distance consistent with B-form duplexes whereas the intrastrand phosphate distance within the RNA strand is closer to an A-form duplex. Finally, the unique minor groove width as well as the position of the inter- and intrastrand phosphates exhibited by the DNA/RNA heteroduplexes suggest that these features may be the key recognition determinants for RNase H enzymes.

Although, the key catalytic amino acids of human RNase H1 have been identified, the structural and physical properties of the enzyme and substrate responsible for the selective recognition and cleavage of the RNA in the RNA/DNA heteroduplex are not known as a co-crystal structure of the enzyme/substrate complex has not been solved. Site-directed mutagenesis of the *E. coli* and human RNase H1 enzymes combined with molecular modeling of the enzyme/substrate complex suggest that the enzyme binds to the minor groove of the heteroduplex substrate (Wu, et. al., *J. Biol. Chem.* 2001, 276, 23547-23553). In addition, the catalytic site of the enzyme was predicted to contact the 2'-hydroxyls of the RNA strand and the phosphates of the DNA strand surrounding the scissile phosphate.

In this study, a complementary mutational analysis on the structure of the substrate at the catalytic site for human RNase H1 was performed. A series of modified heteroduplexes with the modifications positioned within the catalytic site of the substrate were designed The modifications consisted of nucleotides exhibiting northern, southern and eastern sugar conformations, base modifications which π-stack with adjacent nucleotides but do not form hydrogen bonds, abasic deoxynucleotides, internucleotide hydrocarbon linkers ranging 3-5 residues and ganciclovir substitution of the deoxyribose to determine the role of helical geometry, sugar conformation, bulk in the minor groove and conformational flexibility within the heteroduplex on human RNase H1 activity.

The Role of Sugar Conformation within the Catalytic Site of the Heteroduplex

The northern biased deoxyribonucleotides selected for this study included the 2'-fluorothymidine and 2-thiouridine modifications, which lack bulky 2'-substituents in order to avoid possible steric interactions with the enzyme. These modifications were determined to influence sugar conformation through distinctly different mechanisms. For example, the highly electronegative fluorine of the 2'-fluorothymidine acts in conjunction with the gauche effect to strongly stabilize the sugar in the northern pucker (Kawasaki, et. al., *J. Med. Chem.*, 1993, 36, 831-841). In the case of 2-thiouridine, it has been shown at the dinucleotide level that the highly polarizable sulfur stabilizes the $C_3$,-endo sugar conformation as well as the stacking interactions with the neighboring nucleotides and imparts stronger hydrogen bonding due to the increased acidity of the N-3 imino proton. The heteroduplexes containing the northern biased modifications showed significantly slower site-specific cleavage rates for the ribonucleotide opposing the modification (position 0). Further, these modified heteroduplexes also exhibited significantly slower site-specific cleavage rates for the adjacent 3'-ribonucleotide, i.e., position +1, while little to no reduction for the site-specific cleavage rates was observed for the adjacent 5'-ribonucleotide, i.e., position −1, thus these modifications appear to be influencing the structure of the adjacent base-pairs in a unidirectional manner.

The Role of the Minor Groove Substituents

In contrast to northern biased deoxyribonucleotides, modified deoxyribonucleotides exhibiting a southern biased sugar pucker more closely mimic the sugar conformation of native deoxyribonucleotides. The effects of southern biased deoxyribonucleotide modifications on RNase H1 activity have not been previously investigated. Heteroduplexes containing the 2'-methylthiothymidine modification were poor substrates for human RNase H1 exhibiting significantly slower initial cleavage rates ($V_0$) and site-specific cleavage rates for both the opposing and adjacent ribonucleotides. The 2'-methylthiothymidine nucleoside is highly southern biased as a result of the electronegativity and steric bulk of the 2'-substituent. The 2'-methylthio substituent potentially poses a similar steric problem for the enzyme as the 2'-alkoxy moieties and may account for the observed loss in human RNase H1 activity. In contrast, the pseudouridine modification had little to no effect on cleavage rates. These data suggest that, consistent with the predicted binding model, human RNase H1 is likely interacting with the minor groove of the heteroduplex substrate and that a low energy barrier for interconversion of the sugar conformation is preferred.

The Role of the Deoxyribonucleotide Phosphate Groups

Heteroduplexes containing the 4'-methylthymidine modifications were less effective substrates for human RNase H1 exhibiting initial cleavage rates 2 to 3-fold slower than the unmodified heteroduplex. The 4'-methylthymidine inhibited the human RNase H1 cleavage of the ribonucleotide opposing the modification and the adjacent 3'-ribonucleotides. The site-specific rates for the adjacent 5'-ribonucleotides were significantly reduced compared to the unmodified substrate. In contrast, the heteroduplexes containing the 3'-methyl modified deoxyribonucleotide, which have been shown to exhibit a sugar conformation similar to the 4'-methyl nucleosides, were significantly better substrates for human RNase H1. The observed differences in the human RNase H1 activity for the 4'-methylthymidine and 3'-methylthymidine heteroduplexes may be a function of the position of the 4'-methyl moiety on the furansose ring, which is predicted to contribute bulk in the minor groove potentially interfering with enzyme binding (Detmer, et. al., *Eur. J. Org. Chem.* 2003, 1837-1846). Furthermore, the loss in human RNase H1 activity observed for the 4'-methylthymidine heteroduplexes suggests that proper orientation of the phosphate group on the deoxyribonucleotide opposing the scissile ribonucleotide is important for human RNase H1 activity.

Optimal Modification Mimic the Conformation of Deoxyribonucleotides

The nucleotide modifications predicted to mimic the sugar pucker of the deoxyribonucleotide of an RNA/DNA heteroduplex, (e.g., heteroduplexes containing the 2'-ara-fluoropyrimidines and pseudouridine modifications) exhibited cleavage rates comparable to the rates observed for the unmodified substrate. The 2'-ara-fluoro modification has been shown by NMR to form the eastern $O_{4'}$-endo sugar conformation similar to DNA when hybridized to RNA (Denissov, et. al., *Nucleic Acids Res.* 2001, 29, 4284-4293). In addition, the size and position of the 2'-ara-substituent, i.e., the fluorine is directed upward and away from the minor groove, is predicted not to sterically interfere with the enzyme. In the case of the pseudouridine, the NMR structure indicated a modestly higher southern sugar pucker population for the nucleoside due to the influence of the torsion angle of the C—C glycosyl bond and the $C_{1'}$ and $C_{2'}$ bond (Parikh, et. al., *Proc. Natl. Acad. Sci.* 2000, 10, 5083-5088.) Furthermore, the CD spectrum for RNA/pseudouridine and DNA/pseudouridine duplexes showed, respectively, an RNA-like $C_{3'}$-endo and DNA-like $C_{2'}$-endo sugar pucker for the pseudouridine deoxyribonucleotides suggesting that pseudouridine exhibits a conformational flexibility comparable to DNA (See Trapane, et. al., *J. Am. Chem. Soc.* 1994, 116, 8412-8413 and Hall and McLaughlin, *Biochemistry* 1991, 30, 1795-1801.) Apparently, both the eastern sugar pucker and conformational flexibility of the deoxyribonucleotide furanose ring are favored by the enzyme, i.e., locking the sugar north or south resulted in slower cleavage rates.

Role of Conformational Flexibility within the Catalytic Site of the Heteroduplex Conformational flexibility was introduced at the catalytic site of the heteroduplex substrate with modifications exhibiting incrementally increasing flexibility with the hydrocarbon linkers predicted to exhibit the greatest degree of conformational flexibility followed by abasic and ganciclovir deoxyribonucleotides and the π-stacking deoxyribonucleotides, (e.g., 2-fluoro-6-methylbenzoimidazole, 4-methylbenzoimidazole and 2,4-difluorotoluoyl deoxyribonucleotides). Table XI shows that with increased conformational flexibility at the catalytic site, the initial cleavage rates ($V_0$) and site-specific cleavage rates decreased. For example, the hydrocarbon linkers were predicted to exhibit the greatest degree of conformational flexibility and were among the poorest substrates for RNase H1 activity. The site-specific rates for the ribonucleotide opposing these modification and the surrounding 3' and 5'-ribonucleotides were either significantly reduced or ablated resulting in initial cleavage rates ($V_0$) approximately two-fold slower than the unmodified substrate. The broad effect on the site-specific rates for the ribonucleotides surrounding the opposing ribonucleotide is likely due to the fact that the conformationally flexible linkers bridge both the 3' and 5'-deoxyribonucleotides. Interestingly, similar effects on the cleavage rates were observed for all three hydrocarbon linkers even through the linkers ranged in length from three to five carbons with the propyl and pentyl linkers predicted to be, respectively, shorter and longer than the length of the native deoxyribonucleotide linkage and the butyl linker predicted to most closely approximate the intraphosphate distance of the deoxyribonucleotide. The ganciclovir, abasic and tetrahydrofuran modified deoxyribonucleotides were also poor substrates for human RNase H1, although the site-specific cleavage rates for these heteroduplexes were slightly faster than the rates observed for the heteroduplexes containing the hydrocarbon linkers. Taken together these data suggest that a conformationally rigid phosphate backbone is required for human RNase H1 activity. Furthermore, the slight improvement in the cleavage rates observed for the ganciclovir and abasic modifications compared with the hydrocarbon linkers suggests that the furanose ring of the abasic deoxyribonucleotide and hydrogen bond base-pair formation of the ganciclovir modification likely offer modest conformational rigidity to the substrate.

In contrast, the π-stacking deoxyribonucleotides, 2-fluoro-6-methylbenzoimidazole, 4-methylbenzoimidazole and 2,4-difluorotoluoyl deoxyribonucleotides better supported human RNase H1 activity. Comparable initial cleavage rates and site-specific cleavage rates were observed for these heteroduplexes compared to the unmodified substrate. Interestingly, the site-specific cleavage rates for the second 3'-ribonucleotide were significantly slower suggesting that a stable hydrogen bond base-pair is required two base-pairs 5' to the scissile phosphate. The fact that the π-stacking deoxyribonucleotides exhibited comparable site-specific cleavage rates for the ribonucleotide opposing the modification compared to the unmodified substrate suggests that these modifications likely form favorable stacking interactions resulting in a stable helical conformation. In fact, previous studies have shown that the 2-fluoro-6-methylbenzoimidazole deoxyribonucleotide was an effective substitute of native deoxyribonucleotides and this modification was shown to act as an efficient template for replicating DNA with KF(exo)-polymerase (Moran, et. al., *J. Am. Chem. Soc.* 1997, 119, 2056-2057).

Interactions Between Enzyme and Substrate at the Catalytic Site

The interactions between RNase H1 and the heteroduplex substrate at the catalytic site has been inferred by molecular modeling and site-directed mutagenesis of *E. coli* and human RNase H1 as well as the crystal structure of the *E. coli* enzyme (Iwai, et. al., *FEBS Letters* 1995, 368, 315-320). Specifically, site-directed mutagenesis suggests that the glutamine at position 72 of the *E. coli* enzyme forms a hydrogen bond with the 2'-hydroxyl of the ribonucleotide at position −1 and that the backbone imino and carbonyl groups of cysteine-13 function as proton donor and acceptor, respectively, in the hydrogen bonding interaction with the 2'-hydroxyl of the ribonucleotide at position +1. The asparagine-16 and asparagine-44 residues of the enzyme were suggested to bind electrostatically with the phosphates of, respectively, the deoxyribonucleotides opposing the scissile ribonucleotide and the ribonucleotide at position −1. The aspartic acid residues at positions 10 and 70 were predicted to bind the 2'-hydroxyl of the scissile ribonucleotide via $Mg^{2+}$ ion coordination. Finally, these amino acid residues are conserved in human RNase H1 and have been shown by site-directed mutagenesis to be required for activity. The loss of human RNase H1 activity observed for the heteroduplexes containing southern biased 2'-methylthiothymidine modification as well as the lack of cleavage observed for the northern biased 2'-alkoxy modified heteroduplexes is consistent with the predicted binding site for the enzyme (see Lima and Crooke, *Biochemistry* 1997, 36, 390-398, Wu, et. al., *J. Biol. Chem.* 1999, 274, 28270-28278 and Katayangi, et. al., *Proteins: Sruct., Funct., Genet.* 1993, 17, 337-346). Together, these data suggest that, irrespective of sugar conformation, bulky 2'-substituents positioned in the minor groove of the heteroduplex substrate interfere with human RNase H1 cleavage. Similarly, the 2-thio substitution of 2-thiouridine is predicted to be situated within the minor groove of the heteroduplex and the slower cleavage rates observed for these heteroduplexes may be the result of the sulfur either interfering with the enzyme sterically or as a result of it's strong electronegative properties.

The modified heteroduplexes examined here suggest that the width of the minor groove of the heteroduplex substrate is important for RNase H1 catalysis and that variations in minor groove width as a function of sugar pucker appear to obviate the proper positioning of the enzyme on the heteroduplex substrate. For example, the heteroduplexes containing the 2'-ara-fluoro deoxyribonucleotides, which produce a minor groove width comparable to the RNA/DNA heteroduplex, exhibited comparable human RNase H1 cleavage rates. On the other hand, deoxyribonucleotide modifications exhibiting a northern biased sugar conformation, (e.g., 2'-thiothymidine) reduced human RNase H1 activity. Consequently, the wider minor groove generated by these modifications likely precludes the associated metal ion coordination of the enzyme with the 2'-hydroxyl of the scissile ribonucleotide and electrostatic interaction with the phosphate of the modified deoxyribonucleotide. Similarly, a wider minor groove could account for the observed reduction in the site-specific rates for the adjacent 3'-ribonucleotide by preventing the formation of the putative hydrogen bond between the enzyme and the 2'-hydroxyl of the ribonucleotide at position +1 and the electrostatic interaction with the phosphate of the opposing deoxyribonucleotide. Consistent with these observations and the proposed model for the interaction of the enzyme with the heteroduplex substrate at the catalytic site, the significantly slower cleavage rates observed for the 4'-methylthymidine heteroduplexes suggest that proper positioning of the deoxyribonucleotide phosphate opposing the scissile ribonucleotide is critical for human RNase H1 cleavage. In addition, these observations suggest that the human RNase H1 activity associated with the deoxyribonucleotides exhibiting the northern verses southern biased sugar conformations is likely the result of differences in the relative positions of the inter- and intranucleotide phosphates on the heteroduplex substrate. Lastly, the cleavage rates observed for the 3'-methylthymidine modified heteroduplexes suggest minor groove widths that are narrower than the RNA/DNA heteroduplex are tolerated better than are wider minor grooves by human RNase H1.

Conformational flexibility of the deoxyribose also appears to be an important structural feature of the heteroduplex substrate for human RNase H1 activity. The preferred eastern $O_{4'}$-endo sugar pucker observed for the DNA strand of the heteroduplex is the result of the nearly symmetrical potential energy barrier for both south and north sugar conformations exhibited by deoxyribonucleotides. Both the pseudouridine and 2'-arafluoro-deoxyribonucleotides exhibit conformational flexibility in the sugar and the heteroduplexes containing these modifications showed cleavage rates comparable to the unmodified substrate. Furthermore, modifications exhibiting strong conformationally biased sugars, (e.g., 2'-fluoro-deoxyribonucleotides) were less efficiently cleaved by the enzyme.

Whereas conformational flexibility of the deoxyribose was preferred, flexibility in the in the phosphate backbone of the DNA strand inhibited human RNase H1 activity. Modifications such as the hydrocarbon linkers and abasic deoxyribonucleotides that permit free rotation of the phosphate moiety were shown to inhibit human RNase H1 activity. Again these data suggest that proper positioning the phosphate groups of the deoxyribonucleotide, presumably for electrostatic contact with the enzyme, is essential for human RNase H1 catalysis. The cleavage rates observed for the π-stacking deoxyribonucleotides suggest that stable base-stacking independent of hydrogen bond formation between the bases at the catalytic site appeared to offer sufficient rigidity to the phosphate backbone. Taken together these data suggest that variation in sugar conformation is significantly better tolerated by human RNase H1 than conformational flexibility in the phosphate backbone.

Previous studies have shown that nucleotides exhibiting conformationally based sugars can bias the sugar conformation of the surrounding deoxyribonucleotides. For example, the NMR structures of chimeric RNA-DNA/RNA heteroduplexes show that the deoxyribonucleotides adjacent to the RNA of the chimeric strand adopt the northern pucker of the RNA (Zhu, et. al., *Biochemistry* 1995, 34, 2372-2380). The transmission the northern sugar conformation of the RNA into the adjacent deoxyribonucleotides is likely due the intrinsically flexible nature of the deoxyribose sugar. Furthermore, these data suggest that modifications resulting in higher conformationally biased sugar populations would have a greater influence on the structure of the surrounding deoxyribonucleotides and consequently a greater impact on human RNase H1 activity. The impact of the highly northern biased 2'-fluoro deoxyribonucleotide modification on the human RNase H1 activity of the surrounding ribonucleotides shown here, suggests that conformational transmission exhibits a modest influence on human RNase H1 activity compared to other factors such as steric bulk in the minor groove and conformational flexibility within the phosphate backbone. It is important to note that the heteroduplexes examined here contained single nucleotide substitutions with a conformationally biased sugar. It has also been observed that substituting contiguous stretches of modified nucleotides with conformationally biased sugars exhibits a greater influence on the human RNase H1 activity against adjacent deoxyribonucleotides. The structure of human RNase H1 shows that in addition to the catalytic domain shared with the E. coli homolog, human RNase H1 contains an RNA-binding domain at the N-terminus of the protein (Wu, Lima and Crooke, *Antisense Nucleic Acid Drug Dev.* 1998, 8, 53-61) Human RNase H1 appears to identify the first 3'-DNA/5'-RNA base pair to achieve the proper positioning of the catalytic domain slightly less than one helical turn from the RNA-binding domain (Lima, et. al., *J. Biol. Chem.* 2003, 278, 49860-49867). Only when the enzyme is bound at the correct site and the helical geometry is appropriate will the catalytic unit be positioned appropriately to cleave the RNA. As a result, altering the local helical geometry, (e.g., altering the minor groove width or the inter- and intranucleotide phosphate distances) at the catalytic site on the heteroduplex may have a global effect on the precise positioning of the catalytic region with respect to the RNA-binding domain of human RNase H1 required for catalysis. Because the enzyme is predicted to position the catalytic domain 3' on the RNA relative to the RNA-binding domain, consistent with the results presented here, a local change in duplex geometry at the catalytic site on the substrate would impair the human RNase H1 activity at the adjacent 3'-ribonucleotides to the modification.

Implications for the Design of Antisense Oligonucleotides

The demonstration that human RNase H1 plays a dominant role in the activities of DNA-like ASOs suggests that additional studies that explore the substrate preferences, enzymology, and regulatory processes for RNase H1 should support improved design of antisense agents. The demonstration that increases in RNase H1 activity correlated with increases in potency suggests that recruitment of RNase H1 to the ASO-RNA duplex and/or cleavage of the RNA by the enzyme is limiting for ASO activity. Any strategy that would improve these processes should improve ASO potency.

We have shown that chimeric ASOs containing 2'methoxyethoxy nucleotides in the wings and deoxyribonucleotides in the gap demonstrably enhance affinity for the target RNA and the nuclease stability. Despite the dramatic enhancement in binding affinity and nuclease stability, these chimeric ASOs only increase potency by 5 to 10-fold. This is due to a significant reduction in the catalytic efficiency of RNase H1 for these substrates. Thus strategies to enhance the interaction of human RNase H1 with the chimeric ASO-RNA complex are essential to increasing the potencies of this class of ASOs.

In that regard, the results presented here suggest that the preferred properties for the modified oligodeoxyribonucleotide include: 1) a conformationally flexible sugar producing an $O_{4'}$-endo pucker when hybridized to RNA; 2) no sterically bulky 2'-substituents; and 3) a conformationally rigid phosphate backbone. Clearly, the 2'-ara-fluoro, pseudouridine, 3'-methyl and π-stacking modified deoxyribonucleotides exhibit many of these qualities. In light of the fact that none of the modifications tested were shown to enhance human RNase H1 activity compared with native deoxyribonucleotides and that these modification offer no clear advantage over native deoxyribonucleotides with respect to either duplex stability or nuclease resistance, other strategies to improve the potency ASO should be considered. For example, the calculated placement of these modifications in chimeric ASOs may be an effective means to improve human RNase H1 activity by potentially blocking the conformational transmission of 2'-alkoxy deoxyribonucleotide into the deoxyribonucleotide region of the chimeric ASO.

Example 6

Additional Turnover Kinetic Studies 20-mer phosphate linked, oligonucleotides were prepared, of sequence AGTTTAGGTCTCCGATCGTC (SEQ ID NO:2; where A is 2'-MOE-A, G is 2'-MOE-G, T is 2'-MOE-T, and C is 2'-MOE-C.)

Each oligonucleotide incorporated one or two transition nucleotides positioned at the junction, or junctions, between regions of nucleotides comprising a particular sugar conformation and another region of nucleotides comprising a different sugar conformation. The modifications are indicated below, where (x) shows the position of the modification for the respective oligodeoxyribonucleotide (positions are numbered 5'→3' on the oligodeoxyribonucleotide.)

| | | |
|---|---|---|
| $T_4$ | AGTxTAGGTCTCCGATCGTC | (SEQ ID NO: 2) |
| $T_5$ | AGTTxAGGTCTCCGATCGTC | (SEQ ID NO: 2) |
| $A_6$ | AGTTTxGGTCTCCGATCGTC | (SEQ ID NO: 2) |
| $G_7$ | AGTTTAxGTCTCCGATCGTC | (SEQ ID NO: 2) |
| $G_8$ | AGTTTAGxTCTCCGATCGTC | (SEQ ID NO: 2) |
| $C_{13}$ | AGTTTAGGTCTCxGATCGTC | (SEQ ID NO: 2) |
| $G_{14}$ | AGTTTAGGTCTCCxATCGTC | (SEQ ID NO: 2) |
| $A_{15}$ | AGTTTAGGTCTCCGxTCGTC | (SEQ ID NO: 2) |
| $T_{16}$ | AGTTTAGGTCTCCGAxCGTC | (SEQ ID NO: 2) |
| $C_{17}$ | AGTTTAGGTCTCCGATxGTC | (SEQ ID NO: 2) |
| $A_6$-$T_{16}$ | AGTTTxGGTCTCCGAxCGTC | (SEQ ID NO: 2) |

The heteroduplex substrate containing the oligonucleotides were prepared as described in example 4, and the turnover kinetics determined as described in example 5. The results are shown below in table XII.

TABLE XII

Relative cleavage rates for modified heteroduplex substrates

| ISIS# | Mod | Mod Position | $V_0$ Ratio mod/unmod |
|---|---|---|---|
| 366696 | I | $T_4$ | 1.23 |
| 359469 | I | $T_5$ | 0.77 |
| 366694 | P | $T_5$ | 1.49 |
| 359473 | I | $A_6$ | 1.93 |
| 366695 | P | $A_6$ | 1.35 |
| 366697 | I | $G_7$ | 2.02 |
| 366698 | I | $G_8$ | 1.09 |
| 366701 | I | $C_{13}$ | 1.48 |
| 366700 | I | $G_{14}$ | 0.66 |
| 359471 | I | $A_{15}$ | 0.88 |
| 359470 | I | $T_{16}$ | 1.69 |
| 366699 | I | $C_{17}$ | 1.06 |
| 366702 | I | $A_6$-$T_{16}$ | 1.50 |

I = tetrafluoroindole
P = 2,3,4,5-tetrafluorophenyl

TABLE XII-continued

Relative cleavage rates for modified heteroduplex substrates

| ISIS# | Mod | Mod Position | V₀ Ratio mod/unmod |
|---|---|---|---|

[Chemical structure: tetrafluoroindole, labeled I]

[Chemical structure: pentafluorobenzyl group, labeled P]

Example 7

Inhibition of PTEN mRNA Expression in Mouse Brain Endothelial Cells by Tetrafluoroindole and N-3-methyl-2'-MOE-thymidine Modified Oligonucleotides The mouse brain endothelial cell line b.END was obtained from Dr. Werner Risau at the Max Plank Institute (Bad Nauheim, Germany). b.END cells were routinely cultured in DMEM, high glucose (Invitrogen Life Technologies, Carlsbad, Calif.) supplemented with 10% fetal bovine serum (Invitrogen Life Technologies, Carlsbad, Calif.). Cells were routinely passaged by trypsinization and dilution when they reached approximately 90% confluence. Cells were seeded into 96-well plates (Falcon-Primaria #3872) at a density of approximately 3000 cells/well for use in oligomeric compound transfection experiments.

20-mer phosphorothioate linked oligonucleotides, targeted to PTEN, of sequence CTGCTAGCCTCTGGATTTGA (SEQ ID NO:3, where A is 2'-MOE-A, G is 2'-MOE-G, T is 2'-MOE-T, and C is 2'-MOE-C), were prepared.

Each oligonucleotide of the present invention incorporated one or two transition nucleotides positioned at the junction, or junctions, between regions of nucleotides comprising a particular sugar conformation and another region of nucleotides comprising a different sugar conformation.

The oligonucleotides and the parent oligonucleotide ISIS 116847, (SEQ ID #3), containing no transition nucleotides (for comparison purposes) were tested in dose-response studies.

Mouse brain endothelial cells were transfected with 64, 32, 16, 8, 4, 2, 1 and 0.5 nM of oligonucleotide using 3 ug/ml LIPOFECTIN™ per 100 nM oligonucleotide in OPTI-MEM™ for 4 hrs. Media was exchanged and cells were incubated for 1 day. RNA was harvested, purified, and analyzed by real-time PCR for PTEN and cyclophilin levels.

Target levels were determined by quantitative real-time PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to PTEN are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

After isolation the RNA is subjected to sequential reverse transcriptase (RT) reaction and real-time PCR, both of which are performed in the same well. PCR reagents were obtained from Invitrogen Corporation, (Carlsbad, Calif.). RT, real time-PCR reactions were carried out by adding 20 μL PCR cocktail (2.5×PCR buffer minus MgCl₂, 6.6 mM MgCl₂, 375 μM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96-well plates containing 30 μL total RNA solution (20-200 ng). The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH or cyclophilin, genes whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent (Molecular Probes, Inc. Eugene, Oreg.). Methods of RNA quantification by RiboGreen™ are taught in Jones, L. J., et al, (Analytical Biochemistry, 1998, 265, 368-374).

In this assay, 170 μL of RiboGreen™ working reagent (RiboGreen™ reagent diluted 1:350 in 10 mM Tris-HCl, 1 mM EDTA, pH 7.5) is pipetted into a 96-well plate containing 30 μL purified, cellular RNA. The plate is read in a CytoFluor 4000 (PE Applied Biosystems) with excitation at 485 nm and emission at 530 nm.

PCR results were normalized to the ubiquitously expressed mouse cyclophilin. Probes and primers to mouse PTEN were designed to hybridize to a mouse PTEN sequence, using published sequence information (incorporated herein as SEQ ID NO:4, GENBANK accession number: U92437.1;

```
GGCGCCCTGCTCTCCCGGCGGGGCGGCGGAGGGGGCGGGCTGGCCGGCGC
ACGGTGATGTGGCGGGACTCTTTGTGCACTGCGGCAGGATACGCGCTTGG
GCGTCGGGACGCGGCTGCGCTCAGCTCTCTCCTCTCGGAAGCTGCAGCCA
TGATGGAAGTTTGAGAGTTGAGCCGCTGTGAGGCCAGGCCCGGCGCAGGC
GAGGGAGATGAGAGACGGCGGCGGCCACGGCCCAGAGCCCCTCTCAGCGC
CTGTGAGCAGCCGCGGGGCAGCGCCCTCGGGGAGCCGGCCGGGCGGCGG
CGGCGGCAGCGGCGGCGGGCCTCGCCTCCTCGTCGTCTGTTCTAACCGGG
CAGCTTCTGAGCAGCTTCGGAGAGAGACGGTGGAAGAAGCCGTGGGCTCG
AGCGGGAGCCGGCGCAGGCTCGGCGGCTGCACCTCCCGCTCCTGGAGCGG
GGGGGAGAAGCGGCGGCGGCGGCCGCGGCTCCGGGGAGGGGTCGGAGTC
GCCTGTCACCATTGCCAGGGCTGGGAACGCCGGAGAGTTGCTCTCTCCCC
TTCTCCTGCCTCCAACACGGCGGCGGCGGCGGCGGCACGTCCAGGGACCC
GGGCCGGTGTTAAGCCTCCCGTCCGCCGCCGCCGCACCCCCCCTGGCCCG
GGCTCCGGAGGCCGCCGGAGGAGGCAGCCGCTGCGAGGATTATCCGTCTT
CTCCCCATTCCGCTGCCTCGGCTGCCAGGCCTCTGGCTGCTGAGGAGAAG
CAGGCCCAGTCTCTGCAACCATCCAGCAGCCGCCGCAGCAGCCATTACCC
GGCTGCGGTCCAGGGCCAAGCGGCAGCAGAGCGAGGGGCATCAGCGACCG
CCAAGTCCAGAGCCATTTCCATCCTGCAGAAGAAGCCTCGCCACCAGCAG
CTTCTGCCATCTCTCTCCTCCTTTTTCTTCAGCCACAGGCTCCCAGACAT
GACAGCCATCATCAAAGAGATCGTTAGCAGAAACAAAAGGAGATATCAAG
AGGATGGATTCGACTTAGACTTGACCTATATTTATCCAAATATTATTGCT
ATGGGATTTCCTGCAGAAAGACTTGAAGGTGTATACAGGAACAATATTGA
TGATGTAGTAAGGTTTTTGGATTCAAAGCATAAAAACCATTACAAGATAT
ACAATCTATGTGCTGAGAGACATTATGACACCGCCAAATTTAACTGCAGA
GTTGCACAGTATCCTTTTGAAGACCATAACCCACCACAGCTAGAACTTAT
CAAACCCTTCTGTGAAGATCTTGACCAATGGCTAAGTGAAGATGACAATC
ATGTTGCAGCAATTCACTGTAAAGCTGGAAAGGGACGGACTGGTGTAATG
ATTTGTGCATATTTATTGCATCGGGGCAAATTTTTAAAGGCACAAGAGGC
CCTAGATTTTTATGGGGAAGTAAGGACCAGAGACAAAAAGGGAGTCACAA
TTCCCAGTCAGAGGCGCTATGTATATTATTATAGCTACCTGCTAAAAAAT
CACCTGGATTACAGACCCGTGGCACTGCTGTTTCACAAGATGATGTTTGA
AACTATTCCAATGTTCAGTGGCGGAACTTGCAATCCTCAGTTTGTGGTCT
GCCAGCTAAAGGTGAAGATATATTCCTCCAATTCAGGACCCACGCGGCGG
GAGGACAAGTTCATGTACTTTGAGTTCCCTCAGCCATTGCCTGTGTGTGG
TGATATCAAAGTAGAGTTCTTCCACAAACAGAACAAGATGCTCAAAAAGG
ACAAAATGTTTCACTTTTGGGTAAATACGTTCTTCATACCAGGACCAGAG
GAAACCTCAGAAAAGTGGAAAATGGAAGTCTTTGTGATCAGGAAATCGA
TAGCATTTGCAGTATAGAGCGTGCAGATAATGACAAGGAGTATCTTGTAC
TCACCCTAACAAAAAACGATCTTGACAAAGCAAACAAAGACAAGGCCAAC
CGATACTTCTCTCCAAATTTTAAGGTGAAACTATACTTTACAAAAACAGT
AGAGGAGCCATCAAATCCAGAGGCTAGCAGTTCAACTTCTGTGACTCCAG
ATGTTAGTGACAATGAACCTGATCATTATAGATATTCTGACACCACTGAC
TCTGATCCAGAGAATGAACCTTTTGATGAAGATCAGCATTCACAAATTAC
AAAAGTCTGA).
```

For mouse PTEN the PCR primers were:

forward primer:
(SEQ ID NO:5)
ATGACAATCATGTTGCAGCAATTC reverse primer:
(SEQ ID NO:6)
CGATGCAATAAATATGCACAAATCA and the PCR probe was:

(SEQ ID NO:7)
FAM-CTGTAAAGCTGGAAAGGGACGGACTGGT-TAMRA where FAM is the fluorescent dye and TAMRA is the quencher dye.

Untreated cells served as the control to which data were normalized. Data were averaged from [# experiments] experiments. The IC50, or concentration of oligonucleotide which yields a 50% reduction in mRNA expression, was calculated and is presented in Table XIII.

TABLE XIII

IC50 values for oligonucleotide inhibition of PTEN mRNA in mouse brain endothelial cells

| ISIS# | Sequence (5' → 3') | SEQ ID NO: | IC50 (nM) |
|---|---|---|---|
| 116847 | CTGCTAGCCTCTGGATTTGA | 3 | 3 |
| 376718 | CTGITAGCCTCTGGATTTGA | 15 | 37 |

TABLE XIII-continued

IC50 values for oligonucleotide inhibition of PTEN mRNA in mouse brain endothelial cells

| ISIS# | Sequence (5' → 3') | SEQ ID NO: | IC50 (nM) |
|---|---|---|---|
| 376719 | CTGCIAGCCTCTGGATTTGA | 16 | 13 |
| 376720 | CTGCTIGCCTCTGGATTTGA | 17 | 13 |
| 376721 | CTGCTAICCTCTGGATTTGA | 18 | 10 |
| 376722 | CTGCTAGICTCTGGATTTGA | 19 | 10 |
| 376723 | CTGCTAGCCICTGGATTTGA | 20 | 5 |
| 376727 | CTGCNAGCCTCTGGATTTGA | 21 | 14 |
| 376713 | CTGCTAGCCTCTGGATITGA | 22 | 4 |
| 376714 | CTGCTAGCCTCTGGAITTGA | 23 | 8 |
| 376715 | CTGCTAGCCTCTGGITTTGA | 24 | 5 |
| 376716 | CTGCTAGCCTCTGIATTTGA | 25 | 5 |
| 376717 | CTGCTAGCCTCTIGATTTGA | 26 | 8 |
| 376724 | CTGCIAGCCTCTGGITTTGA | 27 | 19 |
| 376726 | CTGCTAGCCTCTGGANTTGA | 28 | 6 |

I = tetrafluoroindole
N = N-3-methyl-2'-MOE-thymidine

These data demonstrate that these compounds inhibited mouse brain endothelial PTEN mRNA expression in a dose-dependent manner.

Example 8

Inhibition of PTEN mRNA Expression in Mouse Brain Endothelial Cells by a 4-methyl-1H-benzimidazole Modified Oligonucleotide Three ASOs were prepared as described in the above examples and their inhibition of PTEN mRNA expression in mouse brain endothelial cells was examined as described above in example 7. Mouse brain endothelial cells were transfected with 100, 50, 25, 10, 5 and 1 nM of oligonucleotide.

ISIS 141923, a 20-mer phosphorothioate oligonucleotide of sequence CCTTCCCTGAAGGTTCCTCC (SEQ ID NO:8, where C=2'-MOE-5-methyl-C and T=2'-MOE-T) is a "mismatch" to the PTEN target, and was used as a control compound.

ISIS116847, a 20-mer phosphorothioate oligonucleotide of sequence CTGCTAGCCTCTGGATTTGA (SEQ ID NO:3, where C=2'-MOE-5-methyl-C, T=2'-MOE-T and G=2'-MOE-G) is the parent active compound, complimentary to PTEN.

ISIS362257, a 20-mer phosphorothioate oligonucleotide of sequence CTGCTAGCCTCTGGATTTGA (SEQ ID NO:3, where C=2'-MOE-5-methyl-C, T=2'-MOE-T, G=2'-MOE-G and A=4-methyl-1H-Benzimidazole) corresponds to ISIS116847, its parent unmodified analog, and contains a transition nucleotide at position 15, where the A base has been replaced with 4-methyl-1H-Benzimidazole.

Data are averages from [# experiments] experiments, and are summarized in Table XIV. Where present, n.d. indicates "not determined".

TABLE XIV

Inhibition of PTEN mRNA expression in mouse brain endothelial cells

| | | % Inhibition Dose of oligonucleotide | | | | | |
|---|---|---|---|---|---|---|---|
| ISIS # | SEQ ID # | 1 nM | 5 nM | 10 nM | 25 nM | 50 nM | 100 nM |
| 141923 | 8 | n.d. | n.d. | n.d. | n.d. | 111 | 100 |
| 362257 | 3 | 82 | 81 | 85 | 62 | 46 | 33 |
| 116847 | 3 | 69 | 34 | 17 | 15 | 14 | 18 |

These data demonstrate that ISIS 141923 (control) showed no effect on mouse brain endothelial PTEN mRNA expression, and ISIS362257 and ISIS116847 inhibited b.End PTEN mRNA expression in a dose-dependent manner.

Example 9

In Vivo Inhibition of PTEN mRNA Expression in Mouse Liver by Tetrafluoroindole Modified Oligonucleotides In accordance with the present invention, four antisense compounds described in example 7 were investigated for their activity in vivo. ISIS 141923 (CCTTCCCTGAAGGTTCCTCC, SEQ ID NO:8) served as a control compound, having no complementary base sequence to the PTEN target. It is a chimeric oligonucleotide ("gapmer") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. The internucleoside (backbone) linkages are phosphorothioate (P=S) throughout the oligonucleotide and all cytidine residues are 5-methylcytidine.

ISIS116847 (CTGCTAGCCTCTGGATTTGA, SEQ ID NO:3) served as the parent unmodified control compound and is also a chimeric oligonucleotide ("gapmer") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. The internucleoside (backbone) linkages are phosphorothioate (P=S) throughout the oligonucleotide and all cytidine residues are 5-methylcytidine. This compound is complementary to the PTEN target.

ISIS376715, a compound of the present invention, is a chimeric oligonucleotide ("gapmer") 20 nucleotides in length, of the same sequence as its parent analog (ISIS116847, SEQ ID NO:3) additionally containing a transition nucleotide at position 15, where the A base has been replaced with tetrafluoroindole. Similar to its parent analog, it is composed of a central "gap" region consisting, however of nine 2'-deoxynucleotides (the tenth being replaced with the transition nucleotide), which is flanked on both sides (5' and 3' directions) by five-nucleotide "wings". The wings are composed of 2'-methoxyethyl (2'-MOE) nucleotides. The internucleoside (backbone) linkages are phosphorothioate (P=S) throughout the oligonucleotide and all cytidine residues are 5-methylcytidine.

ISIS376716 also a compound of the present invention, is a chimeric oligonucleotide ("gapmer") 20 nucleotides in length, of the same sequence as its parent analog (ISIS116847, SEQ ID NO:3) additionally containing a transition nucleotide at position 14, where the G base has been replaced with tetrafluoroindole. Similar to its parent analog, it is composed of a central "gap" region consisting, however of nine 2'-deoxynucleotides (the tenth being replaced with the transition nucleotide), which is flanked on both sides (5' and 3' directions) by five-nucleotide "wings". The wings are composed of 2'-methoxyethyl (2'-MOE) nucleotides. The internucleoside (backbone) linkages are phosphorothioate (P=S) throughout the oligonucleotide and all cytidine residues are 5-methylcytidine.

Male 6-week old Balb/c mice (Charles River Laboratories, Wilmington, Mass.) were given intraperitoneal injections of ISIS141923, ISIS116847, ISIS376715 or ISIS376716 at a dose of 4, 2, or 1 umoles/kg, twice per week for two weeks. Saline-injected animals also served as a control. Each treatment group contained XX animals. The mice were sacrificed 2 days following administration of the fourth and final dose of oligonucleotide or saline.

Mice were evaluated for PTEN mRNA levels in kidney, which were determined by quantitative real-time PCR as described in the above examples.

The data are expressed as percent PTEN mRNA expression relative to saline treated animals and are shown in Table XV.

TABLE XV in vivo inhibition of PTEN mRNA expression
% PTEN mRNA expression, relative to saline

| Dose (umol/kg) | ISIS 141923 | ISIS 116847 | ISIS 376715 | ISIS 376716 |
|---|---|---|---|---|
| 4 | 110 | 28 | 31 | 34 |
| 2 | n.d. | 24 | 55 | 52 |
| 14 | n.d. | 58 | 77 | 64 |

These data illustrate that antisense compounds containing transition nucleotides inhibit the expression of PTEN mRNA in mouse liver.

It is intended that each of the patents, applications, and printed publications including books mentioned in this patent document be hereby incorporated by reference in their entirety. As those skilled in the art will appreciate, numerous changes and modifications may be made to the preferred embodiments of the invention without departing from the spirit of the invention. It is intended that all such variations fall within the scope of the invention.

What is claimed is:

1. A method of modulating the expression of a target RNA molecule in a eukaryotic cell comprising the step of contacting the cell with an oligonucleotide consisting of 8 to 80 linked nucleosides and having
   a) a first region of nucleotides, each having a first conformation which, when the oligonucleotide is bound to the target RNA molecule, forms a substrate for cleavage by an RNase;
   b) a second region of nucleotides, each having a second conformation which, when the oligonucleotide is bound to the target RNA molecule does not form a substrate for cleavage by an RNase, and
   c) a transition moiety positioned between the first and the second regions which modulates the transmission of the conformation of the second region into the first region, wherein the transition moiety comprises at least one modified nucleotide that does not form hydrogen bonds with the target RNA molecule, wherein the modified nucleotide is (i) a modified or unmodified sugar abasic nucleotide, or (ii) comprises a modified nucleobase selected from the group consisting of a universal base, a hydrophobic base, and a fluorinated nucleobase.

2. The method of claim 1, wherein the second region is positioned 5' to the first region.

3. The method of claim 1, wherein the first region comprises deoxynucleotides.

4. The method of claims 3, wherein the second region comprises 2'-O-alkoxyalkyl ribonucleotides.

5. The method of claim 4, wherein the 2'-O-alkoxyalkyl ribonucleotides are 2'-O-methoxyethyl ribonucleotides.

6. The method of claim 1, wherein the internucleotide linkages in the first or second regions are phosphorothioates.

7. The method of claim 1, wherein the modified nucleobase of the transition moiety is capable of π stacking with adjacent bases.

8. The method of claim 7, wherein the modified base moiety is tetrafluoroindolyl.

9. The method of claim 1, wherein the modified sugar nucleotide is a 2'-ara-modified nucleotide.

10. The method of claim 9, wherein the 2'-ara-modified nucleotide is a 2'-ara-fluoro nucleotide.

11. The method of claim 1, wherein the oligonucleotide comprises a third region of nucleotides, each having a conformation which, when the oligonucleotide is bound to the target RNA molecule does not form a substrate for cleavage by an RNase.

12. The method of claim 11, wherein the third region has the same conformation as the second region.

13. The method of claims 12, wherein the second region comprises 2'-O-alkoxyalkyl ribonucleotides.

14. The method of claim 13, wherein the 2'-O-alkoxyalkyl ribonucleotides are 2'-O-methoxyethyl ribonucleotides.

15. The method of claim 11, wherein the oligonucleotide comprises a second transition moiety which modulates the transmission of the conformation of the third region into the first region, and wherein the second transition moiety comprises at least one modified nucleotide that does not form hydrogen bonds with the target RNA molecule, wherein the modified nucleotide is (i) a modified or unmodified sugar abasic nucleotide, or (ii) comprises a modified nucleobase selected from the group consisting of a universal base, a hydrophobic base, and a fluorinated nucleobase.

16. The method of claim 15, wherein the modified base nucleotide of the second transition moiety comprises a modified base moiety capable of π stacking with adjacent bases.

17. The method of claim 15, wherein the modified base moiety of the second transition moiety is tetrafluoroindolyl.

18. The method of claim 15, wherein the modified sugar nucleotide of the second transition moiety is a 2'-ara-modified nucleotide.

19. The method of claim 15, wherein the 2'-ara-modified nucleotide of the second transition moiety is a 2'-ara-fluoro nucleotide.

20. The method of claim 15, wherein the modified sugar moiety of the second transition moiety is an acyclic sugar analog.

21. The method of claim 1, wherein the eukaryotic cell is in an animal.

* * * * *